(12) United States Patent
Baron et al.

(10) Patent No.: US 6,713,065 B2
(45) Date of Patent: Mar. 30, 2004

(54) METHODS OF USING HEDGEHOG PROTEINS TO MODULATE HEMATOPOIESIS AND VASCULAR GROWTH

(75) Inventors: Margaret H. Baron, New York, NY (US); Sarah M. Farrington, Cambridge, MA (US); Maria Belaoussoff, Göttingen (DE)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/021,660

(22) Filed: Feb. 10, 1998

(65) Prior Publication Data

US 2001/0041668 A1 Nov. 15, 2001

Related U.S. Application Data

(60) Provisional application No. 60/049,763, filed on Jun. 16, 1997, and provisional application No. 60/037,513, filed on Feb. 10, 1997.

(51) Int. Cl.[7] ............................................... A61K 38/18
(52) U.S. Cl. ................. 424/198.1; 424/85.1; 424/93.21; 530/351
(58) Field of Search ............................. 514/2, 12, 44; 530/300, 350, 351; 424/130.1, 93.2, 94.1, 85.1, 93.21, 198.1; 435/6, 7.1

(56) References Cited

FOREIGN PATENT DOCUMENTS

| WO | WO95/18856 | 7/1995 |
|---|---|---|
| WO | WO96/16668 | 6/1996 |

OTHER PUBLICATIONS

Willimans et al. Functional antagonists of sonic hedgehog reveal the imporance of hte Nteminus for activity, J. Cell. Sci., 199 Dec., 112 (Pt. 23): 4405, abstract only.*
Hemmati–Brivanlou et al., Ventral mesodermal patterning in Xenopus embryos: expression patterns and activities of BMP–2 and BMP–4, Dev. Genet., 17:78–89, 1995.*
Zeigler et al., In vitro megakaryocytopoietic and thrombopoietic activity of c–mpl ligand (TPO) on purified murine hematopoietic stem cells, Blood, 84(12): 4045–4052, Dec. 1994.*
Bhardwaj et al., Sonic hedgehog induces the proliferation of primative human hematopietic cells via BMP regulation, Nature Immunol. (Feb. 2001) 2(2):172–1180.*
Detmer et al., Erythroid differentiation in vitro is blocked by cyclopamine, an inhibitor of hedgehog signaling, Blood Cells, Molecules, and Diseases (Aug. 2000) 26(4): 360–372.*
Anderson, D.M., *Cell,* vol. 63, pp. 235–243, (1990).
Ang, Siew–Lan, et al., *Development,* 118, pp. 139–149, (1993).
Asahara, T., et al., *Science,* vol. 275, pp. 964–967 (1997).

Baron, M. H., et al., *Cell,* vol. 46, pp. 591–602, (1986).
Baron, M. H., et al., *Molecular and Cellular Biology,* pp. 3108–3114, (1994).
Beddington, R. S. P., *J. Embryo, Exp. Morph.*. vol. 64, pp. 87–104, (1981).
Beddington, R.S.P., *J. Embryo. Exp. Morpho.,* vol. 69, pp. 265–285, (1982).
Bitgood, M. J., et al., *Current Biology,* vol. 6 No. 3, pp. 298–304, (1996).
Blau, H. M., et al., *New England Journal of Medicine.,* vol. 333, pp. 1204–1207, (1995).
Blau, H. M., et al., *New England Journal of Medicine,* vol. 333, pp. 1554–1556, (1995).
Bobola, N., et al., *The Journal of Biological Chemistry.,* vol. 270, pp. 1289–1294, (1995).
Caceres–Cortes, J., et al., *J. Biol. Chem.,* vol. 269, pp. 12084–12091, (1994).
Carmellet, P., et al., *Nature,* vol. 380, pp. 435–439, (1996).
Chen, L.T., et al, *Exp. Hemat.,* vol. 7, No. 5, pp. 231–244, (1979).
Chiang, Chin, et al., *Nature,* vol. 383, pp. 407–413, (1996).
Chiquoine, A.D., *The Anatomical Record.,* vol. 118, pp. 135–145 (1954).
Chomezynski, P., et al., *Anal. Biochem,* vol. 162, pp. 156–159, (1987).
Ciavatta, D.J., et al., *Proc. Natl. Acad. Sci. USA,* vol. 92, pp. 9259–9263, (1995).
Coffin, J. D., et al., *Developmental Biology,* 148, pp. 51–62 (1991).
Cumano, A., et al., *Cell,* vol. 86, pp. 907–916, (1996).
Deng, Chu–Xia, et al., *Genes & Development,* vol. 8, pp. 3045–3057, (1994).
Dickson, M. .C., et al., *Development,* vol. 121, pp. 1845–1854, (1995).
Dieterlen–Lievre, F., *J. Embryol. Exp. Morph.,* vol. 33 No. 3, pp. 607–619, (1975).
DiGiusto, D. L., et al., *Blood,* vol. 87, No. 4, pp. 1261–1271, (1996).
Dolci, S., et al., *Nature,* vol. 352, pp. 809–822, (1991).
Downs, Karen M., et al., *Development,* vol. 118, pp. 1255–1266, (1993).
Dyer, M. A., et al., *Hemoglobin Switching,* pp. 135–151. (1995).
Dzierzak, E., et al., *TIG.,* vol. 11, No. 9, pp. 359–366, (1995).
Echelard, Y., et al., *Cell,* vol. 75, pp. 1417–1430, (1993).
Ericson, J., et al., *Cell,* vol. 87, pp. 661–673, (1996).
Farrington, S.. M., et al., *Mechanisms of Development,* vol. 62, pp. 197–211, (1997).
Feinberg, R. N., et al., *Biomed,* vol. 14, pp. 58–68, (1991).

(List continued on next page.)

Primary Examiner—Lorraine Spector
(74) Attorney, Agent, or Firm—Ropes & Gray LLP

(57) ABSTRACT

This application pertains to methods and compositions that modulate proliferation and/or differentiation of undifferentiated mesodermally-derived cells so as to have an effect on at least one of vascular growth and hematopoiesis.

80 Claims, 20 Drawing Sheets

OTHER PUBLICATIONS

Feldman, B., et al., *Science,* vol. 267, pp. 246–249, (1995).
Ferrara, N., et al., *Nature,* vol. 380, pp. 439–442, (1996).
Flamme, I., et al., *The Anatomical Record,* vol. 237, pp. 49–57, (1993).
Folkman, J., *New England Journal of Medicine* 333, pp. 1757–1763, (1995).
Folkman, J., et al., *Science,* vol. 235, pp. 442–447, (1987).
Folkman, J., et al, *J. Biol. Chem.,* pp. 10931–10934, (1992).
Folkman, J., et al., *Cell,* vol. 87, pp. 1153–1155, (1996).
Forrester, W., et al., *Proc. Natl. Acad. Sci. USA,* vol. 86, pp. 5439–5443, (1989).
Gendron, Robert L., et al.,*Developmental Biology,* vol. 177, pp. 332–346,(1996).
Ginsburg, M., et al., *Development,* vol. 110, pp. 521–528, (1990).
Godin, I., et al., *Nature,* vol. 352, pp. 807–809, (1991).
Godin, Isabelle E., et al., *Nature,* vol. 364, pp. 67–70, (1993).
Godin, Isabelle, et al., *Proc. Natl. Acad. Sci. USA,* vol. 92, pp. 773–777, (1995).
Goodell, Margaret A., et al., *Nature Medicine,* vol. 3,, pp. 1337–1345, (1997).
Goodrich, Lisa V., et al., *Genes & Development,* vol. 10, pp. 301–312, (1996).
Gordon–Thomson, C. and B.C. Fabian, *Development,* vol. 120, pp. 3751–3579, (1994).
Hahnel, A.C., et al., *Gamete Res.,* vol. 15, pp. 25–34, (1986).
Hanks, Mark., et al., *Science,* vol. 269, pp. 679–682, (1995).
Hanscombe, O., et al., *Genes & Develop.,* vol. 3, pp. 1572–1581, (1989).
Herbomel, P., *Cell,* vol. 39, pp. 653–662, (1983).
Heyworth, C.M., et al., *Haemopoiesis, A Practical Approach,* pp. 37–53, Testa, N.G. and Molineux, G., eds., Oxford University Press (1993).
Hogan, B., et al., *Manipulating the Mouse Embryo: A Laboratory Manual,* Cold Spring Harbor, Cold Spring Harbor Laboratory Press, pp. 219–305, 373–375, (1994).
Hsu, Y.–C., *Dev. Biol.,* vol. 68, pp. 453–461, (1979).
Huang, Hua and Robert Auerbach, *Proc. Natl. Acad. Sci. USA,* vol. 90, pp. 10110–10114, (1993).
Johansson, B.M. and Wiles, M.V., *Mol. Cell Biol.,* vol. 15, pp. 141–151, (1995).
Johnson, R.L., et al., *Science,* vol. 272, pp. 1668–1671, (1996).
Joyner, A. L., *Gene Targeting: A Practical Approach,* New York IRL Press, pp. 1–146, (1995).
Kanatsu, Mito and Shin–Ichi Nishikawa, *Development,* vol. 122, pp. 823–830, (1996).
Keller, Gordon M., et al., *Current Opinion Cell Biology.* vol. 7, pp. 862–869, (1995).
Kennedy, M., et al., *Nature,* vol. 386, pp. 488–493, (1997).
Kinzler, Kenneth W., et al., *Science,* vol. 236, pp. 70–73, (1987).
Kurz, Haymo, et al., *Developmental Biology,* vol. 173, pp. 133–147 (1996).
Lawson, K.A., et al., *Development,* vol. 113, pp. 891–911, (1991).
Lord, B. I., *Haemopoiesis, A Practical Approach,* pp. 1–20, Testa, N.G. and Molineux, G., eds., Oxford University Press (1993).
Lord, B. I., et al., *Haemipoiesis, A Practical Approach,* pp. 21–36, Testa, N.G. and Molineux, G., eds., Oxford University Press (1993).

Lyons, Gary E., et al., *The Journal of Cell Biology,* vol. III, pp. 2427–2436, (1990).
Marshall, Eliot, *Science,* vol. 271, pp. 586–588, (1996).
Matsui, Yasuhisa, et al., *Nature,* vol. 347, pp. 667–669, (1990).
Matsui, Yasuhisa, et al., *Cell,* vol. 70, pp. 841–847, (1992).
McClanahan, T., et al., *Blood,* vol. 81, pp. 2903–2915, (1993).
McLaughlin, K.J., *Guide to Techniques in Mouse Development,* Wassarman, P.M. and DePamphilis, M.L., eds., Academic Press, Inc., San Diego, (1993).
Medvinsky, Alexander L., *Nature,* vol. 364, pp. 64–67, (1993).
Medvinsky, Alexander L., et al., *Blood,* vol. 87, No. 2, pp. 557–566, (1996).
Medvinsky, Alexander and Elaine Dzierzak, *Cell,* vol. 86, pp. 897–906, (1996).
Miles, Colin, et al.,*Development,* vol. 124, pp. 537–547, (1997).
Millauer, B., et al., *Cell,* vol. 72, pp. 835–846, (1993).
Mintz, B., et al., *J. Embryo. Exp. Morphol.,* vol. 5, pp. 396–403, (1957).
Miura, Yasusada and Fred H. Wilt, *Developmental Biology,* vol. 19, pp. 201–211, (1969).
Moore, Malcolm A. S. and Donald Metcalf, *British Journal of Haematology,* vol. 18, pp. 279–295, (1970).
Morrison, Sean J., et al., *Proc. National Acad. Sci. USA,* vol. 92, pp. 10302–10306, (1995).
Morrison, Sean J., et al., *Annu. Rev. Cell Dev. Biol.,* vol. 11, pp. 35–71, (1995).
Mortensen, Robert.M., et al., *Molecular and Cellular Biology,* vol. 12, pp. 2391–2395, (1992).
Moses, Marsha A, et al., *International Review of Cytology,* vol. 161, pp. 1–48, (1995).
Müller, Albrecht, et al., *Immunity,* vol. 1, pp. 291–301, (1994).
Mummery, C.L., et al., *Developmental Biology,* vol. 109, pp. 402–410, (1985).
Needham, M., et al., *Nucleic Acid Research,* vol. 20, pp. 997–1003, (1992).
Orkin, Stuart H., *Current Opinion in Cell Biology,* vol. 7, pp. 870–877, (1995).
Oshima, Masanobu, et al., *Developmental Biology,* vol. 179, pp. 297–302, (1996).
Palis, James, et al., *Blood,* vol. 86, No.1, pp. 156–163, (1995).
Papaioannou, V. And Johnson, R., *Gene Targeting: A Pratical Approach,* Joyner, A.L., ed. IRL Press, New York, (1995).
Parameswaran, M. And Tam, P.P., *Dev. Genet.,* vol. 17, pp. 16–28, (1992).
Pardanaud, Luc, et al., *Development,* vol. 100, pp. 339–349, (1987).
Pardanaud, Luc, et al., *Development,* vol. 105, pp. 473–485, (1989).
Pardanaud, Luc, et al., *Development,* vol. 122, pp. 1363–1371, (1996).
Partanen, Juha, et al., *Development* , vol. 122, pp. 3013–3021 (1996).
Peault, Bruno M., et al., *Proc. Natl. Acad. Sci. USA,* vol. 80, pp. 2976–2980, (1983).
Peault, Bruno M., et al., *Cell Differentiation,* vol. 23, pp. 165–174, (1988).

Platt, Kenneth A., et al., *Mechanisms of Development*, vol. 62, pp. 121–135, (1997).

Pondel, M.D., et al., *Nucleic Acids Res.*, vol. 20, No. 21, pp. 5655–5660, (1992).

Riddle, R., et al., *Cell*, vol. 75, pp. 1401–1416, (1993).

Risau, W., *Biomed*, vol. 14, pp. 58–68, (1991).

Risau, W., *Pharmacology and Therapeutics*, vol. 51, pp. 371–376, (1991).

Risua, W., et al., *Development*, vol. 102, pp. 471–478, (1988).

Robertson, E.J., ed., IRL Press, pp. 79–81, *Teratocarcinomes and Embryonic Stem Cells, A Practical Approach*, Oxford IRS Press (1993).

Sauer, B., *In Guide to Techniques in Mouse Development.* Wasserman, P.M. and DePamphilis, M.L., eds., Academic Press, Inc., San Diego, (1993).

Serra, R., et al., *Development*, vol. 121, pp. 3057–3066, (1995).

Shalaby, Fouad, et al., *Nature*, vol. 376, pp. 62–67, (1995).

Skow, L.C., et al., *Cell*, vol. 34, pp. 1043–1052, (1983).

Soudais, Claire, et al., *Developmental*, vol. 121, pp. 3677–03888, (1995).

Stainier, Didier Y.R., et al., *Development*, vol. 125, pp. 3141–3150, (1995).

Stone, Donna M., et al, *Nature*, vol. 384, pp. 129–134, (1996).

Tavian, Manuela, et al., Blood, vol. 87, pp. 67–72, (1996).

Trepicchio, William L., et al., *Molecular and Cellular Biology*, vol. 13, No. 12, pp. 7457–7468, (1993).

Trepicchio, William L., et al., *Molecular and Cellular Biology*, vol. 14, No. 6, pp. 3763–3771, (1994).

Trepicchio, William L., et al., *Journal of Sequencing and Mapping*, vol. 4, pp. 409–412, (1994).

Tsai, F.–Y., et al., *Nature*, vol. 371, pp. 221–226, (1994).

Vortkamp, A., et al., *Science*, vol. 273, pp. 613–622, (1996).

Wassarman, P. M. and Melvin L. DePamphilis, eds., *Guide to Techniques in Mouse Development*, vol. 225, pp. 461–463, (1993).

Whetton, Anthony D. and T. Michael Dexter, *Current Opinion in Cell Biology* vol. 5, pp. 1044–1049, (1993).

Wilt, F. H., *Science*, vol. 147, pp. 1588–1590, (1965).

Wilting, J., *Developmental Biology*, vol. 176, pp. 76–85, (1996).

Winnier, G., et al., *Genes & Development*, vol. 9, pp. 2105–2116, (1995).

Witte, O.N., *Cell*, vol. 63, pp. 5–6, (1990).

Wurst, W. and Joyner, A.L.,. *Gene Targeting: A Pratical Approach.* Joyner, A.L., ed., IRL Press, New York, (1995).

Young, P.E., et al., *Blood*, vol. 85, pp. 96–105, (1995).

Zhang, H. And Bradley, A., *Development*, vol. 122, pp. 2977–2986, (1996).

* cited by examiner 7.5 DAYS pc
BLOOD ISLANDS 7.5 DAYS pc
BLOOD ISLANDS 7.5 DAYS pc
BLOOD ISLANDS 8.5 DAYS pc
VASCULAR CHANNELS 8.5 DAYS pc
VASCULAR CHANNELS 12.5 DAYS pc
VITELLINE CIRCULATION

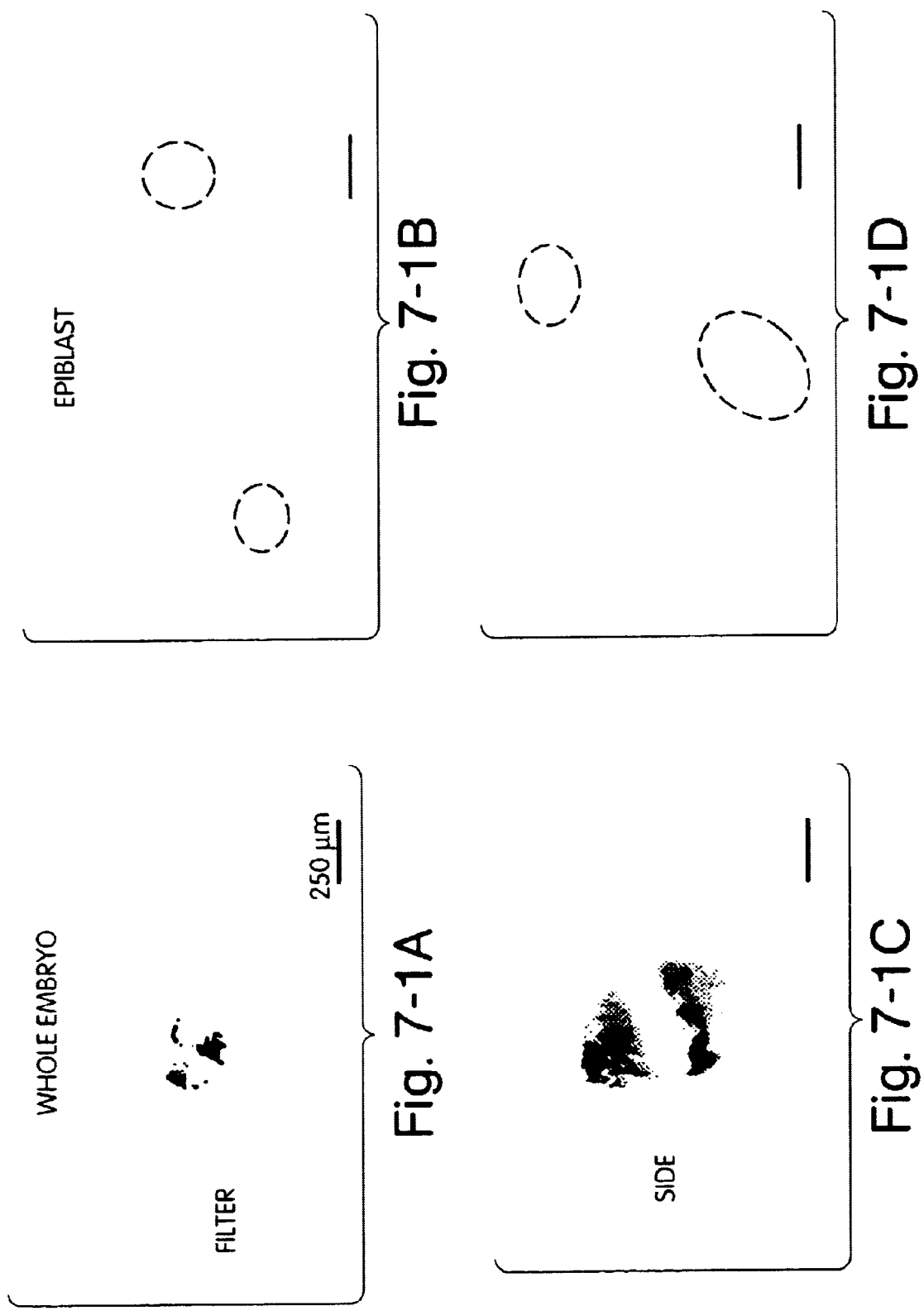

$2\frac{1}{2}$d  ZONA PELLUCIDA

ICM $3\frac{1}{2}$d  TROPHECTODERM

ECTODERM

ENDODERM $4\frac{1}{2}$d

TROPHECTODERM
MURAL   POLAR

VISCERAL

PARIETAL $5\frac{1}{2}$d

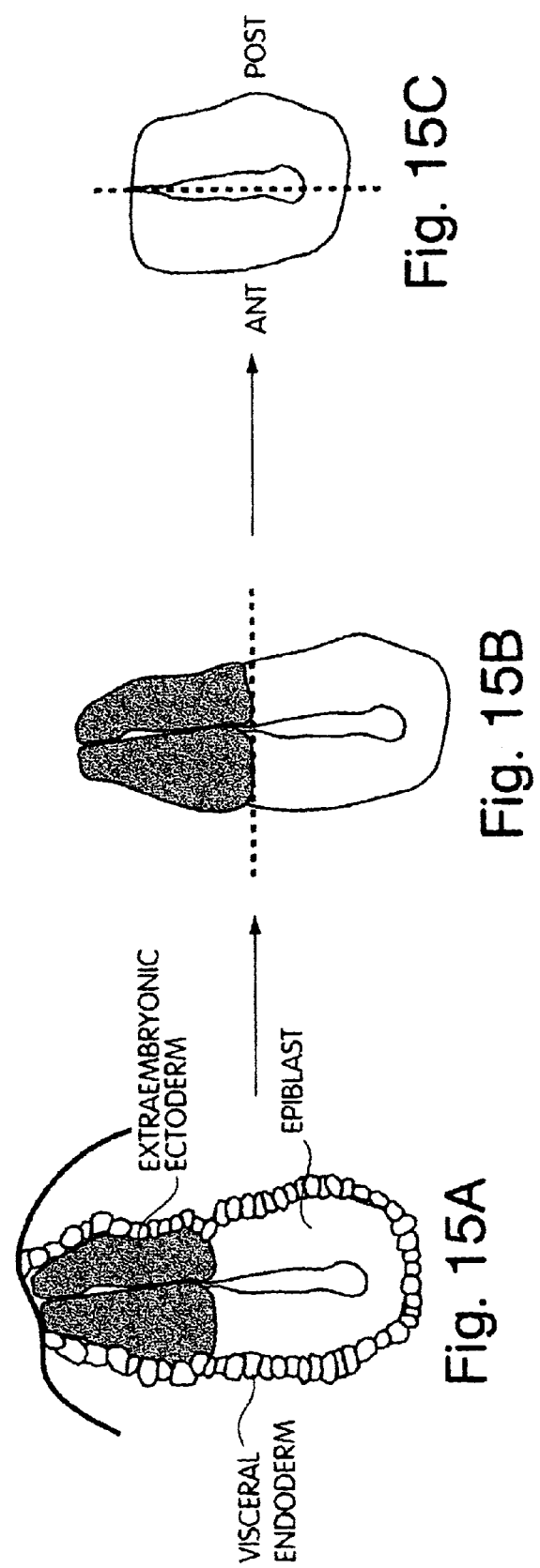

| RESCUE OF NULL MUTANT PHENOTYPE BY BMP-4 | | | |
|---|---|---|---|
| | # CONTAINING HEMOGLOBIN | TOTAL # EBs | PERCENT HEMOGLOBINIZED |
| WT PARENTAL | 225 | 260 | 86.5 |
| MUTANT ( - BMP-4) | 2 | 50 | 4.0 |
| MUTANT ( + BMP-4) | 42 | 72 | 58.5 |

A wt

B mut (-BMP-4)

C wt

D mut (+BMP-4)

Fig. 17

SEQUENCE LISTING

<160> NUMBER OF SEQ ID NOS: 42

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
atggatccag cacacatta                                                19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 2
tcgccattca ggctgcg                                                  17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
cagcactagg cctactacag                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
tcaaggtgtc caagaacgtg                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
tgctgcctgt gagtcataac                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
ctactctaag gcaacaagcc                                               20

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 7
aggagctgag tcgccacctc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
gtagcccacg gagggatgca                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
gttacctctg ggatcccttc                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
gaggtgacca atgcaataag                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
tgcgatggtg tataacgtca                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
gcttggcagc gaaacactaa                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
```
ccataccgcc tctgtgactt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
acacgatgcc atgctggtca                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
ctcgcagaac agcagcctaa                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
agggtctgct ggagaggtta                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
ggaaaaaacc ctcatcaatg                                              20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
attcatgtgc agagaggagg cata                                         24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
cgactagttc gggacatccg                                              20

<210> SEQ ID NO 20
<211> LENGTH: 26
<212> TYPE: DNA
<213> ORGANISM: Artificial Sequence

```
<220> FEATURE:
<223> OTHER INFORMATION: Description of Artificial Sequence: Primer

<400> SEQUENCE: 20
atggtaccgt acatattcct ctggtg                                           26

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 21
cgactagtgg cggtctgagg agac                                             24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 22
atggtaccac gcacaggtca cgt                                              23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
cagggaagag agcagactga                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
agctgatgca gctgatccag                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 25
ctgctgctat ccatcagcgt                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
aagaaggata agaggacagg                                                  20
```

-continued

```
<210> SEQ ID NO 27
<211> LENGTH: 1278
<212> TYPE: DNA
<213> ORGANISM: Gallus gallus
<220> FEATURE:
<221> NAME/KEY: CDS
<222> LOCATION: (1)..(1275)

<400> SEQUENCE: 27 atg gtc gaa atg ctg ctg ttg aca aga att ctc ttg gtg ggc ttc atc         48
Met Val Glu Met Leu Leu Leu Thr Arg Ile Leu Leu Val Gly Phe Ile
 1               5                  10                  15 tgc gct ctt tta gtc tcc tct ggg ctg act tgt gga cca ggc agg ggc         96
Cys Ala Leu Leu Val Ser Ser Gly Leu Thr Cys Gly Pro Gly Arg Gly
             20                  25                  30 att gga aaa agg agg cac ccc aaa aag ctg acc ccg tta gcc tat aag        144
Ile Gly Lys Arg Arg His Pro Lys Lys Leu Thr Pro Leu Ala Tyr Lys
         35                  40                  45 cag ttt att ccc aat gtg gca gag aag acc cta ggg gcc agt gga aga        192
Gln Phe Ile Pro Asn Val Ala Glu Lys Thr Leu Gly Ala Ser Gly Arg
     50                  55                  60 tat gaa ggg aag atc aca aga aac tcc gag aga ttt aaa gaa cta acc        240
Tyr Glu Gly Lys Ile Thr Arg Asn Ser Glu Arg Phe Lys Glu Leu Thr
 65                  70                  75                  80 cca aat tac aac cct gac att att ttt aag gat gaa gag aac acg gga        288
Pro Asn Tyr Asn Pro Asp Ile Ile Phe Lys Asp Glu Glu Asn Thr Gly
                 85                  90                  95 gct gac aga ctg atg act cag cgc tgc aag gac aag ctg aat gcc ctg        336
Ala Asp Arg Leu Met Thr Gln Arg Cys Lys Asp Lys Leu Asn Ala Leu
            100                 105                 110 gcg atc tcg gtg atg aac cag tgg ccc ggg gtg aag ctg cgg gtg acc        384
Ala Ile Ser Val Met Asn Gln Trp Pro Gly Val Lys Leu Arg Val Thr
        115                 120                 125 gag ggc tgg gac gag gat ggc cat cac tcc gag gaa tcg ctg cac tac        432
Glu Gly Trp Asp Glu Asp Gly His His Ser Glu Glu Ser Leu His Tyr
    130                 135                 140 gag ggt cgc gcc gtg gac atc acc acg tcg gat cgg gac cgc agc aag        480
Glu Gly Arg Ala Val Asp Ile Thr Thr Ser Asp Arg Asp Arg Ser Lys
145                 150                 155                 160 tac gga atg ctg gcc cgc ctc gcc gtc gag gcc ggc ttc gac tgg gtc        528
Tyr Gly Met Leu Ala Arg Leu Ala Val Glu Ala Gly Phe Asp Trp Val
                165                 170                 175 tac tac gag tcc aag gcg cac atc cac tgc tcc gtc aaa gca gaa aac        576
Tyr Tyr Glu Ser Lys Ala His Ile His Cys Ser Val Lys Ala Glu Asn
            180                 185                 190 tca gtg gca gcg aaa tca gga ggc tgc ttc cct ggc tca gcc aca gtg        624
Ser Val Ala Ala Lys Ser Gly Gly Cys Phe Pro Gly Ser Ala Thr Val
        195                 200                 205 cac ctg gag cat gga ggc acc aag ctg gtg aag gac ctg agc cct ggg        672
His Leu Glu His Gly Gly Thr Lys Leu Val Lys Asp Leu Ser Pro Gly
    210                 215                 220 gac cgc gtg ctg gct gct gac gcg gac ggc cgg ctg ctc tac agt gac        720
Asp Arg Val Leu Ala Ala Asp Ala Asp Gly Arg Leu Leu Tyr Ser Asp
225                 230                 235                 240 ttc ctc acc ttc ctc gac cgg atg gac agc tcc cga aag ctc ttc tac        768
Phe Leu Thr Phe Leu Asp Arg Met Asp Ser Ser Arg Lys Leu Phe Tyr
                245                 250                 255 gtc atc gag acg cgg cag ccc cgg gcc cgg ctg cta ctg acg gcg gcc        816
Val Ile Glu Thr Arg Gln Pro Arg Ala Arg Leu Leu Leu Thr Ala Ala
            260                 265                 270
```

-continued

```
cac ctg ctc ttt gtg gcc ccc cag cac aac cag tcg gag gcc aca ggg       864
His Leu Leu Phe Val Ala Pro Gln His Asn Gln Ser Glu Ala Thr Gly
            275                 280                 285 tcc acc agt ggc cag gcg ctc ttc gcc agc aac gtg aag cct ggc caa       912
Ser Thr Ser Gly Gln Ala Leu Phe Ala Ser Asn Val Lys Pro Gly Gln
        290                 295                 300 cgt gtc tat gtg ctg ggc gag ggc ggg cag cag ctg ctg ccg gcg tct       960
Arg Val Tyr Val Leu Gly Glu Gly Gly Gln Gln Leu Leu Pro Ala Ser
305                 310                 315                 320 gtc cac agc gtc tca ttg cgg gag gag gcg tcc gga gcc tac gcc cca      1008
Val His Ser Val Ser Leu Arg Glu Glu Ala Ser Gly Ala Tyr Ala Pro
            325                 330                 335 ctc acc gcc cag ggc acc atc ctc atc aac cgg gtg ttg gcc tcc tgc      1056
Leu Thr Ala Gln Gly Thr Ile Leu Ile Asn Arg Val Leu Ala Ser Cys
        340                 345                 350 tac gcc gtc atc gag gag cac agt tgg gcc cat tgg gcc ttc gca cca      1104
Tyr Ala Val Ile Glu Glu His Ser Trp Ala His Trp Ala Phe Ala Pro
    355                 360                 365 ttc cgc ttg gct cag ggg ctg ctg gcc gcc ctc tgc cca gat ggg gcc      1152
Phe Arg Leu Ala Gln Gly Leu Leu Ala Ala Leu Cys Pro Asp Gly Ala
370                 375                 380 atc cct act gcc gcc acc acc acc act ggc atc cat tgg tac tca cgg      1200
Ile Pro Thr Ala Ala Thr Thr Thr Thr Gly Ile His Trp Tyr Ser Arg
385                 390                 395                 400 ctc ctc tac cgc atc ggc agc tgg gtg ctg gat ggt gac gcg ctg cat      1248
Leu Leu Tyr Arg Ile Gly Ser Trp Val Leu Asp Gly Asp Ala Leu His
            405                 410                 415 ccg ctg ggc atg gtg gca ccg gcc agc tga                              1278
Pro Leu Gly Met Val Ala Pro Ala Ser
        420                 425

<210> SEQ ID NO 28
<211> LENGTH: 1191
<212> TYPE: DNA
<213> ORGANISM: Mus musculus
<220> FEATURE:
<221> NAME/KEY: CDS
<222> LOCATION: (1)..(1188)

<400> SEQUENCE: 28 atg gct ctg ccg gcc agt ctg ttg ccc ctg tgc tgc ttg gca ctc ttg        48
Met Ala Leu Pro Ala Ser Leu Leu Pro Leu Cys Cys Leu Ala Leu Leu
1               5                   10                  15 gca cta tct gcc cag agc tgc ggg ccg ggc cga gga ccg gtt ggc cgg        96
Ala Leu Ser Ala Gln Ser Cys Gly Pro Gly Arg Gly Pro Val Gly Arg
            20                  25                  30 cgg cgt tat gtg cgc aag caa ctt gtg cct ctg cta tac aag cag ttt       144
Arg Arg Tyr Val Arg Lys Gln Leu Val Pro Leu Leu Tyr Lys Gln Phe
        35                  40                  45 gtg ccc agt atg ccc gag cgg acc ctg ggc gcg agt ggg cca gcg gag       192
Val Pro Ser Met Pro Glu Arg Thr Leu Gly Ala Ser Gly Pro Ala Glu
    50                  55                  60 ggg agg gta aca agg ggg tcg gag cgc ttc cgg gac ctc gta ccc aac       240
Gly Arg Val Thr Arg Gly Ser Glu Arg Phe Arg Asp Leu Val Pro Asn
65                  70                  75                  80 tac aac ccc gac ata atc ttc aag gat gag gag aac agc ggc gca gac       288
Tyr Asn Pro Asp Ile Ile Phe Lys Asp Glu Glu Asn Ser Gly Ala Asp
            85                  90                  95 cgc ctg atg aca gag cgt tgc aaa gag cgg gtg aac gct cta gcc atc       336
Arg Leu Met Thr Glu Arg Cys Lys Glu Arg Val Asn Ala Leu Ala Ile
        100                 105                 110
```

-continued

```
gcg gtg atg aac atg tgg ccc gga gta cgc cta cgt gtg act gaa ggc      384
Ala Val Met Asn Met Trp Pro Gly Val Arg Leu Arg Val Thr Glu Gly
        115                 120                 125 tgg gac gag gac ggc cac cac gca cag gat tca ctc cac tac gaa ggc      432
Trp Asp Glu Asp Gly His His Ala Gln Asp Ser Leu His Tyr Glu Gly
130                 135                 140 cgt gcc ttg gac atc acc acg tct gac cgt gac cgt aat aag tat ggt      480
Arg Ala Leu Asp Ile Thr Thr Ser Asp Arg Asp Arg Asn Lys Tyr Gly
145                 150                 155                 160 ttg ttg gcg cgc cta gct gtg gaa gcc gga ttc gac tgg gtc tac tac      528
Leu Leu Ala Arg Leu Ala Val Glu Ala Gly Phe Asp Trp Val Tyr Tyr
                165                 170                 175 gag tcc cgc aac cac atc cac gta tcg gtc aaa gct gat aac tca ctg      576
Glu Ser Arg Asn His Ile His Val Ser Val Lys Ala Asp Asn Ser Leu
            180                 185                 190 gcg gtc cga gcc gga ggc tgc ttt ccg gga aat gcc acg gtg cgc ttg      624
Ala Val Arg Ala Gly Gly Cys Phe Pro Gly Asn Ala Thr Val Arg Leu
        195                 200                 205 cgg agc ggc gaa cgg aag ggg ctg agg gaa cta cat cgt ggt gac tgg      672
Arg Ser Gly Glu Arg Lys Gly Leu Arg Glu Leu His Arg Gly Asp Trp
    210                 215                 220 gta ctg gcc gct gat gca gcg ggc cga gtg gta ccc acg cca gtg ctg      720
Val Leu Ala Ala Asp Ala Ala Gly Arg Val Val Pro Thr Pro Val Leu
225                 230                 235                 240 ctc ttc ctg gac cgg gat ctg cag cgc cgc gcc tcg ttc gtg gct gtg      768
Leu Phe Leu Asp Arg Asp Leu Gln Arg Arg Ala Ser Phe Val Ala Val
                245                 250                 255 gag acc gag cgg cct ccg cgc aaa ctg ttg ctc aca ccc tgg cat ctg      816
Glu Thr Glu Arg Pro Pro Arg Lys Leu Leu Leu Thr Pro Trp His Leu
            260                 265                 270 gtg ttc gct gct cgc ggg cca gcg cct gct cca ggt gac ttt gca ccg      864
Val Phe Ala Ala Arg Gly Pro Ala Pro Ala Pro Gly Asp Phe Ala Pro
        275                 280                 285 gtg ttc gcg cgc cgc tta cgt gct ggc gac tcg gtg ctg gct ccc ggc      912
Val Phe Ala Arg Arg Leu Arg Ala Gly Asp Ser Val Leu Ala Pro Gly
    290                 295                 300 ggg gac gcg ctc cag ccg gcg cgc gta gcc cgc gtg gcg cgc gag gaa      960
Gly Asp Ala Leu Gln Pro Ala Arg Val Ala Arg Val Ala Arg Glu Glu
305                 310                 315                 320 gcc gtg ggc gtg ttc gca ccg ctc act gcg cac ggg acg ctg ctg gtc     1008
Ala Val Gly Val Phe Ala Pro Leu Thr Ala His Gly Thr Leu Leu Val
                325                 330                 335 aac gac gtc ctc gcc tcc tgc tac gcg gtt cta gag agt cac cag tgg     1056
Asn Asp Val Leu Ala Ser Cys Tyr Ala Val Leu Glu Ser His Gln Trp
            340                 345                 350 gcc cac cgc gcc ttc gcc cct ttg cgg ctg ctg cac gcg ctc ggg gct     1104
Ala His Arg Ala Phe Ala Pro Leu Arg Leu Leu His Ala Leu Gly Ala
        355                 360                 365 ctg ctc cct ggg ggt gca gtc cag ccg act ggc atg cat tgg tac tct     1152
Leu Leu Pro Gly Gly Ala Val Gln Pro Thr Gly Met His Trp Tyr Ser
    370                 375                 380 cgc ctc ctt tac cgc ttg gcc gag gag tta atg ggc tga                 1191
Arg Leu Leu Tyr Arg Leu Ala Glu Glu Leu Met Gly
385                 390                 395

<210> SEQ ID NO 29
<211> LENGTH: 1056
<212> TYPE: DNA
<213> ORGANISM: Mus musculus
<220> FEATURE:
<221> NAME/KEY: CDS
```

<222> LOCATION: (1)..(1008)

<400> SEQUENCE: 29

```
gag cgc ttc aaa gag ctc acc ccc aac tac aat ccc gac atc atc ttc      48
Glu Arg Phe Lys Glu Leu Thr Pro Asn Tyr Asn Pro Asp Ile Ile Phe
 1               5                  10                  15 aag gac gag gag aac acg ggt gcc gac cgc ctc atg acc cag cgc tgc      96
Lys Asp Glu Glu Asn Thr Gly Ala Asp Arg Leu Met Thr Gln Arg Cys
             20                  25                  30 aag gac cgt ctg aac tca ctg gcc atc tct gtc atg aac cag tgg cct     144
Lys Asp Arg Leu Asn Ser Leu Ala Ile Ser Val Met Asn Gln Trp Pro
         35                  40                  45 ggt gtg aaa ctg cgg gtg acc gaa ggc tgg gat gaa gat ggc cat cac     192
Gly Val Lys Leu Arg Val Thr Glu Gly Trp Asp Glu Asp Gly His His
     50                  55                  60 tca gag gag tct tta cac tat gag ggc cgc gcg gtg gat atc acc acc     240
Ser Glu Glu Ser Leu His Tyr Glu Gly Arg Ala Val Asp Ile Thr Thr
 65                  70                  75                  80 tca gac cgt gac cga aat aag tat gga ctg ctg gcg cgc tta gca gtg     288
Ser Asp Arg Asp Arg Asn Lys Tyr Gly Leu Leu Ala Arg Leu Ala Val
                 85                  90                  95 gag gcc ggc ttc gac tgg gtg tat tac gag tcc aag gcc cac gtg cat     336
Glu Ala Gly Phe Asp Trp Val Tyr Tyr Glu Ser Lys Ala His Val His
            100                 105                 110 tgc tct gtc aag tct gag cat tcg gcc gct gcc aag aca ggt ggc tgc     384
Cys Ser Val Lys Ser Glu His Ser Ala Ala Ala Lys Thr Gly Gly Cys
        115                 120                 125 ttt cct gcc gga gcc cag gtg cgc cta gag aac ggg gag cgt gtg gcc     432
Phe Pro Ala Gly Ala Gln Val Arg Leu Glu Asn Gly Glu Arg Val Ala
    130                 135                 140 ctg tca gct gta aag cca gga gac cgg gtg ctg gcc atg ggg gag gat     480
Leu Ser Ala Val Lys Pro Gly Asp Arg Val Leu Ala Met Gly Glu Asp
145                 150                 155                 160 ggg acc ccc acc ttc agt gat gtg ctt att ttc ctg gac cgc gag cca     528
Gly Thr Pro Thr Phe Ser Asp Val Leu Ile Phe Leu Asp Arg Glu Pro
                165                 170                 175 aac cgg ctg aga gct ttc cag gtc atc gag act cag gat cct ccg cgt     576
Asn Arg Leu Arg Ala Phe Gln Val Ile Glu Thr Gln Asp Pro Pro Arg
            180                 185                 190 cgg ctg gcg ctc acg cct gcc cac ctg ctc ttc att gcg gac aat cat     624
Arg Leu Ala Leu Thr Pro Ala His Leu Leu Phe Ile Ala Asp Asn His
        195                 200                 205 aca gaa cca gca gcc cac ttc cgg gcc aca ttt gcc agc cat gtg caa     672
Thr Glu Pro Ala Ala His Phe Arg Ala Thr Phe Ala Ser His Val Gln
    210                 215                 220 cca ggc caa tat gtg ctg gta tca ggg gta cca ggc tca cag cct gct     720
Pro Gly Gln Tyr Val Leu Val Ser Gly Val Pro Gly Ser Gln Pro Ala
225                 230                 235                 240 cgg gtg gca gct gtc tcc acc cac gtg gcc ctt ggg tcc tat gct cct     768
Arg Val Ala Ala Val Ser Thr His Val Ala Leu Gly Ser Tyr Ala Pro
                245                 250                 255 ctc aca agg cat ggg aca ctt gtg gtg gag gat gtg gtg gcc tcc tgc     816
Leu Thr Arg His Gly Thr Leu Val Val Glu Asp Val Val Ala Ser Cys
            260                 265                 270 ttt gca gct gtg gct gac cac cat ctg gct cag ttg gcc ttc tgg ccc     864
Phe Ala Ala Val Ala Asp His His Leu Ala Gln Leu Ala Phe Trp Pro
        275                 280                 285 ctg cga ctg ttt ccc agt ttg gca tgg ggc agc tgg acc cca agt gag     912
Leu Arg Leu Phe Pro Ser Leu Ala Trp Gly Ser Trp Thr Pro Ser Glu
    290                 295                 300
```

-continued

```
ggt gtt cac tgg tac cct cag atg ctc tac cgc ctg ggg cgt ctc ttg      960
Gly Val His Trp Tyr Pro Gln Met Leu Tyr Arg Leu Gly Arg Leu Leu
305                 310                 315                 320 cta gaa gag agc acc ttc cat cca ctg ggc atg tct ggg gca gga agc     1008
Leu Glu Glu Ser Thr Phe His Pro Leu Gly Met Ser Gly Ala Gly Ser
                325                 330                 335 tgaagggact ctaaccactg ccctcctgga actgctgtgc gtggatcc                1056

<210> SEQ ID NO 30
<211> LENGTH: 1314
<212> TYPE: DNA
<213> ORGANISM: Mus musculus
<220> FEATURE:
<221> NAME/KEY: CDS
<222> LOCATION: (1)..(1311)

<400> SEQUENCE: 30 atg ctg ctg ctg ctg gcc aga tgt ttt ctg gtg atc ctt gct tcc tcg       48
Met Leu Leu Leu Leu Ala Arg Cys Phe Leu Val Ile Leu Ala Ser Ser
  1               5                  10                  15 ctg ctg gtg tgc ccc ggg ctg gcc tgt ggg ccc ggc agg ggg ttt gga       96
Leu Leu Val Cys Pro Gly Leu Ala Cys Gly Pro Gly Arg Gly Phe Gly
             20                  25                  30 aag agg cgg cac ccc aaa aag ctg acc cct tta gcc tac aag cag ttt      144
Lys Arg Arg His Pro Lys Lys Leu Thr Pro Leu Ala Tyr Lys Gln Phe
         35                  40                  45 att ccc aac gta gcc gag aag acc cta ggg gcc agc ggc aga tat gaa      192
Ile Pro Asn Val Ala Glu Lys Thr Leu Gly Ala Ser Gly Arg Tyr Glu
     50                  55                  60 ggg aag atc aca aga aac tcc gaa cga ttt aag gaa ctc acc ccc aat      240
Gly Lys Ile Thr Arg Asn Ser Glu Arg Phe Lys Glu Leu Thr Pro Asn
 65                  70                  75                  80 tac aac ccc gac atc ata ttt aag gat gag gaa aac acg gga gca gac      288
Tyr Asn Pro Asp Ile Ile Phe Lys Asp Glu Glu Asn Thr Gly Ala Asp
                 85                  90                  95 cgg ctg atg act cag agg tgc aaa gac aag tta aat gcc ttg gcc atc      336
Arg Leu Met Thr Gln Arg Cys Lys Asp Lys Leu Asn Ala Leu Ala Ile
            100                 105                 110 tct gtg atg aac cag tgg cct gga gtg aag ctg cga gtg acc gag ggc      384
Ser Val Met Asn Gln Trp Pro Gly Val Lys Leu Arg Val Thr Glu Gly
        115                 120                 125 tgg gat gag gac ggc cat cat tca gag gag tct cta cac tat gag ggt      432
Trp Asp Glu Asp Gly His His Ser Glu Glu Ser Leu His Tyr Glu Gly
    130                 135                 140 cga gca gtg gac atc acc acg tcc gac cgg gac cgc agc aag tac ggc      480
Arg Ala Val Asp Ile Thr Thr Ser Asp Arg Asp Arg Ser Lys Tyr Gly
145                 150                 155                 160 atg ctg gct cgc ctg gct gtg gaa gca ggt ttc gac tgg gtc tac tat      528
Met Leu Ala Arg Leu Ala Val Glu Ala Gly Phe Asp Trp Val Tyr Tyr
                165                 170                 175 gaa tcc aaa gct cac atc cac tgt tct gtg aaa gca gag aac tcc gtg      576
Glu Ser Lys Ala His Ile His Cys Ser Val Lys Ala Glu Asn Ser Val
            180                 185                 190 gcg gcc aaa tcc ggc ggc tgt ttc ccg gga tcc gcc acc gtg cac ctg      624
Ala Ala Lys Ser Gly Gly Cys Phe Pro Gly Ser Ala Thr Val His Leu
        195                 200                 205 gag cag ggc ggc acc aag ctg gtg aag gac tta cgt ccc gga gac cgc      672
Glu Gln Gly Gly Thr Lys Leu Val Lys Asp Leu Arg Pro Gly Asp Arg
    210                 215                 220 gtg ctg gcg gct gac gac cag ggc cgg ctg ctg tac agc gac ttc ctc      720
Val Leu Ala Ala Asp Asp Gln Gly Arg Leu Leu Tyr Ser Asp Phe Leu
```

```
Val Leu Ala Ala Asp Asp Gln Gly Arg Leu Leu Tyr Ser Asp Phe Leu
225                 230                 235                 240 acc ttc ctg gac cgc gac gaa ggc gcc aag aag gtc ttc tac gtg atc        768
Thr Phe Leu Asp Arg Asp Glu Gly Ala Lys Lys Val Phe Tyr Val Ile
                245                 250                 255 gag acg ctg gag ccg cgc gag cgc ctg ctc acc gcc gcg cac ctg            816
Glu Thr Leu Glu Pro Arg Glu Arg Leu Leu Thr Ala Ala His Leu
        260                 265                 270 ctc ttc gtg gcg ccg cac aac gac tcg ggc ccc acg ccc ggg cca agc        864
Leu Phe Val Ala Pro His Asn Asp Ser Gly Pro Thr Pro Gly Pro Ser
    275                 280                 285 gcg ctc ttt gcc agc cgc gtg cgc ccc ggg cag cgc gtg tac gtg gtg        912
Ala Leu Phe Ala Ser Arg Val Arg Pro Gly Gln Arg Val Tyr Val Val
290                 295                 300 gct gaa cgc ggc ggg gac cgc cgg ctg ctg ccc gcc gcg gtg cac agc        960
Ala Glu Arg Gly Gly Asp Arg Arg Leu Leu Pro Ala Ala Val His Ser
305                 310                 315                 320 gtg acg ctg cga gag gag gag gcg ggc gcg tac gcg ccg ctc acg gcg        1008
Val Thr Leu Arg Glu Glu Glu Ala Gly Ala Tyr Ala Pro Leu Thr Ala
                325                 330                 335 cac ggc acc att ctc atc aac cgg gtg ctc gcc tcg tgc tac gct gtc        1056
His Gly Thr Ile Leu Ile Asn Arg Val Leu Ala Ser Cys Tyr Ala Val
            340                 345                 350 atc gag gag cac agc tgg gca cac cgg gcc ttc gcg cct ttc cgc ctg        1104
Ile Glu Glu His Ser Trp Ala His Arg Ala Phe Ala Pro Phe Arg Leu
        355                 360                 365 gcg cac gcg ctg ctg gcc gcg ctg gca ccc gcc cgc acg gac ggc ggg        1152
Ala His Ala Leu Leu Ala Ala Leu Ala Pro Ala Arg Thr Asp Gly Gly
    370                 375                 380 ggc ggg ggc agc atc cct gca gcg caa tct gca acg gaa gcg agg ggc        1200
Gly Gly Gly Ser Ile Pro Ala Ala Gln Ser Ala Thr Glu Ala Arg Gly
385                 390                 395                 400 gcg gag ccg act gcg ggc atc cac tgg tac tcg cag ctg ctc tac cac        1248
Ala Glu Pro Thr Ala Gly Ile His Trp Tyr Ser Gln Leu Leu Tyr His
                405                 410                 415 att ggc acc tgg ctg ttg gac agc gag acc atg cat ccc ttg gga atg        1296
Ile Gly Thr Trp Leu Leu Asp Ser Glu Thr Met His Pro Leu Gly Met
            420                 425                 430 gcg gtc aag tcc agc tga                                                1314
Ala Val Lys Ser Ser
        435

<210> SEQ ID NO 31
<211> LENGTH: 1257
<212> TYPE: DNA
<213> ORGANISM: Brachydanio rerio
<220> FEATURE:
<221> NAME/KEY: CDS
<222> LOCATION: (1)..(1254)

<400> SEQUENCE: 31 atg cgg ctt ttg acg aga gtg ctg ctg gtg tct ctt ctc act ctg tcc        48
Met Arg Leu Leu Thr Arg Val Leu Leu Val Ser Leu Leu Thr Leu Ser
1               5                   10                  15 ttg gtg gtg tcc gga ctg gcc tgc ggt cct ggc aga ggc tac ggc aga        96
Leu Val Val Ser Gly Leu Ala Cys Gly Pro Gly Arg Gly Tyr Gly Arg
            20                  25                  30 aga aga cat ccg aag aag ctg aca cct ctc gcc tac aag cag ttc ata        144
Arg Arg His Pro Lys Lys Leu Thr Pro Leu Ala Tyr Lys Gln Phe Ile
        35                  40                  45 cct aat gtc gcg gag aag acc tta ggg gcc agc ggc aga tac gag ggc        192
```

```
Pro Asn Val Ala Glu Lys Thr Leu Gly Ala Ser Gly Arg Tyr Glu Gly
     50                  55                  60 aag ata acg cgc aat tcg gag aga ttt aaa gaa ctt act cca aat tac      240
Lys Ile Thr Arg Asn Ser Glu Arg Phe Lys Glu Leu Thr Pro Asn Tyr
 65                  70                  75                  80 aat ccc gac att atc ttt aag gat gag gag aac acg gga gcg gac agg      288
Asn Pro Asp Ile Ile Phe Lys Asp Glu Glu Asn Thr Gly Ala Asp Arg
                     85                  90                  95 ctc atg aca cag aga tgc aaa gac aag ctg aac tcg ctg gcc atc tct      336
Leu Met Thr Gln Arg Cys Lys Asp Lys Leu Asn Ser Leu Ala Ile Ser
                100                 105                 110 gta atg aac cac tgg cca ggg gtt aag ctg cgt gtg aca gag ggc tgg      384
Val Met Asn His Trp Pro Gly Val Lys Leu Arg Val Thr Glu Gly Trp
            115                 120                 125 gat gag gac ggt cac cat ttt gaa gaa tca ctc cac tac gag gga aga      432
Asp Glu Asp Gly His His Phe Glu Glu Ser Leu His Tyr Glu Gly Arg
        130                 135                 140 gct gtt gat att acc acc tct gac cga gac aag agc aaa tac ggg aca      480
Ala Val Asp Ile Thr Thr Ser Asp Arg Asp Lys Ser Lys Tyr Gly Thr
145                 150                 155                 160 ctg tct cgc cta gct gtg gag gct gga ttt gac tgg gtc tat tac gag      528
Leu Ser Arg Leu Ala Val Glu Ala Gly Phe Asp Trp Val Tyr Tyr Glu
                165                 170                 175 tcc aaa gcc cac att cat tgc tct gtc aaa gca gaa aat tcg gtt gct      576
Ser Lys Ala His Ile His Cys Ser Val Lys Ala Glu Asn Ser Val Ala
                180                 185                 190 gcg aaa tct ggg ggc tgt ttc cca ggt tcg gct ctg gtc tcg ctc cag      624
Ala Lys Ser Gly Gly Cys Phe Pro Gly Ser Ala Leu Val Ser Leu Gln
                195                 200                 205 gac gga gga cag aag gcc gtg aag gac ctg aac ccc gga gac aag gtg      672
Asp Gly Gly Gln Lys Ala Val Lys Asp Leu Asn Pro Gly Asp Lys Val
        210                 215                 220 ctg gcg gca gac agc gcg gga aac ctg gtg ttc agc gac ttc atc atg      720
Leu Ala Ala Asp Ser Ala Gly Asn Leu Val Phe Ser Asp Phe Ile Met
225                 230                 235                 240 ttc aca gac cga gac tcc acg acg cga cgt gtg ttt tac gtc ata gaa      768
Phe Thr Asp Arg Asp Ser Thr Thr Arg Arg Val Phe Tyr Val Ile Glu
                245                 250                 255 acg caa gaa ccc gtt gaa aag atc acc ctc acc gcc gct cac ctc ctt      816
Thr Gln Glu Pro Val Glu Lys Ile Thr Leu Thr Ala Ala His Leu Leu
                260                 265                 270 ttt gtc ctc gac aac tca acg gaa gat ctc cac acc atg acc gcc gcg      864
Phe Val Leu Asp Asn Ser Thr Glu Asp Leu His Thr Met Thr Ala Ala
                275                 280                 285 tat gcc agc agt gtc aga gcc gga caa aag gtg atg gtt gtt gat gat      912
Tyr Ala Ser Ser Val Arg Ala Gly Gln Lys Val Met Val Val Asp Asp
        290                 295                 300 agc ggt cag ctt aaa tct gtc atc gtg cag cgg ata tac acg gag gag      960
Ser Gly Gln Leu Lys Ser Val Ile Val Gln Arg Ile Tyr Thr Glu Glu
305                 310                 315                 320 cag cgg ggc tcg ttc gca cca gtg act gca cat ggg acc att gtg gtc     1008
Gln Arg Gly Ser Phe Ala Pro Val Thr Ala His Gly Thr Ile Val Val
                325                 330                 335 gac aga ata ctg gcg tcc tgt tac gcc gta ata gag gac cag ggg ctt     1056
Asp Arg Ile Leu Ala Ser Cys Tyr Ala Val Ile Glu Asp Gln Gly Leu
                340                 345                 350 gcg cat ttg gcc ttc gcg ccc gcc agg ctc tat tat tac gtg tca tca     1104
Ala His Leu Ala Phe Ala Pro Ala Arg Leu Tyr Tyr Tyr Val Ser Ser
        355                 360                 365
```

| | |
|---|---|
| ttc ctg ttc ccc caa aac tcc agc agt cgg tcc aat gcg act tta caa<br>Phe Leu Phe Pro Gln Asn Ser Ser Ser Arg Ser Asn Ala Thr Leu Gln<br>370                       375                     380 | 1152 |
| cag gag ggg gtc cac tgg tac tcc agg ctc ctg tat caa atg gga acg<br>Gln Glu Gly Val His Trp Tyr Ser Arg Leu Leu Tyr Gln Met Gly Thr<br>385                       390                     395                     400 | 1200 |
| tgg ctt ttg gac agc aac atg ctt cat cct ttg ggg atg tca gta aac<br>Trp Leu Leu Asp Ser Asn Met Leu His Pro Leu Gly Met Ser Val Asn<br>                     405                     410                     415 | 1248 |
| tca agc tga<br>Ser Ser | 1257 |

<210> SEQ ID NO 32
<211> LENGTH: 1425
<212> TYPE: DNA
<213> ORGANISM: Homo sapiens
<220> FEATURE:
<221> NAME/KEY: CDS
<222> LOCATION: (1)..(1425)
<221> NAME/KEY: Modified_base
<222> LOCATION: (1387...1389)
<223> OTHER INFORMATION: n=a, c, g, or t
<221> NAME/KEY: SITE
<222> LOCATION: (463)
<223> OTHER INFORMATION: Xaa=unknown amino acid

<400> SEQUENCE: 32

| | |
|---|---|
| atg ctg ctg ctg gcg aga tgt ctg ctg cta gtc ctc gtc tcc tcg ctg<br>Met Leu Leu Leu Ala Arg Cys Leu Leu Leu Val Leu Val Ser Ser Leu<br>1                     5                      10                   15 | 48 |
| ctg gta tgc tcg gga ctg gcg tgc gga ccg ggc agg ggg ttc ggg aag<br>Leu Val Cys Ser Gly Leu Ala Cys Gly Pro Gly Arg Gly Phe Gly Lys<br>                   20                     25                     30 | 96 |
| agg agg cac ccc aaa aag ctg acc cct tta gcc tac aag cag ttt atc<br>Arg Arg His Pro Lys Lys Leu Thr Pro Leu Ala Tyr Lys Gln Phe Ile<br>               35                     40                     45 | 144 |
| ccc aat gtg gcc gag aag acc cta ggc gcc agc gga agg tat gaa ggg<br>Pro Asn Val Ala Glu Lys Thr Leu Gly Ala Ser Gly Arg Tyr Glu Gly<br>50                      55                     60 | 192 |
| aag atc tcc aga aac tcc gag cga ttt aag gaa ctc acc ccc aat tac<br>Lys Ile Ser Arg Asn Ser Glu Arg Phe Lys Glu Leu Thr Pro Asn Tyr<br>65                      70                     75                     80 | 240 |
| aac ccc gac atc ata ttt aag gat gaa gaa aac acc gga gcg gac agg<br>Asn Pro Asp Ile Ile Phe Lys Asp Glu Glu Asn Thr Gly Ala Asp Arg<br>                   85                     90                     95 | 288 |
| ctg atg act cag agg tgt aag gac aag ttg aac gct ttg gcc atc tcg<br>Leu Met Thr Gln Arg Cys Lys Asp Lys Leu Asn Ala Leu Ala Ile Ser<br>               100                   105                  110 | 336 |
| gtg atg aac cag tgg cca gga gtg aaa ctg cgg gtg acc gag ggc tgg<br>Val Met Asn Gln Trp Pro Gly Val Lys Leu Arg Val Thr Glu Gly Trp<br>               115                   120                  125 | 384 |
| gac gaa gat ggc cac cac tca gag gag tct ctg cac tac gag ggc cgc<br>Asp Glu Asp Gly His His Ser Glu Glu Ser Leu His Tyr Glu Gly Arg<br>130                      135                     140 | 432 |
| gca gtg gac atc acc acg tct gac cgc gac cgc agc aag tac ggc atg<br>Ala Val Asp Ile Thr Thr Ser Asp Arg Asp Arg Ser Lys Tyr Gly Met<br>145                      150                     155                  160 | 480 |
| ctg gcc cgc ctg gcg gtg gag gcc ggc ttc gac tgg gtg tac tac gag<br>Leu Ala Arg Leu Ala Val Glu Ala Gly Phe Asp Trp Val Tyr Tyr Glu<br>                   165                   170                  175 | 528 |
| tcc aag gca cat atc cac tgc tcg gtg aaa gca gag aac tcg gtg gcg<br>Ser Lys Ala His Ile His Cys Ser Val Lys Ala Glu Asn Ser Val Ala<br>               180                   185                  190 | 576 |

```
gcc aaa tcg gga ggc tgc ttc ccg ggc tcg gcc acg gtg cac ctg gag         624
Ala Lys Ser Gly Gly Cys Phe Pro Gly Ser Ala Thr Val His Leu Glu
        195                 200                 205 cag ggc ggc acc aag ctg gtg aag gac ctg agc ccc ggg gac cgc gtg         672
Gln Gly Gly Thr Lys Leu Val Lys Asp Leu Ser Pro Gly Asp Arg Val
210                 215                 220 ctg gcg gcg gac gac cag ggc cgg ctg ctc tac agc gac ttc ctc act         720
Leu Ala Ala Asp Asp Gln Gly Arg Leu Leu Tyr Ser Asp Phe Leu Thr
225                 230                 235                 240 ttc ctg gac cgc gac gac ggc gcc aag aag gtc ttc tac gtg atc gag         768
Phe Leu Asp Arg Asp Asp Gly Ala Lys Lys Val Phe Tyr Val Ile Glu
                245                 250                 255 acg cgg gag ccg cgc gag cgc ctg ctg ctc acc gcc gcg cac ctg ctc         816
Thr Arg Glu Pro Arg Glu Arg Leu Leu Leu Thr Ala Ala His Leu Leu
            260                 265                 270 ttt gtg gcg ccg cac aac gac tcg gcc acc ggg gag ccc gag gcg tcc         864
Phe Val Ala Pro His Asn Asp Ser Ala Thr Gly Glu Pro Glu Ala Ser
        275                 280                 285 tcg ggc tcg ggg ccg cct tcc ggg ggc gca ctg ggg cct cgg gcg ctg         912
Ser Gly Ser Gly Pro Pro Ser Gly Gly Ala Leu Gly Pro Arg Ala Leu
290                 295                 300 ttc gcc agc cgc gtg cgc ccg ggc cag cgc gtg tac gtg gtg gcc gag         960
Phe Ala Ser Arg Val Arg Pro Gly Gln Arg Val Tyr Val Val Ala Glu
305                 310                 315                 320 cgt gac ggg gac cgc cgg ctc ctg ccc gcc gct gtg cac agc gtg acc        1008
Arg Asp Gly Asp Arg Arg Leu Leu Pro Ala Ala Val His Ser Val Thr
                325                 330                 335 cta agc gag gag gcc gcg ggc gcc tac gcg ccg ctc acg gcc cag ggc        1056
Leu Ser Glu Glu Ala Ala Gly Ala Tyr Ala Pro Leu Thr Ala Gln Gly
            340                 345                 350 acc att ctc atc aac cgg gtg ctg gcc tcg tgc tac gcg gtc atc gag        1104
Thr Ile Leu Ile Asn Arg Val Leu Ala Ser Cys Tyr Ala Val Ile Glu
        355                 360                 365 gag cac agc tgg gcg cac cgg gcc ttc gcg ccc ttc cgc ctg gcg cac        1152
Glu His Ser Trp Ala His Arg Ala Phe Ala Pro Phe Arg Leu Ala His
370                 375                 380 gcg ctc ctg gct gca ctg gcg ccc gcg cgc acg gac cgc ggg ggg gac        1200
Ala Leu Leu Ala Ala Leu Ala Pro Ala Arg Thr Asp Arg Gly Gly Asp
385                 390                 395                 400 agc ggc ggc ggg gac cgc ggg ggc ggc ggc aga gta gcc cta acc        1248
Ser Gly Gly Gly Asp Arg Gly Gly Gly Gly Arg Val Ala Leu Thr
                405                 410                 415 gct cca ggt gct gcc gac gct ccg ggt gcg ggg gcc acc gcg ggc atc        1296
Ala Pro Gly Ala Ala Asp Ala Pro Gly Ala Gly Ala Thr Ala Gly Ile
        420                 425                 430 cac tgg tac tcg cag ctg ctc tac caa ata ggc acc tgg ctc ctg gac        1344
His Trp Tyr Ser Gln Leu Leu Tyr Gln Ile Gly Thr Trp Leu Leu Asp
            435                 440                 445 agc gag gcc ctg cac ccg ctg ggc atg gcg gtc aag tcc agc nnn agc        1392
Ser Glu Ala Leu His Pro Leu Gly Met Ala Val Lys Ser Ser Xaa Ser
450                 455                 460 cgg ggg gcc ggg gga ggg gcg cgg gag ggg gcc                             1425
Arg Gly Ala Gly Gly Gly Ala Arg Glu Gly Ala
465                 470                 475

<210> SEQ ID NO 33
<211> LENGTH: 939
<212> TYPE: DNA
<213> ORGANISM: Homo sapiens
<220> FEATURE:
```

```
<221> NAME/KEY: CDS
<222> LOCATION: (1)..(939)

<400> SEQUENCE: 33 cgg cgc ctc atg acc cag cgc tgc aag gac cgc ctg aac tcg ctg gct      48
Arg Arg Leu Met Thr Gln Arg Cys Lys Asp Arg Leu Asn Ser Leu Ala
 1               5                  10                  15 atc tcg gtg atg aac cag tgg ccc ggt gtg aag ctg cgg gtg acc gag      96
Ile Ser Val Met Asn Gln Trp Pro Gly Val Lys Leu Arg Val Thr Glu
            20                  25                  30 ggc tgg gac gag gac ggc cac cac tca gag gag tcc ctg cat tat gag     144
Gly Trp Asp Glu Asp Gly His His Ser Glu Glu Ser Leu His Tyr Glu
        35                  40                  45 ggc cgc gcg gtg gac atc acc aca tca gac cgc gac cgc aat aag tat     192
Gly Arg Ala Val Asp Ile Thr Thr Ser Asp Arg Asp Arg Asn Lys Tyr
    50                  55                  60 gga ctg ctg gcg cgc ttg gca gtg gag gcc ggc ttt gac tgg gtg tat     240
Gly Leu Leu Ala Arg Leu Ala Val Glu Ala Gly Phe Asp Trp Val Tyr
 65                  70                  75                  80 tac gag tca aag gcc cac gtg cat tgc tcc gtc aag tcc gag cac tcg     288
Tyr Glu Ser Lys Ala His Val His Cys Ser Val Lys Ser Glu His Ser
                 85                  90                  95 gcc gca gcc aag acg ggc ggc tgc ttc cct gcc gga gcc cag gta cgc     336
Ala Ala Ala Lys Thr Gly Gly Cys Phe Pro Ala Gly Ala Gln Val Arg
            100                 105                 110 ctg gag agt ggg gcg cgt gtg gcc ttg tca gcc gtg agg ccg gga gac     384
Leu Glu Ser Gly Ala Arg Val Ala Leu Ser Ala Val Arg Pro Gly Asp
        115                 120                 125 cgt gtg ctg gcc atg ggg gag gat ggg agc ccc acc ttc agc gat gtg     432
Arg Val Leu Ala Met Gly Glu Asp Gly Ser Pro Thr Phe Ser Asp Val
    130                 135                 140 ctc att ttc ctg gac cgc gag ccc cac agg ctg aga gcc ttc cag gtc     480
Leu Ile Phe Leu Asp Arg Glu Pro His Arg Leu Arg Ala Phe Gln Val
145                 150                 155                 160 atc gag act cag gac ccc cca cgc cgc ctg gca ctc aca ccc gct cac     528
Ile Glu Thr Gln Asp Pro Pro Arg Arg Leu Ala Leu Thr Pro Ala His
                165                 170                 175 ctg ctc ttt acg gct gac aat cac acg gag ccg gca gcc cgc ttc cgg     576
Leu Leu Phe Thr Ala Asp Asn His Thr Glu Pro Ala Ala Arg Phe Arg
            180                 185                 190 gcc aca ttt gcc agc cac gtg cag cct ggc cag tac gtg ctg gtg gct     624
Ala Thr Phe Ala Ser His Val Gln Pro Gly Gln Tyr Val Leu Val Ala
        195                 200                 205 ggg gtg cca ggc ctg cag cct gcc cgc gtg gca gct gtc tct aca cac     672
Gly Val Pro Gly Leu Gln Pro Ala Arg Val Ala Ala Val Ser Thr His
    210                 215                 220 gtg gcc ctc ggg gcc tac gcc ccg ctc aca aag cat ggg aca ctg gtg     720
Val Ala Leu Gly Ala Tyr Ala Pro Leu Thr Lys His Gly Thr Leu Val
225                 230                 235                 240 gtg gag gat gtg gtg gca tcc tgc ttc gcc gcc gtg gct gac cac cac     768
Val Glu Asp Val Val Ala Ser Cys Phe Ala Ala Val Ala Asp His His
                245                 250                 255 ctg gct cag ttg gcc ttc tgg ccc ctg aga ctc ttt cac agc ttg gca     816
Leu Ala Gln Leu Ala Phe Trp Pro Leu Arg Leu Phe His Ser Leu Ala
            260                 265                 270 tgg ggc agc tgg acc ccg ggg gag ggt gtg cat tgg tac ccc cag ctg     864
Trp Gly Ser Trp Thr Pro Gly Glu Gly Val His Trp Tyr Pro Gln Leu
        275                 280                 285 ctc tac cgc ctg ggg cgt ctc ctg cta gaa gag ggc agc ttc cac cca     912
Leu Tyr Arg Leu Gly Arg Leu Leu Leu Glu Glu Gly Ser Phe His Pro
```

```
            290                 295                 300
ctg ggc atg tcc ggg gca ggg agc tga                                        939
Leu Gly Met Ser Gly Ala Gly Ser
305                 310
```

<210> SEQ ID NO 34
<211> LENGTH: 425
<212> TYPE: PRT
<213> ORGANISM: Gallus gallus

<400> SEQUENCE: 34

```
Met Val Glu Met Leu Leu Thr Arg Ile Leu Val Gly Phe Ile
 1               5                  10                  15

Cys Ala Leu Leu Val Ser Ser Gly Leu Thr Cys Gly Pro Gly Arg Gly
                20                  25                  30

Ile Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Arg
        50                  55                  60

Tyr Glu Gly Lys Ile Thr Arg Asn Ser Glu Arg Phe Lys Glu Leu Thr
 65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Thr Ala Ala
            260                 265                 270

His Leu Leu Phe Val Ala Pro Gln His Asn Gln Ser Glu Ala Thr Gly
        275                 280                 285

Ser Thr Ser Gly Gln Ala Leu Phe Ala Ser Asn Val Lys Pro Gly Gln
    290                 295                 300

Arg Val Tyr Val Leu Gly Glu Gly Gly Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350
```

```
Tyr Ala Val Ile Glu Glu His Ser Trp Ala His Trp Ala Phe Ala Pro
            355                 360                 365
Phe Arg Leu Ala Gln Gly Leu Leu Ala Ala Leu Cys Pro Asp Gly Ala
            370                 375                 380
Ile Pro Thr Ala Ala Thr Thr Thr Gly Ile His Trp Tyr Ser Arg
385                 390                 395                 400
Leu Leu Tyr Arg Ile Gly Ser Trp Val Leu Asp Gly Asp Ala Leu His
                    405                 410                 415
Pro Leu Gly Met Val Ala Pro Ala Ser
            420                 425

<210> SEQ ID NO 35
<211> LENGTH: 396
<212> TYPE: PRT
<213> ORGANISM: Mus musculus

<400> SEQUENCE: 35

Met Ala Leu Pro Ala Ser Leu Leu Pro Leu Cys Cys Leu Ala Leu Leu
 1               5                  10                  15
Ala Leu Ser Ala Gln Ser Cys Gly Pro Gly Arg Gly Pro Val Gly Arg
                20                  25                  30
Arg Arg Tyr Val Arg Lys Gln Leu Val Pro Leu Leu Tyr Lys Gln Phe
            35                  40                  45
Val Pro Ser Met Pro Glu Arg Thr Leu Gly Ala Ser Gly Pro Ala Glu
    50                  55                  60
Gly Arg Val Thr Arg Gly Ser Glu Arg Phe Arg Asp Leu Val Pro Asn
65                  70                  75                  80
Tyr Asn Pro Asp Ile Ile Phe Lys Asp Glu Glu Asn Ser Gly Ala Asp
                85                  90                  95
Arg Leu Met Thr Glu Arg Cys Lys Glu Arg Val Asn Ala Leu Ala Ile
            100                 105                 110
Ala Val Met Asn Met Trp Pro Gly Val Arg Leu Arg Val Thr Glu Gly
            115                 120                 125
Trp Asp Glu Asp Gly His His Ala Gln Asp Ser Leu His Tyr Glu Gly
    130                 135                 140
Arg Ala Leu Asp Ile Thr Thr Ser Asp Arg Asp Arg Asn Lys Tyr Gly
145                 150                 155                 160
Leu Leu Ala Arg Leu Ala Val Glu Ala Gly Phe Asp Trp Val Tyr Tyr
                165                 170                 175
Glu Ser Arg Asn His Ile His Val Ser Val Lys Ala Asp Asn Ser Leu
            180                 185                 190
Ala Val Arg Ala Gly Gly Cys Phe Pro Gly Asn Ala Thr Val Arg Leu
            195                 200                 205
Arg Ser Gly Glu Arg Lys Gly Leu Arg Glu Leu His Arg Gly Asp Trp
    210                 215                 220
Val Leu Ala Ala Asp Ala Ala Gly Arg Val Val Pro Thr Pro Val Leu
225                 230                 235                 240
Leu Phe Leu Asp Arg Asp Leu Gln Arg Ala Ser Phe Val Ala Val
                245                 250                 255
Glu Thr Glu Arg Pro Pro Arg Lys Leu Leu Leu Thr Pro Trp His Leu
            260                 265                 270
Val Phe Ala Ala Arg Gly Pro Ala Pro Ala Pro Gly Asp Phe Ala Pro
            275                 280                 285
Val Phe Ala Arg Arg Leu Arg Ala Gly Asp Ser Val Leu Ala Pro Gly
```

```
                       290                 295                 300
Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu His Ala Leu Gly Ala
                355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Met Gly
385                 390                 395

<210> SEQ ID NO 36
<211> LENGTH: 336
<212> TYPE: PRT
<213> ORGANISM: Mus musculus

<400> SEQUENCE: 36

Glu Arg Phe Lys Glu Leu Thr Pro Asn Tyr Asn Pro Asp Ile Ile Phe
1               5                   10                  15

Lys Asp Glu Glu Asn Thr Gly Ala Asp Arg Leu Met Thr Gln Arg Cys
                20                  25                  30

Lys Asp Arg Leu Asn Ser Leu Ala Ile Ser Val Met Asn Gln Trp Pro
            35                  40                  45

Gly Val Lys Leu Arg Val Thr Glu Gly Trp Asp Glu Asp Gly His His
    50                  55                  60

Ser Glu Glu Ser Leu His Tyr Glu Gly Arg Ala Val Asp Ile Thr Thr
65                  70                  75                  80

Ser Asp Arg Asp Arg Asn Lys Tyr Gly Leu Leu Ala Arg Leu Ala Val
                85                  90                  95

Glu Ala Gly Phe Asp Trp Val Tyr Tyr Glu Ser Lys Ala His Val His
                100                 105                 110

Cys Ser Val Lys Ser Glu His Ser Ala Ala Lys Thr Gly Gly Cys
            115                 120                 125

Phe Pro Ala Gly Ala Gln Val Arg Leu Glu Asn Gly Glu Arg Val Ala
130                 135                 140

Leu Ser Ala Val Lys Pro Gly Asp Arg Val Leu Ala Met Gly Glu Asp
145                 150                 155                 160

Gly Thr Pro Thr Phe Ser Asp Val Leu Ile Phe Leu Asp Arg Glu Pro
                165                 170                 175

Asn Arg Leu Arg Ala Phe Gln Val Ile Glu Thr Gln Asp Pro Pro Arg
            180                 185                 190

Arg Leu Ala Leu Thr Pro Ala His Leu Leu Phe Ile Ala Asp Asn His
        195                 200                 205

Thr Glu Pro Ala Ala His Phe Arg Ala Thr Phe Ala Ser His Val Gln
    210                 215                 220

Pro Gly Gln Tyr Val Leu Val Ser Gly Val Pro Gly Leu Gln Pro Ala
225                 230                 235                 240

Arg Val Ala Ala Val Ser Thr His Val Ala Leu Gly Ser Tyr Ala Pro
                245                 250                 255

Leu Thr Arg His Gly Thr Leu Val Val Glu Asp Val Val Ala Ser Cys
            260                 265                 270
```

```
Phe Ala Ala Val Ala Asp His His Leu Ala Gln Leu Ala Phe Trp Pro
            275                 280                 285
Leu Arg Leu Phe Pro Ser Leu Ala Trp Gly Ser Trp Thr Pro Ser Glu
        290                 295                 300
Gly Val His Trp Tyr Pro Gln Met Leu Tyr Arg Leu Gly Arg Leu Leu
305                 310                 315                 320
Leu Glu Glu Ser Thr Phe His Pro Leu Gly Met Ser Gly Ala Gly Ser
                325                 330                 335

<210> SEQ ID NO 37
<211> LENGTH: 437
<212> TYPE: PRT
<213> ORGANISM: Mus musculus

<400> SEQUENCE: 37

Met Leu Leu Leu Ala Arg Cys Phe Leu Val Ile Leu Ala Ser Ser
1               5                   10                  15
Leu Leu Val Cys Pro Gly Leu Ala Cys Gly Pro Gly Arg Gly Phe Gly
            20                  25                  30
Lys Arg Arg His Pro Lys Lys Leu Thr Pro Leu Ala Tyr Lys Gln Phe
        35                  40                  45
Ile Pro Asn Val Ala Glu Lys Thr Leu Gly Ala Ser Gly Arg Tyr Glu
    50                  55                  60
Gly Lys Ile Thr Arg Asn Ser Glu Arg Phe Lys Glu Leu Thr Pro Asn
65                  70                  75                  80
Tyr Asn Pro Asp Ile Ile Phe Lys Asp Glu Glu Asn Thr Gly Ala Asp
                85                  90                  95
Arg Leu Met Thr Gln Arg Cys Lys Asp Lys Leu Asn Ala Leu Ala Ile
            100                 105                 110
Ser Val Met Asn Gln Trp Pro Gly Val Lys Leu Arg Val Thr Glu Gly
        115                 120                 125
Trp Asp Glu Asp Gly His His Ser Glu Glu Ser Leu His Tyr Glu Gly
130                 135                 140
Arg Ala Val Asp Ile Thr Thr Ser Asp Arg Asp Arg Ser Lys Tyr Gly
145                 150                 155                 160
Met Leu Ala Arg Leu Ala Val Glu Ala Gly Phe Asp Trp Val Tyr Tyr
                165                 170                 175
Glu Ser Lys Ala His Ile His Cys Ser Val Lys Ala Glu Asn Ser Val
            180                 185                 190
Ala Ala Lys Ser Gly Gly Cys Phe Pro Gly Ser Ala Thr Val His Leu
        195                 200                 205
Glu Gln Gly Gly Thr Lys Leu Val Lys Asp Leu Arg Pro Gly Asp Arg
    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Leu Glu Pro Arg Glu Arg Leu Leu Thr Ala Ala His Leu
            260                 265                 270
Leu Phe Val Ala Pro His Asn Asp Ser Gly Pro Thr Pro Gly Pro Ser
        275                 280                 285
Ala Leu Phe Ala Ser Arg Val Arg Pro Gly Gln Arg Val Tyr Val Val
    290                 295                 300
Ala Glu Arg Gly Gly Asp Arg Arg Leu Leu Pro Ala Ala Val His Ser
305                 310                 315                 320
```

```
Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
                355                 360                 365

Ala His Ala Leu Leu Ala Ala Leu Ala Pro Ala Arg Thr Asp Gly Gly
            370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
                420                 425                 430

Ala Val Lys Ser Ser
                435

<210> SEQ ID NO 38
<211> LENGTH: 418
<212> TYPE: PRT
<213> ORGANISM: Brachydanio rerio

<400> SEQUENCE: 38

Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
```

```
                        245                 250                 255
Thr Gln Glu Pro Val Glu Lys Ile Thr Leu Thr Ala Ala His Leu Leu
                260                 265                 270

Phe Val Leu Asp Asn Ser Thr Glu Asp Leu His Thr Met Thr Ala Ala
            275                 280                 285

Tyr Ala Ser Ser Val Arg Ala Gly Gln Lys Val Met Val Val Asp Asp
        290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
                340                 345                 350

Ala His Leu Ala Phe Ala Pro Ala Arg Leu Tyr Tyr Tyr Val Ser Ser
                355                 360                 365

Phe Leu Phe Pro Gln Asn Ser Ser Arg Ser Asn Ala Thr Leu Gln
        370                 375                 380

Gln Glu Gly Val His Trp Tyr Ser Arg Leu Leu Tyr Gln Met Gly Thr
385                 390                 395                 400

Trp Leu Leu Asp Ser Asn Met Leu His Pro Leu Gly Met Ser Val Asn
                405                 410                 415

Ser Ser

<210> SEQ ID NO 39
<211> LENGTH: 475
<212> TYPE: PRT
<213> ORGANISM: Homo sapiens
<220> FEATURE:
<221> NAME/KEY: SITE
<222> LOCATION: (463)
<223> OTHER INFORMATION: Xaa=unknown amino acid

<400> SEQUENCE: 39

Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
                100                 105                 110

Val Met Asn Gln Trp Pro Gly Val Lys Leu Arg Val Thr Glu Gly Trp
            115                 120                 125

Asp Glu Asp Gly His His Ser Glu Glu Ser Leu His Tyr Glu Gly Arg
        130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175
```

```
Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
            195                 200                 205

Gln Gly Gly Thr Lys Leu Val Lys Asp Leu Ser Pro Gly Asp Arg Val
            210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
            290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
            370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser Xaa Ser
            450                 455                 460

Arg Gly Ala Gly Gly Ala Arg Glu Gly Ala
465                 470                 475

<210> SEQ ID NO 40
<211> LENGTH: 312
<212> TYPE: PRT
<213> ORGANISM: Homo sapiens

<400> SEQUENCE: 40

Arg Arg Leu Met Thr Gln Arg Cys Lys Asp Arg Leu Asn Ser Leu Ala
1               5                   10                  15

Ile Ser Val Met Asn Gln Trp Pro Gly Val Lys Leu Arg Val Thr Glu
            20                  25                  30

Gly Trp Asp Glu Asp Gly His His Ser Glu Glu Ser Leu His Tyr Glu
            35                  40                  45

Gly Arg Ala Val Asp Ile Thr Thr Ser Asp Arg Asp Arg Asn Lys Tyr
        50                  55                  60

Gly Leu Leu Ala Arg Leu Ala Val Glu Ala Gly Phe Asp Trp Val Tyr
65                  70                  75                  80
```

```
Tyr Glu Ser Lys Ala His Val His Cys Ser Val Lys Ser Glu His Ser
                85                  90                  95

Ala Ala Ala Lys Thr Gly Gly Cys Phe Pro Ala Gly Ala Gln Val Arg
            100                 105                 110

Leu Glu Ser Gly Ala Arg Val Ala Leu Ser Ala Val Arg Pro Gly Asp
        115                 120                 125

Arg Val Leu Ala Met Gly Glu Asp Gly Ser Pro Thr Phe Ser Asp Val
    130                 135                 140

Leu Ile Phe Leu Asp Arg Glu Pro His Arg Leu Arg Ala Phe Gln Val
145                 150                 155                 160

Ile Glu Thr Gln Asp Pro Pro Arg Arg Leu Ala Leu Thr Pro Ala His
                165                 170                 175

Leu Leu Phe Thr Ala Asp Asn His Thr Glu Pro Ala Ala Arg Phe Arg
            180                 185                 190

Ala Thr Phe Ala Ser His Val Gln Pro Gly Gln Tyr Val Leu Val Ala
        195                 200                 205

Gly Val Pro Gly Leu Gln Pro Ala Arg Val Ala Ala Val Ser Thr His
    210                 215                 220

Val Ala Leu Gly Ala Tyr Ala Pro Leu Thr Lys His Gly Thr Leu Val
225                 230                 235                 240

Val Glu Asp Val Val Ala Ser Cys Phe Ala Ala Val Ala Asp His His
                245                 250                 255

Leu Ala Gln Leu Ala Phe Trp Pro Leu Arg Leu Phe His Ser Leu Ala
            260                 265                 270

Trp Gly Ser Trp Thr Pro Gly Glu Gly Val His Trp Tyr Pro Gln Leu
        275                 280                 285

Leu Tyr Arg Leu Gly Arg Leu Leu Glu Glu Gly Ser Phe His Pro
    290                 295                 300

Leu Gly Met Ser Gly Ala Gly Ser
305                 310
```

<210> SEQ ID NO 41
<211> LENGTH: 167
<212> TYPE: PRT
<213> ORGANISM: Artificial Sequence
<220> FEATURE:
<223> OTHER INFORMATION: Description of Artificial Sequence: General
      hedgehog polypeptide formula
<221> NAME/KEY: SITE
<222> LOCATION: (7)
<223> OTHER INFORMATION: Xaa=Gly, Ala, Val, Leu, Ile, Pro, Phe, or Tyr
<221> NAME/KEY: SITE
<222> LOCATION: (8)
<223> OTHER INFORMATION: Xaa=Gly, Ala, Val, Leu, or Ile
<221> NAME/KEY: SITE
<222> LOCATION: (9)
<223> OTHER INFORMATION: Xaa=Gly, Ala, Val, Leu, Ile, Lys, His, or Arg
<221> NAME/KEY: SITE
<222> LOCATION: (12)
<223> OTHER INFORMATION: Xaa=Lys, Arg or His
<221> NAME/KEY: SITE
<222> LOCATION: (13)
<223> OTHER INFORMATION: Xaa=Phe, Trp, Tyr, or an amino acid gap
<221> NAME/KEY: SITE
<222> LOCATION: (14)
<223> OTHER INFORMATION: Xaa=Gly, Ala, Val, Leu, Ile, or an amino acid
      gap
<221> NAME/KEY: SITE
<222> LOCATION: (17)
<223> OTHER INFORMATION: Xaa=Asn, Gln, His, Arg, or Lys
<221> NAME/KEY: SITE
<222> LOCATION: (19)
<223> OTHER INFORMATION: Xaa=Gly, Ala, Val, Leu, Ile, Ser, or Thr -continued

```
<221> NAME/KEY: SITE
<222> LOCATION: (22)
<223> OTHER INFORMATION: Xaa=Gly, Ala, Val, Leu, Ile, Ser, or Thr
<221> NAME/KEY: SITE
<222> LOCATION: (27)
<223> OTHER INFORMATION: Xaa=Gly, Ala, Val, Leu, Ile, Ser, or Thr
<221> NAME/KEY: SITE
<222> LOCATION: (29)
<223> OTHER INFORMATION: Xaa=Ser, Thr, Gln, or Asn
<221> NAME/KEY: SITE
<222> LOCATION: (30)
<223> OTHER INFORMATION: Xaa=Met, Cys, Gly, Ala, Val, Leu, Ile, Ser, or
      Thr
<221> NAME/KEY: SITE
<222> LOCATION: (31)
<223> OTHER INFORMATION: Xaa=Gly, Ala, Val, Leu, Ile, or Pro
<221> NAME/KEY: SITE
<222> LOCATION: (33)
<223> OTHER INFORMATION: Xaa=Arg, His or Lys
<221> NAME/KEY: SITE
<222> LOCATION: (40)
<223> OTHER INFORMATION: Xaa=Gly, Ala, Val, Leu, Ile,Pro, Arg, His, or
      Lys
<221> NAME/KEY: SITE
<222> LOCATION: (41)
<223> OTHER INFORMATION: Xaa=Gly, Ala, Val, Leu, Ile, Phe, or Tyr
<221> NAME/KEY: SITE
<222> LOCATION: (44)
<223> OTHER INFORMATION: Xaa=Arg, His or Lys
<221> NAME/KEY: SITE
<222> LOCATION: (45)
<223> OTHER INFORMATION: Xaa=Gly, Ala, Val, Leu, Ile, Ser, or Thr
<221> NAME/KEY: SITE
<222> LOCATION: (46)
<223> OTHER INFORMATION: Xaa=Thr or Ser
<221> NAME/KEY: SITE
<222> LOCATION: (48)
<223> OTHER INFORMATION: Xaa=Ly, Ala, Val, Leu, Ile, Asn, or Gln
<221> NAME/KEY: SITE
<222> LOCATION: (53)
<223> OTHER INFORMATION: Xaa=Arg, His or Lys
<221> NAME/KEY: SITE
<222> LOCATION: (54)
<223> OTHER INFORMATION: Xaa=Asp or Glu
<221> NAME/KEY: SITE
<222> LOCATION: (71)
<223> OTHER INFORMATION: Xaa=Ser or Thr
<221> NAME/KEY: SITE
<222> LOCATION: (79)
<223> OTHER INFORMATION: Xaa=Glu, Asp, Gln, or Asn
<221> NAME/KEY: SITE
<222> LOCATION: (83)
<223> OTHER INFORMATION: Xaa=Glu or Asp
<221> NAME/KEY: SITE
<222> LOCATION: (84)
<223> OTHER INFORMATION: Xaa=Arg, His or Lys
<221> NAME/KEY: SITE
<222> LOCATION: (85)
<223> OTHER INFORMATION: Xaa=Gly, Ala, Val, Leu, or Ile
<221> NAME/KEY: SITE
<222> LOCATION: (87)
<223> OTHER INFORMATION: Xaa=Gly, Ala, Val, Leu, Ile, Thr, or Ser
<221> NAME/KEY: SITE
<222> LOCATION: (95)
<223> OTHER INFORMATION: Xaa=Met, Cys, Gln, Asn, Arg, Lys, or His
<221> NAME/KEY: SITE
<222> LOCATION: (100)
<223> OTHER INFORMATION: Xaa=Arg, His or Lys
<221> NAME/KEY: SITE
<222> LOCATION: (107)
<223> OTHER INFORMATION: Xaa=Trp, Phe, Tyr, Arg, His, or Lys
<221> NAME/KEY: SITE
<222> LOCATION: (114)
<223> OTHER INFORMATION: Xaa=Gly, Ala, Val, Leu, Ile, Ser, Thr, Tyr, or
      Phe
<221> NAME/KEY: SITE
<222> LOCATION: (115)
<223> OTHER INFORMATION: Xaa=Gln, Asn, Asp, or Glu
<221> NAME/KEY: SITE
```

```
<222> LOCATION: (116)
<223> OTHER INFORMATION: Xaa=Asp or Glu
<221> NAME/KEY: SITE
<222> LOCATION: (125)
<223> OTHER INFORMATION: Xaa=Gly, Ala, Val, Leu, or Ile
<221> NAME/KEY: SITE
<222> LOCATION: (134)
<223> OTHER INFORMATION: Xaa=Arg, His or Lys
<221> NAME/KEY: SITE
<222> LOCATION: (135)
<223> OTHER INFORMATION: Xaa=Asn, Gln, Thr, or Ser
<221> NAME/KEY: SITE
<222> LOCATION: (139)
<223> OTHER INFORMATION: Xaa=Gly, Ala, Val, Lau, Ile, Ser, Thr, Met, or
     Cys
<221> NAME/KEY: SITE
<222> LOCATION: (141)
<223> OTHER INFORMATION: Xaa=Gly, Ala, Val,  Leu, Ile, Thr, or Ser
<221> NAME/KEY: SITE
<222> LOCATION: (157)
<223> OTHER INFORMATION: Xaa=Arg, His or Lys
<221> NAME/KEY: SITE
<222> LOCATION: (158)
<223> OTHER INFORMATION: Xaa=Asn Gln, Gly, Ala, Val, Leu, or Ile
<221> NAME/KEY: SITE
<222> LOCATION: (160)
<223> OTHER INFORMATION: Xaa=Gly, Ala, Val, Leu, or Ile
<221> NAME/KEY: SITE
<222> LOCATION: (162)
<223> OTHER INFORMATION: Xaa=Gly, Ala, Val, Leu, Ile, Ser, Thr, or Cys
<221> NAME/KEY: SITE
<222> LOCATION: (166)
<223> OTHER INFORMATION: Xaa=Gly, Ala, Val, Leu, Ile, Thr, or Ser
<221> NAME/KEY: SITE
<222> LOCATION: (167)
<223> OTHER INFORMATION: Xaa=Asp or Glu

<400> SEQUENCE: 41

Cys Gly Pro Gly Arg Gly Xaa Xaa Xaa Arg Xaa Xaa Xaa Pro Lys
 1               5                  10                  15

Xaa Leu Xaa Pro Leu Xaa Tyr Lys Gln Phe Xaa Pro Xaa Xaa Xaa Glu
             20                  25                  30

Xaa Thr Leu Gly Ala Ser Gly Xaa Xaa Glu Gly Xaa Xaa Xaa Arg Xaa
         35                  40                  45

Ser Glu Arg Phe Xaa Xaa Leu Thr Pro Asn Tyr Asn Pro Asp Ile Ile
     50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
                 85                  90                  95

Pro Gly Val Xaa Leu Arg Val Thr Glu Gly Xaa Asp Glu Asp Gly His
             100                 105                 110

His Xaa Xaa Xaa Ser Leu His Tyr Glu Gly Arg Ala Xaa Asp Ile Thr
         115                 120                 125

Thr Ser Asp Arg Asp Xaa Xaa Lys Tyr Gly Xaa Leu Xaa Arg Leu Ala
     130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
                 165

<210> SEQ ID NO 42
<211> LENGTH: 165
<212> TYPE: PRT
<213> ORGANISM: Artificial Sequence
<220> FEATURE:
<223> OTHER INFORMATION: Description of Artificial Sequence: General Shh
```

```
          polypeptide formula
<221> NAME/KEY: SITE
<222> LOCATION: (7)
<223> OTHER INFORMATION: Xaa=Gly, Ala, Val, Leu, Ile, Phe, Tyr, or Trp
<221> NAME/KEY: SITE
<222> LOCATION: (9)
<223> OTHER INFORMATION: Xaa=Arg, His or Lys
<221> NAME/KEY: SITE
<222> LOCATION: (44)
<223> OTHER INFORMATION: Xaa=Gly, Ala, Val, Leu, Ile, Ser, or Thr
<221> NAME/KEY: SITE
<222> LOCATION: (85)
<223> OTHER INFORMATION: Xaa=Gly, Ala, Val, Leu, Ile, Ser, or Thr
<221> NAME/KEY: SITE
<222> LOCATION: (93)
<223> OTHER INFORMATION: Xaa=Lys, Arg, His, Asn, or Gln
<221> NAME/KEY: SITE
<222> LOCATION: (98)
<223> OTHER INFORMATION: Xaa=Lys, Arg or His
<221> NAME/KEY: SITE
<222> LOCATION: (112)
<223> OTHER INFORMATION: Xaa=Ser, thr, Tyr, Trp, or Phe
<221> NAME/KEY: SITE
<222> LOCATION: (132)
<223> OTHER INFORMATION: Xaa=Lys, Arg, or His
<221> NAME/KEY: SITE
<222> LOCATION: (137)
<223> OTHER INFORMATION: Xaa=Met, Cys, Ser, or Thr
<221> NAME/KEY: SITE
<222> LOCATION: (139)
<223> OTHER INFORMATION: Xaa=Gly, Ala, Val, Leu, Ile, Ser, or Thr

<400> SEQUENCE: 42

Cys Gly Pro Gly Arg Gly Xaa Gly Xaa Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Xaa Arg Asn Ser Glu
         35                  40                  45

Arg Phe Lys Glu Leu Thr Pro Asn Tyr Asn Pro Asp Ile Ile Phe Lys
     50                  55                  60

Asp Glu Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
             100                 105                 110

Glu Glu Ser Leu His Tyr Glu Gly Arg Ala Val Asp Ile Thr Thr Ser
         115                 120                 125

Asp Arg Asp Xaa Ser Lys Tyr Gly Xaa Leu Xaa Arg Leu Ala Val Glu
     130                 135                 140

Ala Gly Phe Asp Trp Val Tyr Tyr Glu Ser Lys Ala His Ile His Cys
145                 150                 155                 160

Ser Val Lys Ala Glu
                165
```

METHODS OF USING HEDGEHOG PROTEINS TO MODULATE HEMATOPOIESIS AND VASCULAR GROWTH

CROSS REFERENCE

This application claims priority from provisional application Ser. No. 60/037,513 filed Feb. 10, 1997 and provisional application Ser. No. 60/049,763 filed Jun. 16, 1997, both applications being here incorporated by reference.

This invention was supported by NIH Grant No. GM-42413 and the U.S. government has certain rights in the invention.

TECHNICAL FIELD

Novel methods and compositions are provided, for modulating hematopoeisis and vascular growth in vitro and in vivo.

BACKGROUND ART

The life of a new individual is initiated by the fusion of genetic material from the two gametes, the sperm and the egg. After several rounds of division, the cells begin a process of differentiation that ultimately results in the mature adult organism. The process involves many steps including a diverse number of factors which act at specific times during the pathway leading to maturation. The maturation to the adult form does not completely terminate the differentiation process. This is because the adult organism has, in addition to fully differentiated cells, undifferentiated stem cells that are available for both replenishment of differentiated cells during the natural cycle of degeneration and regeneration; and also for repair of damaged tissue. Examples of undifferentiated cells in the adult are bone marrow stem cells (more specifically hematopoeitic stem cells and progenitor cells) as well as endothelial progenitor cells. Cells of this sort provide a therapeutic toolbox in nature for repair and reconstitution of damaged or diseased tissue in a patient. The use of this therapeutic tool box by health care providers for treating patients is limited by the lack of methods to manipulate the differentiation pathways of these cells and to prepare or boost existing numbers of undifferentiated cells without triggering differentiation.

There is a need therefore to find novel methods in which the supply of undifferentiated cells from any particular individual may be increased, for example, by stimulating the proliferation of the cells without inducing differentiation. It is also desirable to modulate differentiation of undifferentiated cells in a controlled manner. Undifferentiated cells that are ready to differentiate when stimulated to do so offer a treatment to subjects that suffer from diseases in which either the stem cells themselves become depleted such as in chemotherapy which destroys bone marrow, or alternatively for diseases in which differentiated cells are being depleted at a rate that is greater than the body can compensate for the loss by means of using the natural supply of undifferentiated stem cells. For example, in AIDS there is a rapid destruction of mature blood cells by the human immune deficiency virus resulting in a dramatic decrease of immune cells in the patient. There is a need to identify factors that cause stem cells to proliferate and that can modulate differentiation so as to enhance the availability of such cells.

The adult organism contains both endothelial stem cells and hematopoietic stem cells (HSC). These cells are undifferentiated but under appropriate conditions, differentiate to form blood cells and blood vessels respectively. Although there have been extensive studies on vascular growth in the adult, it is unknown whether vascular growth is restricted to vessel extension (angiogenesis) or whether there is de novo vascular development (vasculogenesis) also. The understanding of factors that regulate vascular growth is not only important in understanding how to inhibit abnormal vascular growth such as occurs in tumors, rheumatoid arthritis, hemangiomas, angiofibromas, psoriasis and capillary proliferation and diabetes but also in understanding how to repair vessels after traumatic events including surgery, transplantation and nutrient deprivation to tissues such as occurs in vascular diseases such as cardiovascular or cerebrovascular diseases.

In contrast to vascular growth, hematopoiesis is normally a continuous process throughout the life of an adult. Blood cells are regularly degraded and new cells are formed resulting in a daily production of millions of mature blood cells. Numerous diseases result from imbalances between degradation and reconstitution of blood cells or from generation of inappropriate numbers of certain blood cells. A simplified schematic of blood cell differentiation is provided in FIG. 12. This schematic shows the developmental pathway of eight different types of blood cells that may be derived from a hematopoietic stem cell (HSC) and which passes through an immature progenitor stage. The pluripotent hematopoietic stem cell gives rise to erythrocytes, neutrophils, basophils, eosinophils, platelets, mast cells, monocytes, tissue macrophages, osteoclasts and T and B lymphocytes through a number of different pathways. In the adult, erythrocytes are formed when the pluripotent stem cell differentiates into BFU-E (a burst forming unit-erythroid), which in turn forms a CFU-E (colony forming unit-erythroid). Organs which form blood cells in the adult include bone marrow and to a lesser extent, liver whereas the spleen is the primary site of subsequent clearing of aged or abnormal blood cells. Although the search for factors that regulate hematopoiesis has not been restricted to adults, studies in embryos has been restricted to events that occur when the embryo is already at a relatively advanced stage of development.

With regard to cellular events in the embryo, Cumano et al., *Lymphoid Potential, Probed before Circulation in Mouse, Is Restricted to Caudal Intraembryonic Splanchnopleura*, 86 (1996) 907–16, proposed that the hematopoietic stem cells (HSC) that populate the adult arise from an intraembryonic site. Blood cells reported to first arise in blood islands in the embryo, appear to originate from hematopoietic progenitor cells in the para-aortic splanchnopleura within the developing embryo. (Cumano et al.(1996). The early development of a mouse is shown in FIG. 14 and the region of early blood island formation is identified on the periphery of the extracoelomic cavity.

At present, there are a number of growth factors that are known to stimulate early stage intermediate cells in different hematopoietic pathways. These include the hematopoletic growth factors, erythropoietin, granulocyte colony stimulating factor (G-CSF) and granulocyte-macrophage colony stimulating factor (GMCSF). For example, CFU-E respond to erythropoietin to produce the first recognizable differentiated member of the erythrocyte lineage, the proerythroblast. As blood oxygen levels fall, erythropoietin levels increase, leading to the production of more red blood cells. As a red blood cell matures, it becomes an erythroblast, synthesizing an enormous amount of hemoglobin and then an erythrocyte. Erythrocytes leave the bone marrow to undertake oxygen delivery to bodily tissues. Although the known factors may have utility in the treatment of certain malignancies or hematologic/immune deficiencies, there is a great need for development of additional therapies, particularly those with a wider range of biological activities that act earlier in the differentiation pathway. The availability of a molecule that could stimulate proliferation and/or differentiation of HSC early in the pathway of differentiation would be especially valuable as a therapeutic. However, there are no factors that are known beyond doubt to stimulate the growth of pluripotent HSC themselves. A protein called stem cell factor has been identified to be associated with pluripotent hematopoietic cells, but this factor is believed to be a survival factor and not a factor capable of stimulating proliferation of these cells (Caceres-Cortes et al., *J. Biol. Chem.*, 269 (1994), 12084–91). There is a need to regulate proliferation and differentiation of hematopoietic stem cells. For example, it would be desirable to inhibit uncontrolled proliferation of stem cells or progenitor cells such as occurs in certain pathological conditions. There is a need for methods to expand the number of pluripotent HSC either in vitro or in vivo for use in treating patients with chronic anemia or those undergoing chemotherapy where the majority of their bone marrow cells are destroyed so that it is necessary to effectively stimulate the remaining cells or for increasing the availability of HSC for transplantation to an anaemic patient.

SUMMARY OF THE INVENTION

This invention satisfies the above need by providing novel methods and compositions that modulate proliferation and/or differentiation of undifferentiated mesodermally derived cells so as to have an effect on at least one of vascular growth and hematopoiesis.

In an embodiment of the invention, a method is provided for stimulating a population of undifferentiated mesodermally derived cells, to undergo at least one of hematopoiesis and vascular growth. The method includes the steps of selecting a compound that is functionally equivalent to a gene product expressed in an embryo's extraembryonic tissue; and causing the compound to access the cells, so as to stimulate the cells to undergo at least one of hematopoiesis and vascular growth.

In another embodiment of the invention, a method is provided for treating developmental errors in vascular growth or hematopoiesis in an embryo in utero, that includes the steps of: selecting an effective dose of a compound that is functionally equivalent to a gene product expressed in an extraembryonic tissue; and causing the compound to access a population of embryonic cells in vivo, so as to stimulate the cells to undergo at least one of hematopoiesis and vascular growth.

In another embodiment of the invention, a method is provided for treating a subject suffering from an abnormal number of erythroid cells, that includes the steps of selecting an effective dose of a compound that is functionally equivalent to a gene product expressed in an extraembryonic tissue; and causing the compound to access a population of hematopoietic stem cells over an effective time so as to modulate the number of cells undergoing at least one of proliferation or differentiation.

In another embodiment of the invention, a method is provided for treating a subject suffering from an ischemia in tissues containing mesodermally derived cells, that includes selecting an effective dose of a compound that is functionally equivalent to a gene product expressed in an extraembryonic tissue; and administering the compound to the ischemic site over an effective time so as to stimulate vascular growth.

In another embodiment of the invention, an in vitro assay is provided for determining the activity of a compound capable of modulating hematopoiesis or vascular growth, that includes the steps of selecting a population of cells from a tissue derived from a fertilized egg of a mammal, wherein the population of cells is deficient in blood formation as detectable by the absence of a predetermined marker; and adding an agent to the population of cells so as to reverse the deficiency.

In another embodiment of the invention, an assay is provided for determining the activity of a compound capable of modulating hematopoiesis or vascular growth, that includes the steps of selecting a first transgenic animal carrying a marker:$\epsilon$-globin hybrid gene, wherein the $\epsilon$-globin gene is capable of expression at least up to 15.5 dpc; mating the first transgenic animal to a second animal that is similarly transgenic; isolating an embryo from the mating at a time within the first third of the gestation period; and determining the effect of the compound on the stimulation of hematopoiesis and vascular growth in the isolated embryo by measuring marker expression.

BRIEF DESCRIPTION OF THE DRAWINGS

The foregoing features of the invention will be more readily understood by reference to the following detailed description taken with the accompanying drawings.

FIGS. 1A through 1D show four expression cassettes used to generate transgenic mice. (A) −179 lacZ$\epsilon\mu$LCR (MB70) is the basic construct with the minimal $\epsilon$-globin promoter ($\epsilon$-pro), extending to −179 with respect to the start site of transcription (+1) and ~20 bp of $\epsilon$-globin 5'-untranslated region (shown as small black box below +1). $\epsilon$-pro is linked to a LacZ expression cassette containing a Kozak consensus sequence and translational start site (SDK region). Downstream from the LacZ reporter gene is a portion of the 3'-region of the $\epsilon$-globin gene containing part of exon 2, all of intron 2 (IVS 2) and all of exon 3; these sequences are shown as black boxes (exons) and a black line (intron). The 3'-untranslated region (containing the polyadenylation site, pA) is shown as a striped line. A truncated version of the LCR (the $\mu$LCR) is located downstream from the $\mu$-lacZ sequences. (B) −849 lacZ$\epsilon\mu$LCR (MB73), (C) $\epsilon$-PRE(II+V) lacZ$\epsilon\mu$LCR (MB72); and (D) −2kblacZ$\epsilon\mu$LCR (MB92). A–D contain $\epsilon$-pro and different portions of the upstream regulatory region of the human $\epsilon$-globin gene. Eukaryotic sequences in A–D were excised from the vector by digestion with KpnI and NotI and then purified for microinjection into the male pronuclei of mouse zygotes.

FIGS. 7-1A through 7-1D show that when transgenic explants of gastrulating embryos (isolated at 6.25–6.5 dpc) are cultured on filters or glass slides for 72 hours, induction of embryonic hematopoiesis occurs in whole embryo, but is absent in epiblasts only, as determined by XGal staining. Dashed lines were drawn around the epiblasts to facilitate visualization of structures. (7-1A) whole embryo on a filter; (7-1B) epiblast on a filter; (7-1C) whole embryo on a slide; and (7-1D) epiblast on a slide.

FIGS. 7-2A through 7-2E show blood formation in transgenic embryonic explant cultures. (lacZ stained sections of embryos). Frozen tissue sections were XGAL stained to reveal cluster of lacZ-positive hematopietic cells in the whole embryos (7-2A), epiblasts (7-2B), posterior embryo portions (7-2C, 7-2D), and transgenic anterior epiblast portion adjacent to the VE (7-2E), but not in surrounding visceral endoderm and undifferentiated mesoderm nor in the nontransgenic VE tissue of anterior/VE recombinants.

FIGS. 8-1A through 8-1C show induction of hematopoiesis by visceral endoderm (VE) signals. (8-1A) dark-field photomicrograph of recombinant containing transgenic (Tg) epiblast and non-Tg VE showing localized lac Z staining in the embryo adjacent to the visceral endoderm; (8-1B) schematic diagram corresponding to panel 1A. Abbreviations: Tg, transgenic; Ve, visceral endoderm; EryP, primitive erythroid cells; (8-1C) bright field photomicrograph of recombinant shown in 1A.

FIG. 8-2 shows induction of embryonic hematopoiesis in whole embryo, and in epiblast plus visceral endoderm, but none in epiblasts only, using RT-PCR. (All samples were prepared following a 72 hour in vitro incubation of embryos isolated at 6.5 dpc). Actin served as an internal control.

FIGS. 15A through 15C show the experimental scheme for separation of epiblast into anterior and posterior portions. (A) depicts the entire 6.75 dpc embryo with visceral endoderm around the perimeter of the epiblast and the extraembryonic mesoderm. (B) depicts the embryo after the visceral endoderm has been stripped off and (C) shows the epiblast only, with a dotted line of transection showing how the anterior and posterior sections are physically divided before separate cultivation.

FIG. 16-2 shows that visceral endoderm can reprogram the anterior embryonic ectoderm (epiblast) to express hematopoietic markers. The expression of $\epsilon$-globin, $\beta$-globin, GATA-1, and CD34 markers is shown for anterior epiblast (anterior: lanes 6–10), posterior epiblast (posterior: lanes 6–10) and anterior recombined with visceral endoderm (a/Ve recombs: lanes 1–5). Control tissues were uncultured whole embryo [emb(–cx)], cultured whole embryos[emb(+cx)] and 10.5 dpc yolk sac tissue. The control marker was actin and cardiac myosin. An additional control is emb(+cx) subjected to PCR in the absence of reverse transcriptase.

FIG. 16-3 Visceral endoderm can reprogram the anterior embryonic ectoderm (epiblast) to express vascular markers. The expression of PECAM-1, flk-1 and actin is shown for anterior epiblast (anterior: lanes 6–10), posterior epiblast (posterior: lanes 6–10) and anterior recombined with visceral endoderm (a/Ve recombs: lanes 1–5). Control tissues were uncultured whole embryos [emb(–cx)], cultured whole embryos [emb(+cx)] and 10.5 dpc yolk sac tissue. The control marker was actin.

FIG. 17 shows the results of a rescue experiment using null mutant embryonic stem cells (ES) and adding back recombinant BMP-4 to the culture. (A) and (C) shows wild type embryoid bodies that arise from embryonic stem cells isolated from a wild type mouse. In (B) the embryonic stem cells are homozygous BMP-4 deficient and the embryoid bodies lack detectable blood formation. In (D), BMP-4 protein is added to the embryoid bodies of (B) and blood formation is observed.

DETAILED DESCRIPTION OF THE INVENTION

Figure 1:
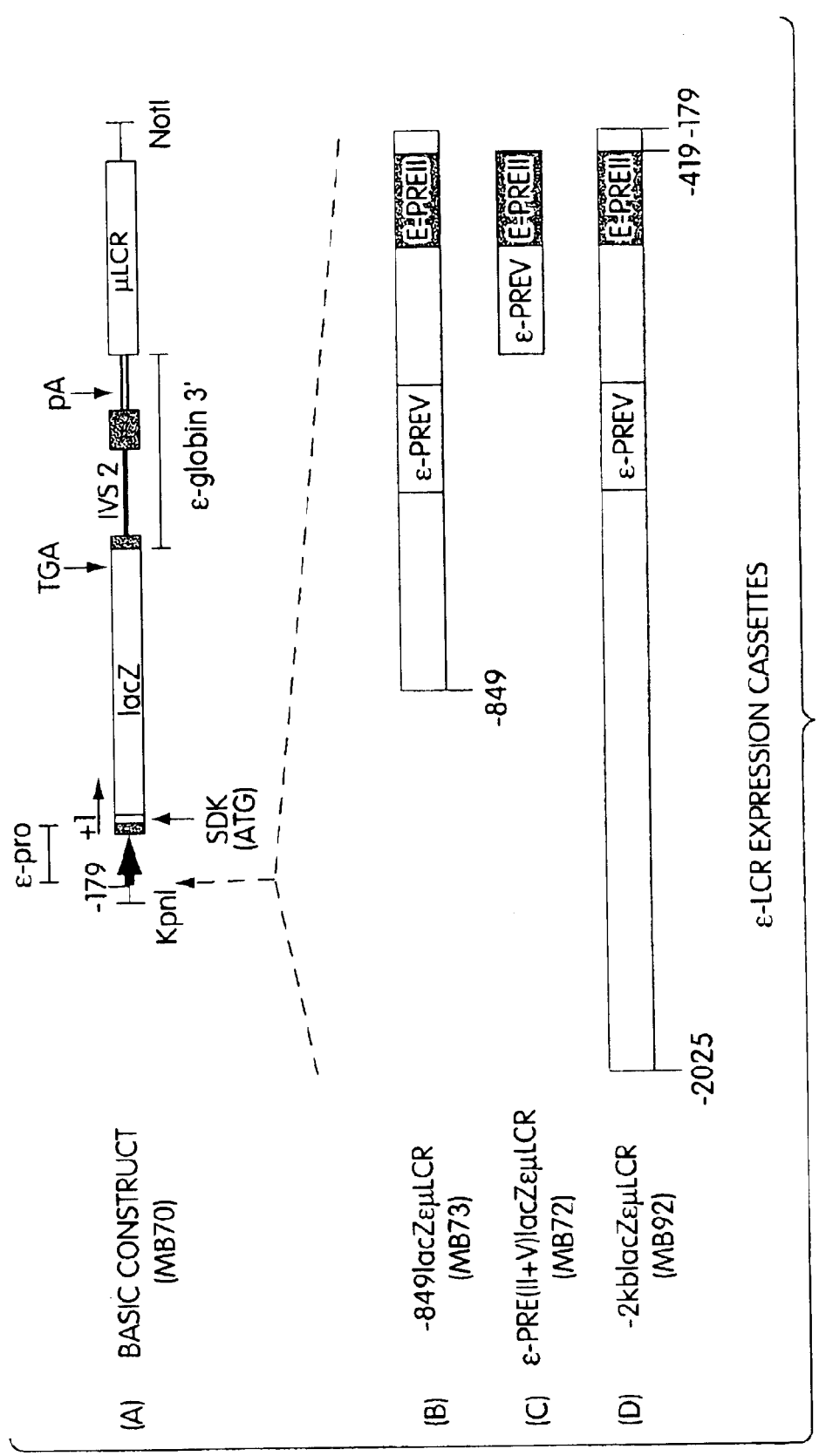
FIG. 16-1 shows that hematopoietic mesoderm arises from the posterior primitive streak (posterior mesoderm) when anterior and posterior portions of lacZ transgenic embryos are harvested at mid-to late-gastrulation. Top Panel: No staining is detected in anterior epiblasts. Bottom Panel: Dark blue XGAL histochemical staining shows blood formation in cultured posterior epiblasts. Scale bar, 1 mm.

The invention identifies for the first time methods for stimulating selected developmental activities in embryonic and adult tissue namely blood development characterized by hematopoiesis and vascular growth. The method further utilizes molecules secreted by extra-embryonic tissues capable of modulating the proliferation or differentiation of stem cells and progenitor cells from embryo or adult. Embodiments of the invention are further directed to novel assays for identifying compounds capable of stimulating hematopoiesis and vascular growth. Support for the methods of the invention are provided in the examples contained herein. According to an embodiment of the invention, compounds have been identified that are capable of stimulating blood development in the embryo and in the adult and are functionally equivalent to gene products expressed in the visceral endoderm and yolk sac mesoderm. Such gene products are exemplified by hedgehog compounds, TGF-β, TNF, and WNT compounds and are here identified as achieving a similar effect to that observed with extraembryonic tissues with regard to hematopoiesis and vascular growth in undifferentiated mesodermal derived tissues. In an embodiment of the invention, compounds including those selected from hedgehog and TGF-β may act synergistically so as to enhance their stimulatory effect on target cells.

"Adult" is defined here and in the claims as descriptive of tissues and cells derived from or within an animal subject at any time after birth.

"Embryonic" is defined here and in the claims unless stated otherwise as descriptive of tissues and cells derived from or within an animal subject at any time prior to birth.

"Blood development" is defined here and in the claims as hematopoiesis and vascular growth.

"Vascular growth" is defined here as at least one of vasculogenesis and angiogenesis and includes formation of capillaries, arteries, veins or lymphatic vessels.

"Hematopoiesis" is defined here and in the claims as the process of production of blood cells.

"Hematopoietic stem cell" is defined here and in the claims as a multipotential precursor from which all classes of blood cell are derived.

"Definitive blood cells" are defined here and in the claims as blood cells of the fetal or adult organism.

"Primitive blood cells" are defined here and in the claims as a transient population of blood cells forming during blood development in the embryo.

"Definitive endoderm" is endoderm that is derived during gastrulation from cells of the primitive streak that contribute to adult endodermally derived tissues such as gut and liver.

"Visceral endoderm" is defined here and in the claims as extraembryonic endodermal cells that are secretory and do not contribute directly to any tissues of the fully formed organism.

"Progenitor cells" are defined here and in the claims as undifferentiated cells that are more restricted in their potential to give rise to differentiated cell types compared with a stem cell.

"Committed" is defined here and in the claims as cells destined to differentiate along a specific lineage instead of retaining multipotency.

"RT-PCR" is defined here as reverse transcriptase polymerase chain reaction which permits detection of transcription of a gene in a tissue.

"Synergistic effect" is defined here as for two or more compounds where little or no biological effect is observed with the compounds alone but together the compounds have a potent biological effect.

"Hedgehog compound" is defined here and in the claims as a class of molecules of the hedgehog family that includes recombinant hedgehog protein, analogs, and derivatives of hedgehog proteins, and agonists and antagonists of hedgehog protein receptors and functional equivalents of the aforementioned.

"Undifferentiated mesodermally derived cells" is meant here and in the claims to include cells that are undifferentiated or uncommitted and further to include stem cells and progenitor cells CFU-E is here defined as erythroid colony-forming cell (unit),which is a late (mature) erythroid progenitor cell. Colonies scored as CFU-E are small, tight clusters of pigmented cells and appear within 2–3 days of culture.

BFU-E is here defined as erythroid burst-forming unit, a primitive erythroid cell. These colonies are pigmented and larger in size than CFU-E; their cells are more widely dispersed, and they appeared at a later time after plating. Their numbers are maximal around 7 days in culture.

CFU-GM is here defined as myeloid or granulocyte-macrophage colony forming unit. These are similar to BFU-E in appearance but are unpigmented.

CFU-S is here defined as spleen colony-forming unit.

Hematopoiesis and vascular growth are some of the first requirements of a growing tissue mass to secure a supply of nutrients to cells in the interior of the mass. The developing embryo requires nutrition and, therefore, the differentiation of cells to form erythroblasts (oxygen carrying cells) and the formation of a vascular system (transport system) are one of the first events in the developmental process. While the embryonic tissue is undergoing cell movement reminiscent of that seen in avian and reptilian gastrulation (migration of mesoderm and definitive endoderm cells through a primitive streak), the extraembryonic cells are making mammalian tissue that enable the fetus to survive in the maternal uterus. This includes stimulating a maternal blood supply to form the uterine endometrium. The narrow connecting stalk of extraembryonic mesoderm that links the embryo to the trophoblast eventually forms the vessels of the umbilical cord. The fully developed organ, consisting of trophoblast tissue and blood vessel-containing mesoderm, is called the chorion. The fusion of the chorion and the uterine wall forms the placenta. By 4 weeks post-conception, the human embryo has a source of nutrients through fetal blood vessels that are adjacent to the maternal circulation.

In the adult, vascular growth occurs during the repair of damaged tissues and in a variety of diseases including cancer, where a tumor releases factors that stimulate sprouting of blood vessels in normal tissue where the new blood vessels are directed into the tumor tissue. The hematopoietic stem cells (HSC) that populate the adult may arise at an intraembryonic site. (Cumano, et al. (1996)). It is believed that this mesodermal tissue is an important if not major site of origin of definitive hematopoietic stem cells and perhaps cells that give rise to the vasculature.

Although the process of hematopoiesis and vascular growth is only partly understood, the pathway of development in mice appears to mimic the equivalent process in humans. The mouse hematopoietic system is derived from the mesodermal germ layer which begins to form in primitive-streak-stage embryos around 6.5 dpc. Blood islands first appear in the extraembryonic mesoderm at 7.5 dpc and hematopoietic progenitors in the visceral yolk sac mesoderm of embryos within 1–2 somite pairs at 8 dpc. At mid-8 dpc, nucleated primitive red blood cells are visible in the vasculature of the yolk sac but do not enter the primitive circulation system until 8.5 dpc. Beginning at 8.5–9 dpc, hematopoietic progenitor cells have been found in mesodermally derived regions within the embryo body, notably the para-aortic splanchnopleura (Cumano, et al.(1996). Splanchnic mesodermal cells lining the yolk sac form cords of cells that hollow into a tube lined by endothelial cells. The central cells of the blood islands differentiate into embryonic blood cells. As the blood islands grow, they eventually merge to form the capillary network and the vitelline vessels that ultimately connect to the newly formed heart.

Until now, little has been known about the biochemical events prior to about 8 dpc that play a role in vasculogenesis and hematopoiesis. However, we assert that this stage in development play a significant role in the maturation of the blood system in the embryo and in the adult. According to embodiments of the invention, processes of vascular growth and hematopoiesis in embryonic development are affected by compounds in the visceral endoderm. For example, we have identified for the first time that hedgehog proteins act on undifferentiated mesodermal derived cells in vitro to stimulate blood formation and on embryonic tissue and yolk sac development at very early stages in the hematopoiesis and vascular growth pathways. Furthermore, according to the invention, these early acting compounds have utility in regulating hematopoiesis and vascular growth in the adult animal. (Table 1 and 2). According to embodiments of the invention, "stimulating a population of undifferentiated mesodermally derived cells to undergo at least one of hematopoiesis and vascular growth" includes stimulating proliferation of hematopoietic stem cells and progenitor cells prior to differentiation (Example 4)

The identification of factors in visceral endoderm that stimulate blood development and vascular growth is here demonstrated through the use of novel assays. These assays include:

(a) the analysis of embryonic explant tissues prior, during and after blood development. For example, explants may be derived from blastocysts which are formed at the first stage of mammalian development. Blastocysts are formed when the embryo reaches the 64 cell stage forming an inner cell mass, an outer trophoblast cell layer formed from trophectoderm cells and an internal space containing fluid identified as the blastocoel. The inner cell mass (ICM) is situated in the blastocoel and becomes segregated into the "primitive endoderm" which forms the outer layer of the ICM, and the ICM itself. The "primitive endoderm" give rise to parietal and visceral endoderm. The internal ICM cells, which form the primitive ectoderm, gives rise to the embryo proper. Blastocysts, which are isolated before blood development is initiated, can be maintained in culture for periods of time that allow for the formation of tissues characteristic of organs associated with the vasculature such as beating cardiac muscle. Blood development is first observed histologically when blood islands are observed between the endoderm and the mesoderm of the developing embryonic yolk sac. Without being bound by theory, we believe that the observed islands are formed as a result of the formation of erythroblasts and endothelial cells from undifferentiated precursor cells. In the experimental mouse model, embryonic explants may be isolated at or after 2 dpc before blood island formation is observed and may be maintained in vitro up to 14 dpc and longer when organ development is in progress, providing a model system for following the initiation and progression of blood and the vascular system. Isolation of explants prior to formation of blood according to the invention is novel with respect to the prior art, where the prior art describes events in blood development after initiation of blood island formation has already occurred. (Cumano et al. (1996), Palis et al., Blood 86 (1995), 160–63, Kanatsu et al., *Development* 122 (1996), 23–30).

(b) The use of explants from transgenic animals in which the regulatory region of an early stage gene product associated with blood formation (for example ϵ-globin gene) is coupled to a marker, such that the marker (for example LacZ) serves to signal the onset of hematopoiesis and vascular growth [Example 1]. Onset of hematopoiesis or vascular growth can be detected using sensitive detection methods such RT-PCR which can detect initiation of expression and the extent of expression of gene products that are associated with blood development; histochemical staining exemplified by benzidine staining of hemoglobin; immunohistochemistry that utilizes an antibody of appropriate specificity; whole mount in situ hybridization; in situ hybridization using radiolabelled riboprobes and other detection methods known in the art.

Four different assay designs are described below and in Examples 1 and 2 which have utility both individually and in combination for screening and identifying factors involved in hematopoiesis and vascular growth.

(i) Epiblast cultures: Intact embryo explants were harvested prior to the histological appearance of blood islands for example at 6.5 dpc, and incubated intact in vitro using standard culture techniques so as to permit development of the embryo to continue thereby serving as positive controls of blood formation. (Example 2A–B). In these circumstances, the explants formed blood islands in vitro and blood formation could be followed by measuring the appearance of markers of early blood development such as ϵ-globin,(embryonic β-globin) GATA-1, CD 34, sca-1 (markers of hematopoietic stem cells) PECAM-1, flk-1, Vezf-1 (endothelial marker). In Example 2, ϵ-globin gene expression was detected after a 72 hr incubation in vitro in epiblast cultures using RT-PCR. Embryos explanted from transgenic animals, carrying the LacZ marker under the ϵ-globin gene promoter, stained with XGal after a similar time period.

Figures 2A, 7:
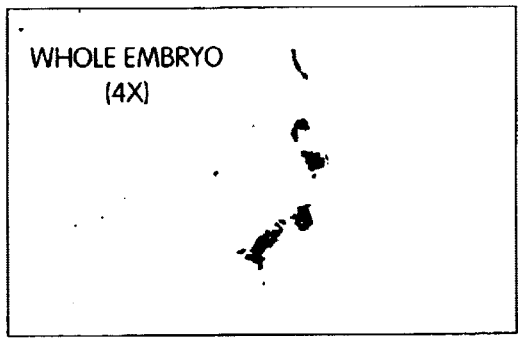
Figures 2B, 7:
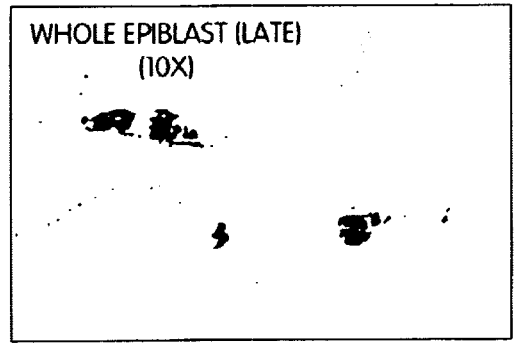
Figures 2C, 7:
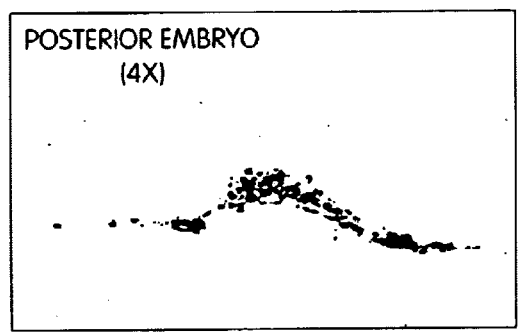
Figures 2D, 7:
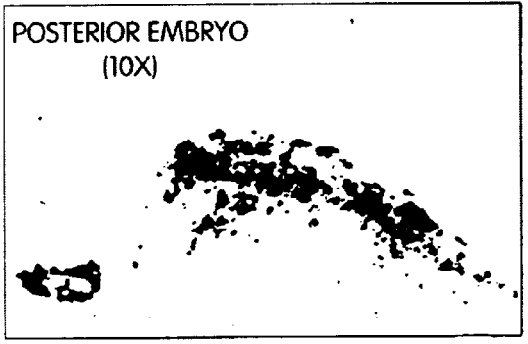
Figures 2E, 7:
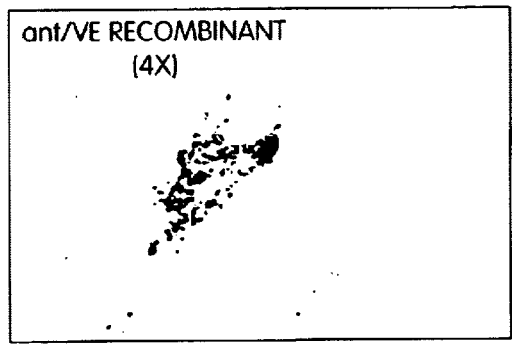
Figures 1A, 8:
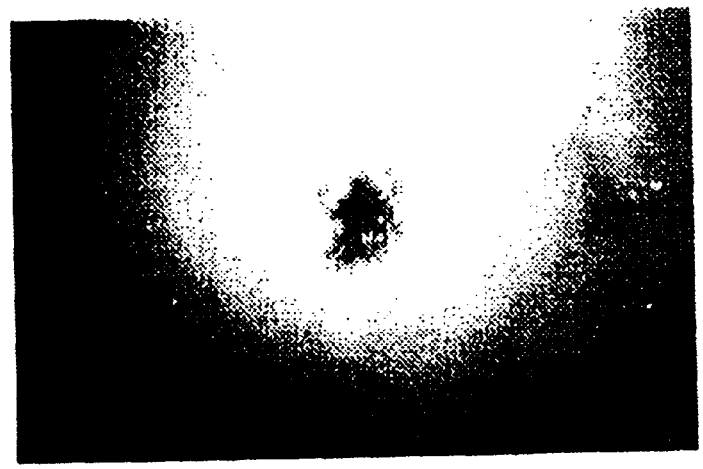
Figures 1B, 8:
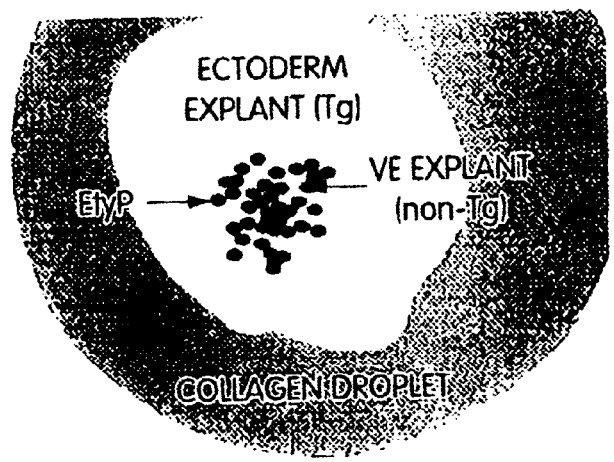
Figures 1C, 8:
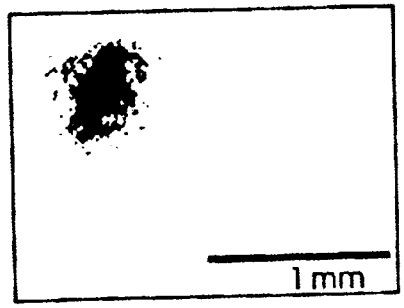
Figure 10:
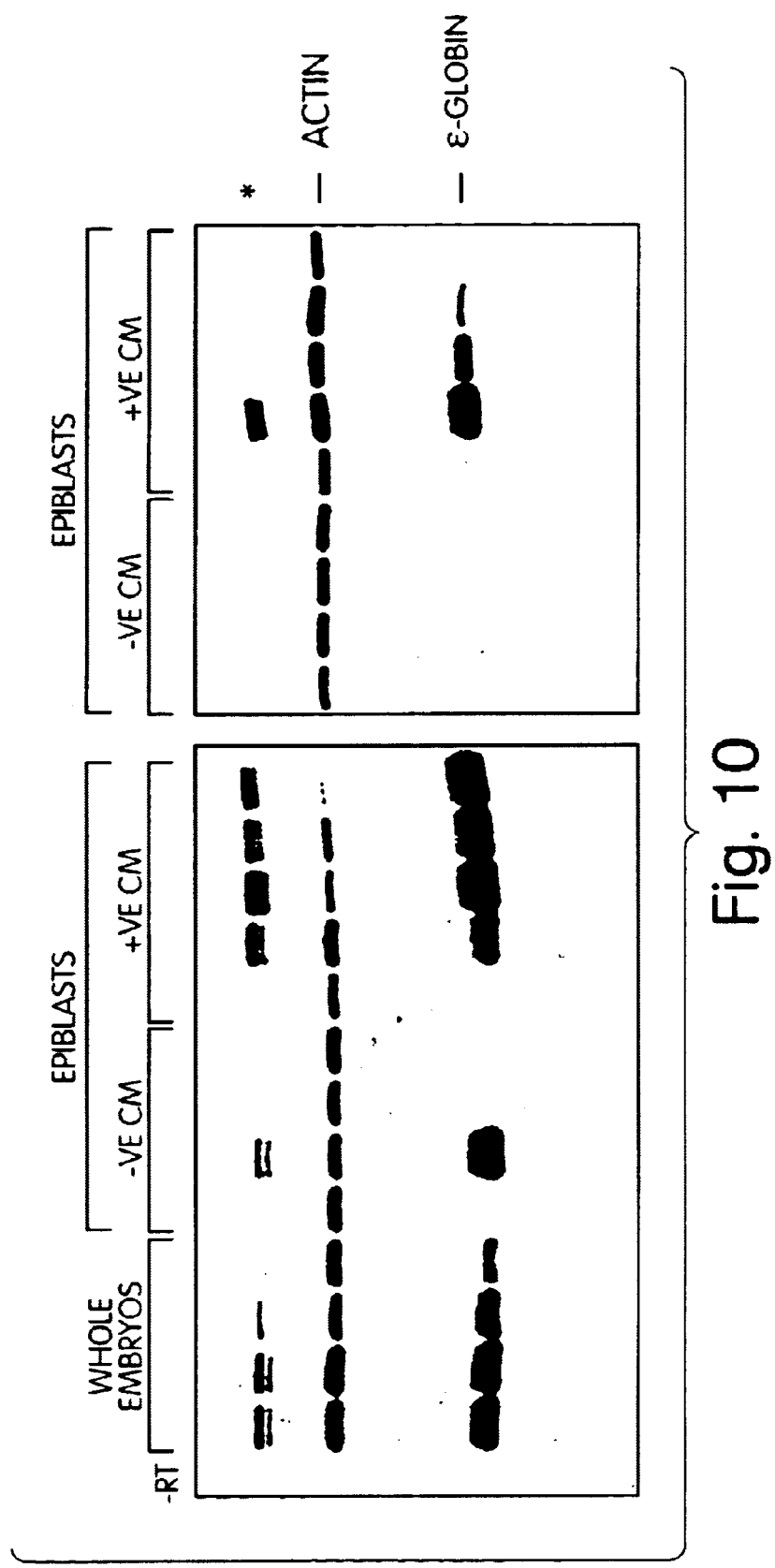
FIG. 10 shows the activation of primitive erythropoiesis by a diffusible factor in visceral endoderm cells by means of RT-PCR analysis.

The assay includes the creation of embryo explants that are not capable of producing blood islands, where this incapacity is reversible. When embryos were first stripped of the visceral endoderm, the resulting epiblasts failed to stain positively with XGal in explant cultures and therefore failed to express ϵ-globin (FIGS. 7, 8). Diffusible factors have been identified that modulate the initiation of hematopoiesis in a manner independent of direct cell—cell contact. These factors are made outside of the epiblast, for example, in the visceral endoderm. The biological role of these factors was confirmed by reconstitution experiments using visceral endoderm and epiblast tissues (FIG. 8). The requirement for factors contained in the visceral endoderm was further demonstrated when we compared the effect of treating epiblasts with conditioned medium obtained from visceral endoderm cell cultures compared with control untreated epiblasts (Example 2A). Whereas, in the absence of conditioned medium, epiblasts did not express ϵ-globin, the addition of conditioned medium containing secreted cell factors induced the expression of ϵ-globin in the embryonic tissue (FIG. 10). Epiblasts derived from non-transgenic mice were analyzed for gene expression using whole-mount in situ hybridization or immunostaining.

Figure 13:
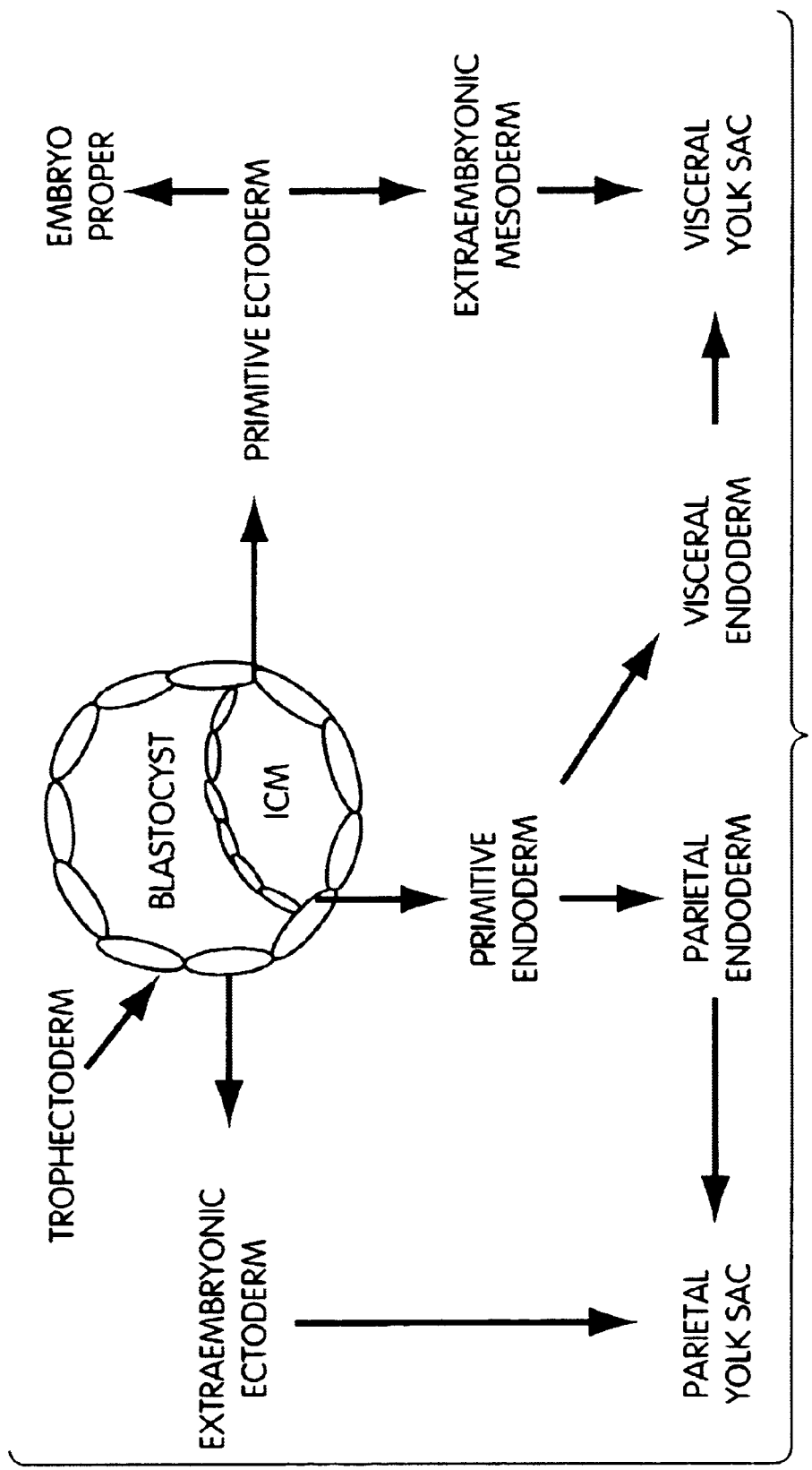
FIG. 13 shows the derivation of cell lineages in the mammalian embryonic yolk sac. The circular structure represents a blastocyst of around 3.5 days.
Figure 14A:
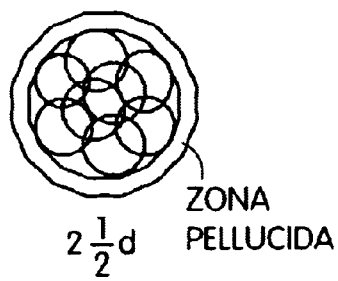
FIGS. 14A through 14F show the early development of the mouse at 2.5 dpc (A), 3.5 dpc (B), 4.5 dpc (C), 5.5 dpc (D), 6.5 dpc (E), and 7.5 dpc (F). The region of early blood island formation occurs in the exocoelomic cavity (see F) between the epiblast below which is surrounded by the visceral endoderm and the extraembryonic tissue above.
Figure 14B:
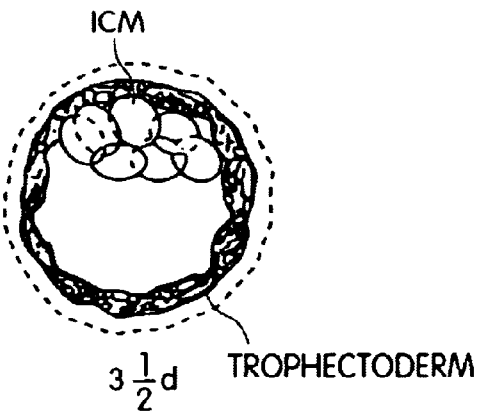
Figure 14C:
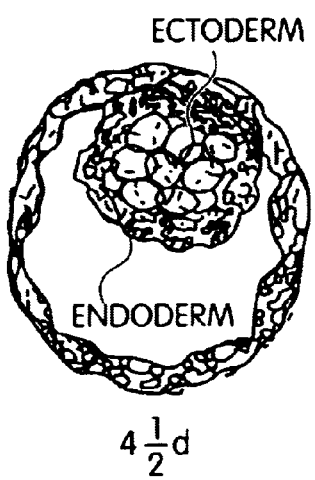
Figure 14D:
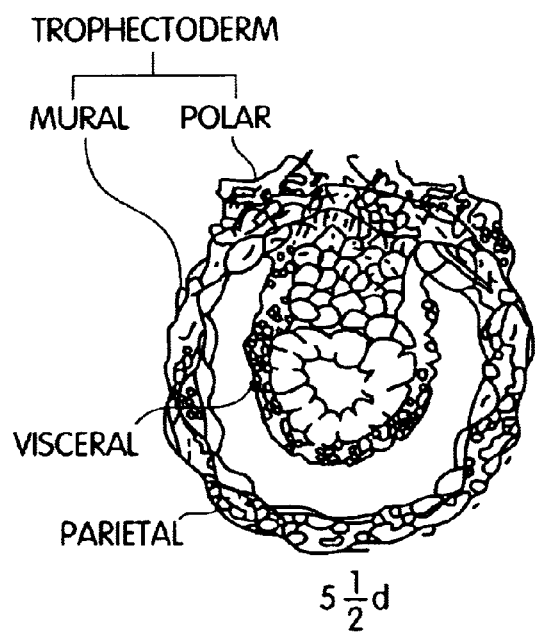
Figure 14E:
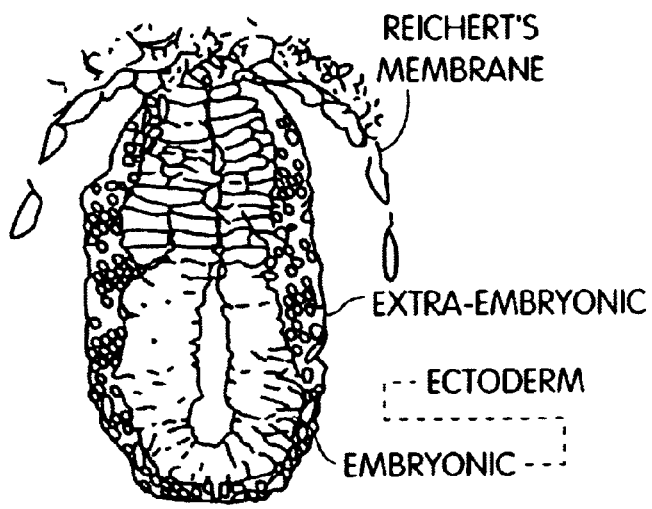
Figure 14F:
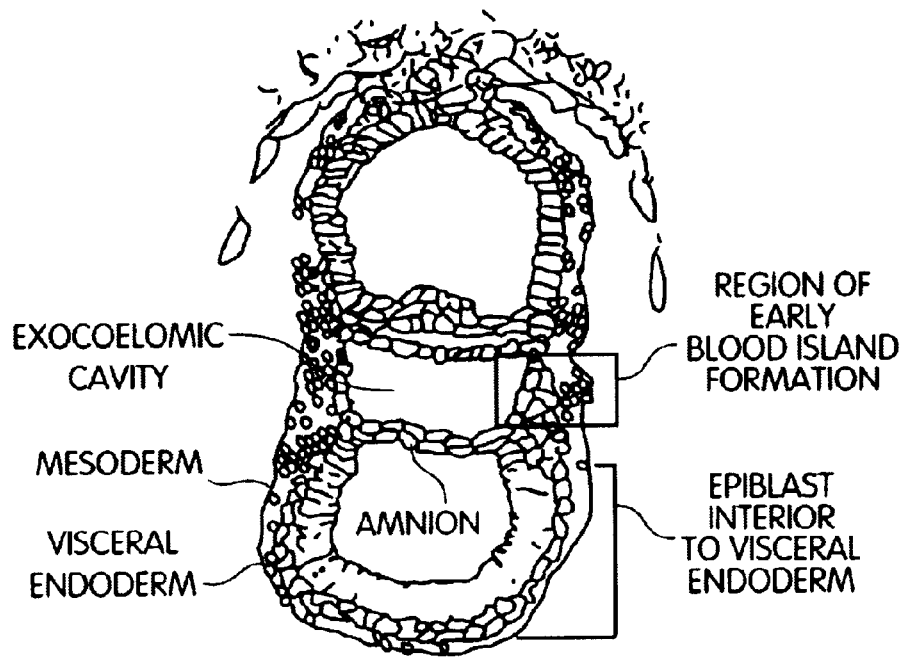

(ii) Blastocyst cultures: The expression of XGal in blastocysts derived from transgenic mice containing a hybrid gene formed from a detectable marker controlled by regulatory sequences of a gene associated with blood formation such as embryonic β-like: LacZ globin (ϵ-globin: LacZ) was measured. In Example 2(C), blastocysts were isolated at 3.5 dpc and incubated for a further 7–10 days. (FIG. 13) Alternatively, blastocyst cultures have been prepared as above using non-transgenic mice and gene expression has been detected by whole mount in situ hybridization or immunostaining. Details of blastocyst cultures are provided in Example 2(C) and in FIG. 3.

(iii) Modified epiblast culture assays: Late stage gastrulating embryos have been harvested and epiblasts prepared by dissecting away the extraembryonic ectoderm (Example 2(B)). During gastrulation, embryonic cells establish the basic body plan and extraembryonic mesoderm contribute to the extraembryonic tissues, respectively. Mesoderm cells destined for extraembryonic sites exit the posterior primitive streak and subdivide the embryo into three separate cavities by the late streak stage at 7.5 dpc. The central cavity, the exocoelom, becomes completely lined with mesoderm cells. These mesoderm cells lie adjacent to the embryonic ectoderm to form the amnion, the extraembryonic ectoderm to form the chorion and the visceral endoderm to form the visceral yolk sac (VYS). At the end of gastrulation, the cells in the embryo have separated into three germ layers: the outer ectoderm, giving rise to the epidermis and the nervous system; the inner endoderm, giving rise to the lining of the digestive tube and its associated organs (such as pancreas, liver, and spleen); and the intermediate mesoderm, giving rise to several organs (heart, kidney, gonads), connective tissue (bone, muscle, tendons) and the definitive blood cells.

Figures 1, 16:
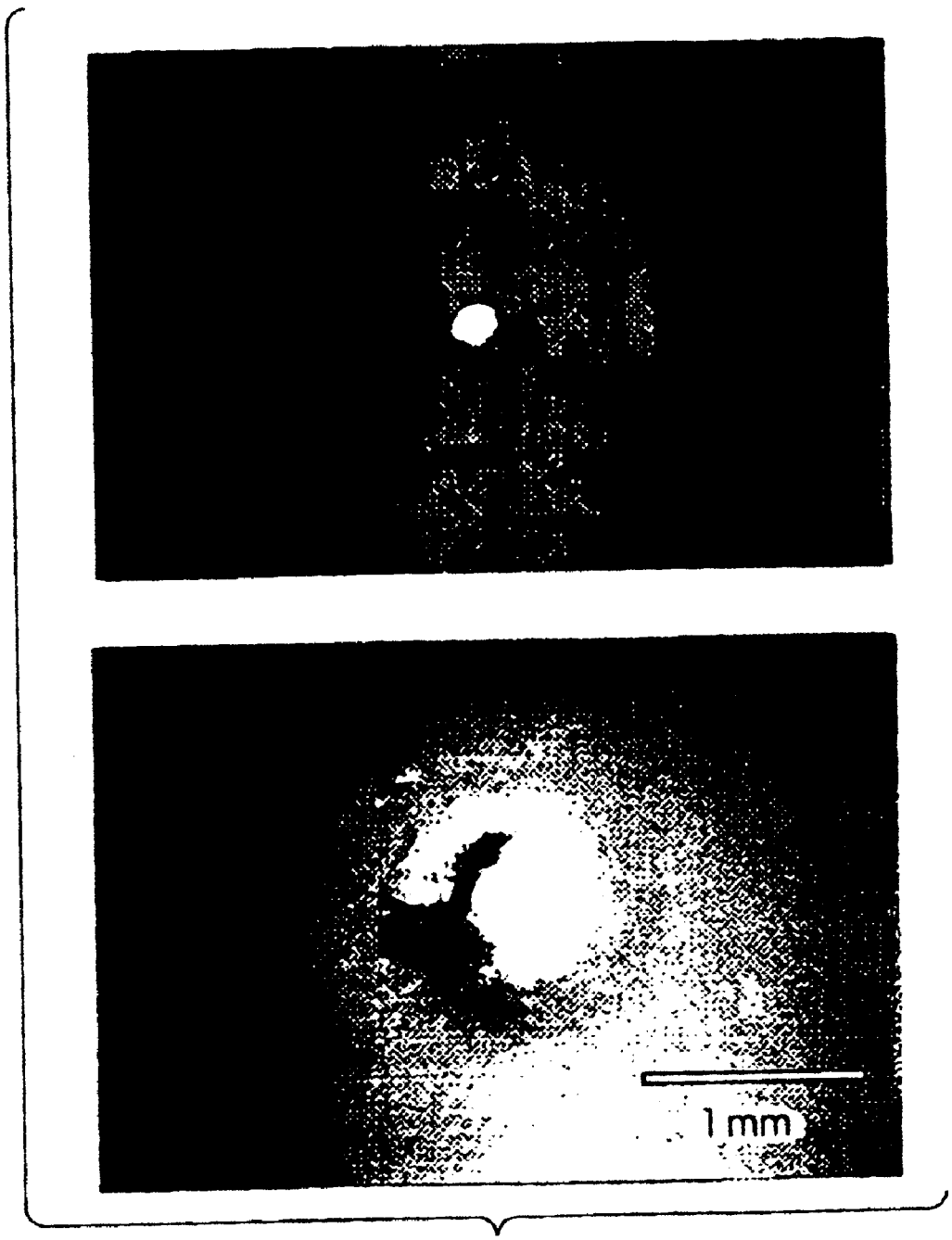
Figures 2, 16:
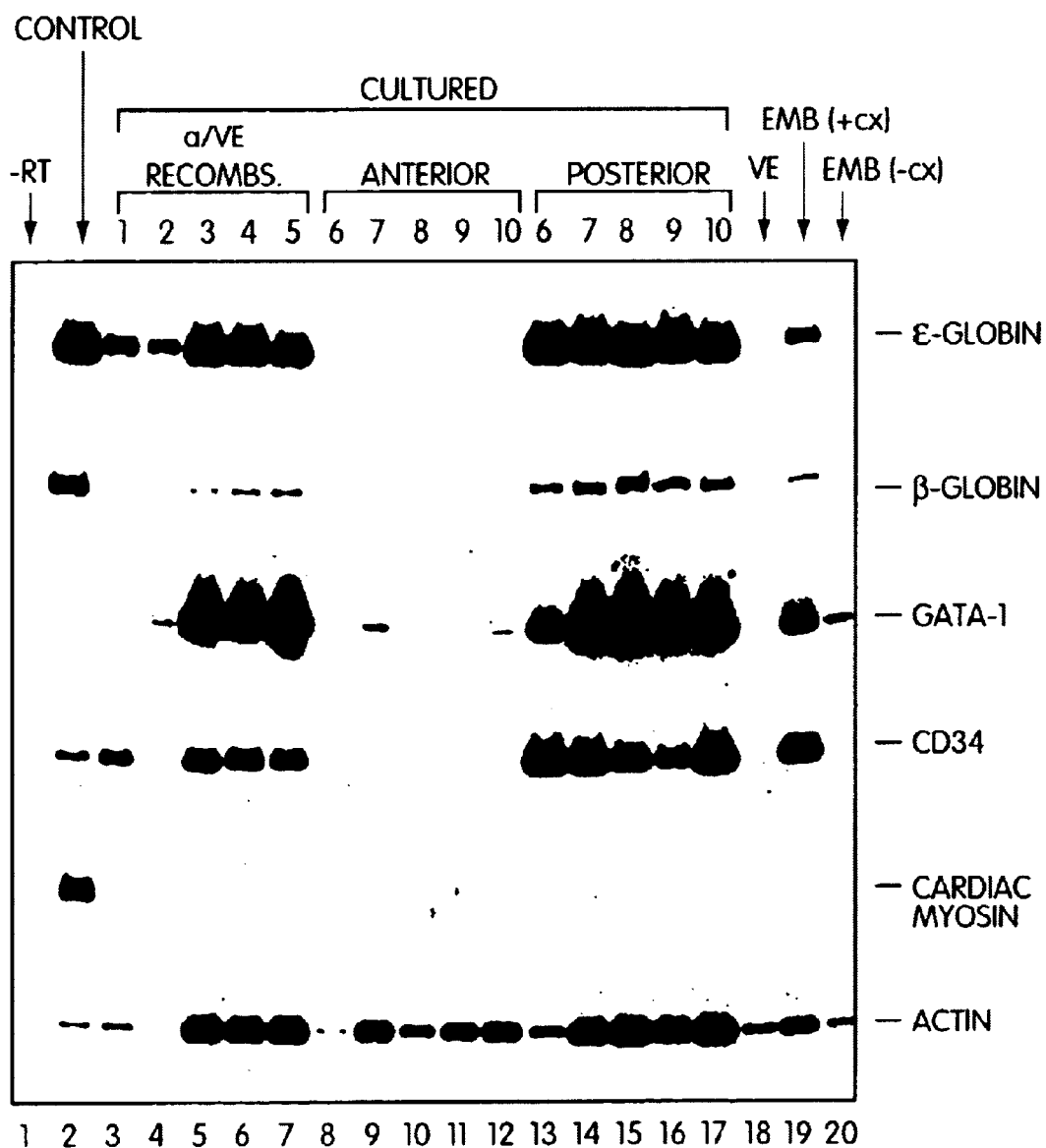

Single epiblasts from late stage gastrulating embryos were transected into anterior and posterior portions and each portion was cultured individually for several days (FIGS. 14 and 15). While the anterior epiblast portion formed little or no blood islands as determined by expression of $\epsilon$-globin using RT-PCR techniques, the posterior portions formed blood at levels comparable to the intact epiblast. Using this assay, compositions may be added to the anterior epiblast and the stimulation of blood formation determined. The control in this assay is the addition of visceral endoderm which is sufficient to cause the anterior epiblast to form blood islands. When either visceral endoderm or hedgehog protein was added to the culture, blood formation was observed. (FIG. 16)

(iv) Explants or embryoid bodies derived from mutants defective in targeted protein: Embryoid bodies are formed from harvested embryonic stem cells that are incubated in vitro using techniques well known in the art. (Example 2(C)) These cells form embryoid bodies that contain several cell types including blood cells and endothelial precursor cells (see FIG. 17(A, C). Embryonic stem cells may be subjected to targeted mutations in selected mouse genes, which products play a role in hematopoiesis and vascular growth, using well established techniques such as homologous recombination and selectable drug resistance, resulting in cells that are homozygous for the targeted gene mutation. Mutations may be induced that (i) "knock out" a coding gene or regulatory sequence; (ii) "knock out" a coding gene or regulatory sequence and replace the sequence with a "knock-in" sequence that causes something else to be made (the knock-in sequence may be a mutated sequence); or (iii) generate a random mutation by insertion of foreign DNA into the genome or use of chemicals to cause mutations. The consequences of forming such mutations include: modifying the activity of a particular gene product and nullifying the activity of the gene product and may further include substitution of a gene product with another gene product by established methods of genetic manipulation.

Where these targeted mutations result in no gene expression of the protein, the mutations are called null mutations. Null mutants were formed using wild type embryonic stem cells. According to the invention, null mutants defective in a protein that is associated with the visceral endoderm such that its absence results in the failure to make blood, is a suitable model system for screening novel compounds from libraries such as those derived from extraembryonic tissues, where these libraries include combinatorial peptide libraries and recombinant DNA libraries. By using a pooling strategy to reduce the number of experimental tests, compounds may be identified that are useful in modulating hematopoiesis and vascular growth in embryoid bodies.

This general type of assay can be used to study the effect of other mutations, such as deficiency of signaling factors such as hedgehog proteins (for example, Indian hedgehog), on blood formation.(Examples 3–5) For example, Ihh null mutant ES cells may be formed and factors capable of overcoming the mutation, identified. These cells could be rescued either by providing exogenous hedgehog protein or by transfecting the cells with vectors expressing a hedgehog gene utilizing standard vectors or retroviral vectors. (FIG. 9) The mutated cells could also be reintroduced into mice to form chimeras.

Figures 2, 8:
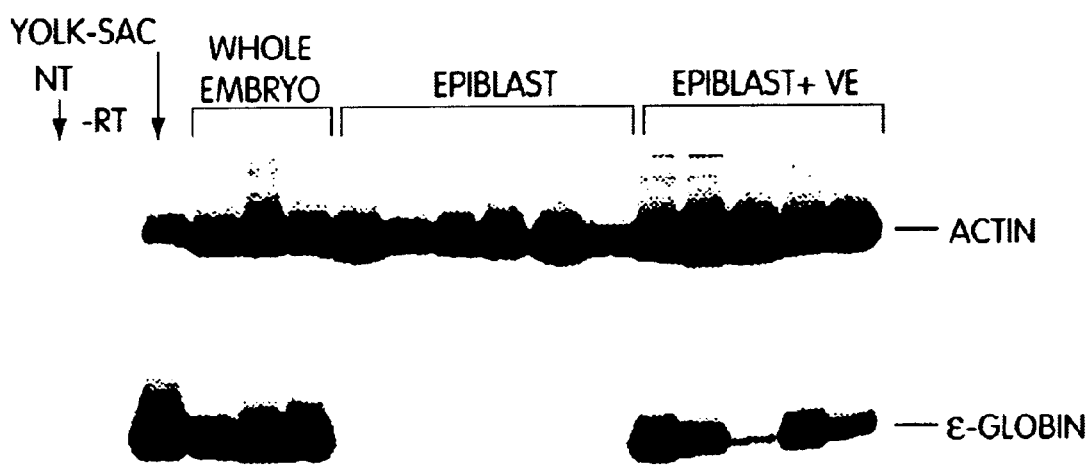

These detection techniques were used to detect hematopoiesis and vascular growth in epiblasts and blastocyst cultures as follows: According to the assay of the invention, the onset of blood island formation may be detected using any of the sensitive techniques available in the art, including the following:

(1) Detection of XGal in explants derived from transgenic mice that contained the hybrid gene-embryonic $\beta$-like: LacZ globin ($\epsilon$-globin: LacZ). The embryos of homozygous transgenic mice were analyzed using XGal to reveal globin gene transcription indicative of blood development prior to visual detection of erythroid cells (FIGS. 1, 2)

Figure 4:
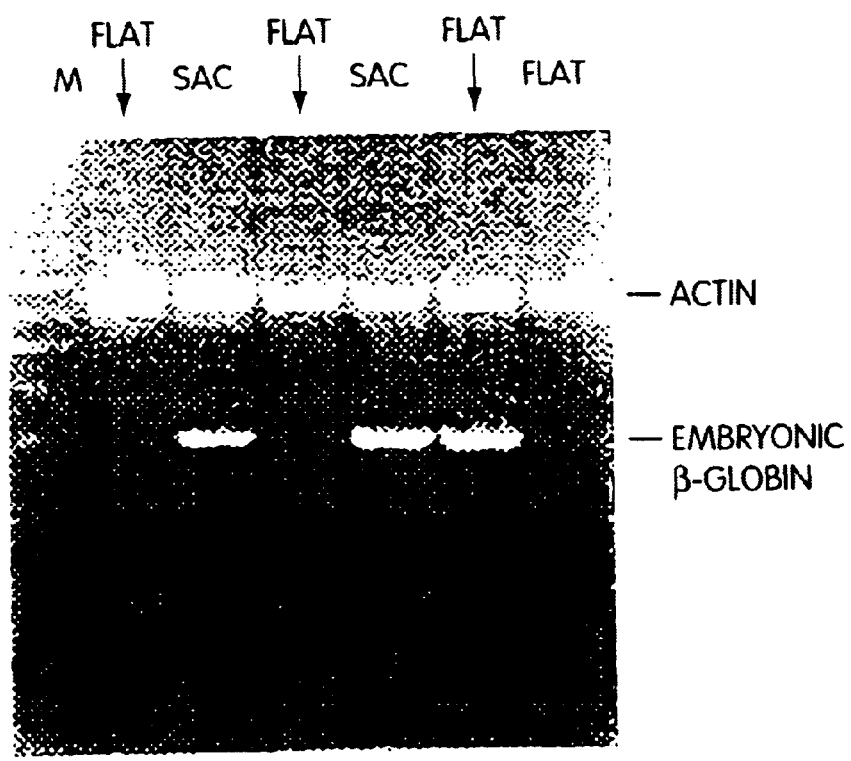
FIG. 4 shows RT-PCR analysis of blastocyst cultures: $\epsilon$-globin was observed in blastocysts that have developed into sac-like structures (sac) but not in samples that were relatively flat mounds of cells (flat). The higher molecular weight band is the internal control-actin. The lower molecular weight band is embryonic $\beta$-globin.

(2) Detection of globin gene expression using radioactive semi-quantitative RT-PCR probes in epiblasts and blastocysts at various times post conception. A distinct advantage of using a radioactive assay is that the amount of tissue recovered from individual explants is very small, and a sensitive assay makes it possible to assay for expression of many genes from a single culture product. (FIG. 4)

Using the above assays, we have identified a number of compounds that are functionally equivalent to gene products that are expressed in extraembryonic tissues and may stimulate blood formation. These compounds include TGF-$\beta$ proteins more specifically TGF-$\beta$1 more specifically bone morphogenic protein (BMP) more specifically BMP-4; tumor necrosis factor (TNF) proteins more specifically TNF-$\alpha$; wnt family; and hedgehog proteins. (FIGS. 5, 9 and 17) Compounds may also include naturally occurring and synthetic agonists, antagonists, analogs and derivatives of the above. These molecules may interact with membrane proteins which initiate signal transduction pathways resulting in a biological response. Therefore, in addition to the above compounds, agonists and antagonists to these membrane binding proteins including those receptors, receptor agonists and receptor antagonists associated with hedgehog binding receptors and hedgehog signalling transduction pathways such as smoothened, patched and gli may have utility in regulating hematopoiesis and vascular growth.

The target site for stimulating stem cell proliferation and modulating differentiation is here identified as predifferentiated mesodermal derived tissue such as is present in the embryo. Embryonic predifferentiated mesodermal tissue includes visceral yolk sac, allantois, amnion, chorion, trophectoderm and prenatal yolk sac, hematopoietic stem cells in fetal liver and umbilical cord blood. Predifferentiated mesodermal derived tissue in the adult includes hematopoietic stem cells and progenitor cells in adult bone marrow, liver and spleen and endothelial stem cells and progenitor cells in the fetus and adult.

The novel assays of the invention are capable of use in multiple applications, including:
(i) screening libraries of compounds for activity in stimulating hematopoiesis and vascular growth;

(ii) testing for the effect of growth factors, cytokines and other signaling molecules on embryonic hematopoiesis and also on vascular growth;

(iii) determining the effect of hedgehog proteins on hematopoiesis and vascular growth in the embryo, fetus and adult. For example, the blastocyst assay may be used to determine the effect of hedgehog proteins on yolk sac development ex vivo where the blastocyst is derived from transgenic or non-transgenic animals.

(iv) examining the hematopoietic potential of other embryonic tissues such as the allantois which does not normally produce blood cells but whose mesoderm is of the same origin as that of the yolk sac;

(v) following the development of primitive erythroid cells and vascular structures by staining with a marker such as XGal so as to outline the vasculature and permit the tracking of vascular growth as well as hematopoiesis; and provides the means for analyzing early intraembryonic definitive hematopoiesis as well as primitive yolk sac hematopoiesis;

(vi) determining the effect on individual explants of targeted mutations in genes that affect hematopoiesis or vascular growth in the parent animal including those carrying transgenes expressing hedgehog, patched, Gli and other proteins; and (vii) examining the effect of gene therapy on mesodermally derived tissues; where for example, the gene for hedgehog protein is introduced into prestreak embryos deprived of the visceral endoderm, under various promoters so as to modulate the effect of blood island formation. This type of gene therapy model may serve as an experimental tool for identifying molecules capable of modulating hematopoiesis and vascular growth.

Figure 6:
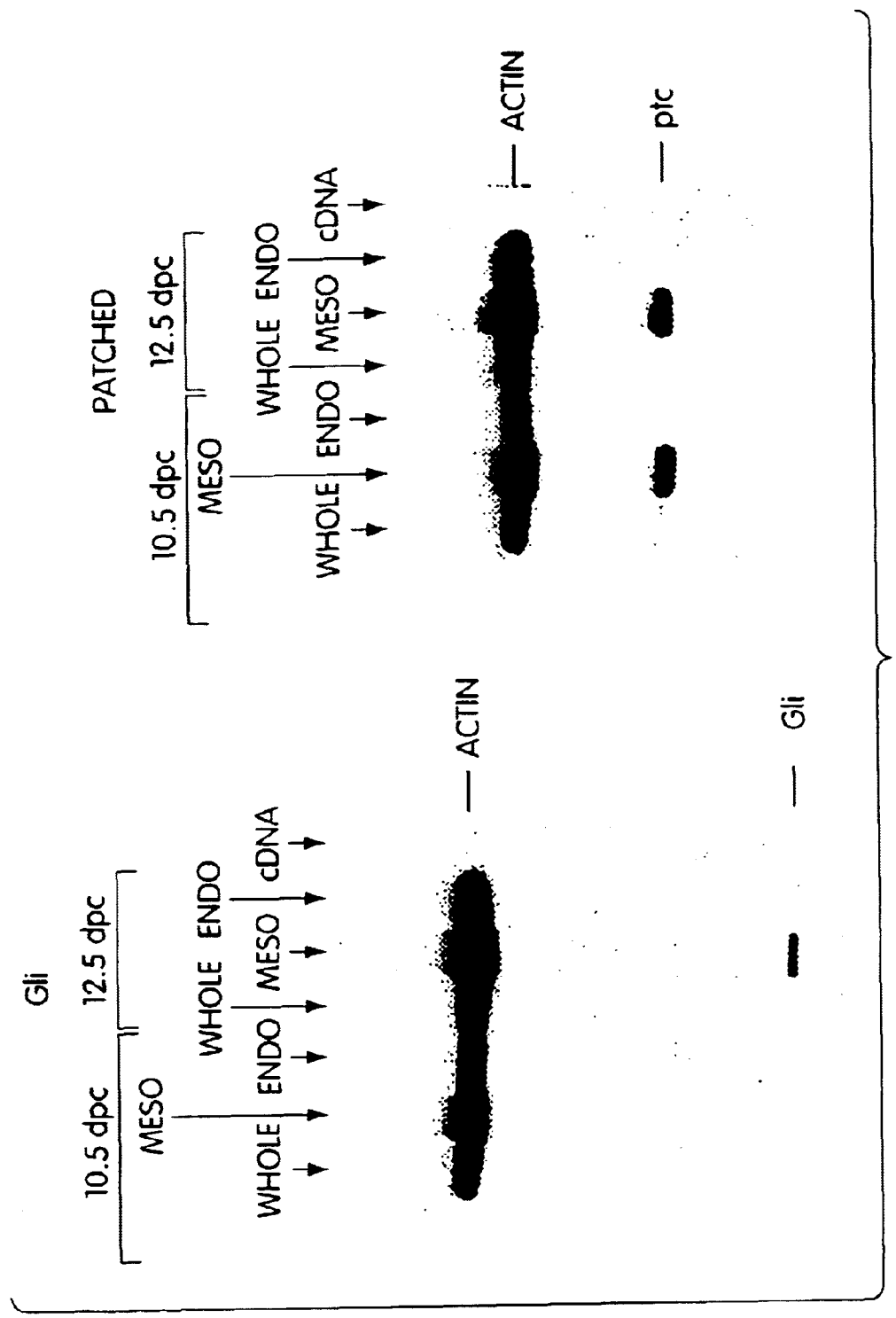
FIG. 6 shows differential expression of patched (ptc) and Gli genes in dissected yolk sac mesoderm at 10.5 dpc and 12.5 dpc by means of RT-PCR analyses, revealing substantially exclusive expression of Gli and ptc in dissected yolk sac mesoderm: whole, undissected yolk sacs; meso, mesoderm layer; endo, endoderm layer; –cDNA, minus cDNA control. Actin served as an internal control.

The newly identified role of morphogenic proteins in hematopoiesis and vascular growth:

Hedgehog proteins: We have shown here for the first time that hedgehog proteins are capable of stimulating hematopoiesis in the yolk sac, and the splanchnopleura and other hematopoietic tissues of the embryo or fetus and of stimulating hematopoiesis in the bone marrow of the adult. (Examples 3–5, Tables 1–2, FIGS. 6, 9). By screening for molecules that were present in the visceral endoderm, we identified hedgehog gene product. When a hedgehog protein (SHH) was added to epiblast cultures and RNA was isolated after 2–3 days and analyzed by RT-PCR (Example 3, FIG. 9), hematopoiesis was observed to be stimulated, as determined by the activation of the $\epsilon$-globin gene. Furthermore, SHH protein was capable of stimulating hematopoiesis in the epiblast absent the visceral endoderm. When antibodies to SHH were added to whole embryos, as described in Example 4, and FIG. 11, $\epsilon$-globin expression was substantially reduced.

The above assays show that hedgehog proteins expressed in extraembryonic tissue as well as hedgehog proteins that are closely related to proteins expressed in extraembryonic tissues, stimulate hematopoiesis and vasculogenesis. Members of the hedgehog family which are a distinct family of signaling molecules (e.g., reviewed in Goodrich et al., *Genes & Develop.* 10 (1996), 301–12) are known to play a role in limb morphogenesis, neural development, bone modeling and spermatogenesis. The family was initially identified as involved in normal segmental patterning in Drosophila (Nusslein-Volhard et al, *Nature,* 287 (1980), 795–801). The hedgehog family includes Desert hedgehog (DHH) protein, Indian hedgehog protein (IHH), Moonrat hedgehog (Zebrafish) and Tiggy winkle hedgehog (Zebra fish).

Although the invention is not intended to be limited by theories, we suggest that the initial expression of IHH in visceral endoderm may result in activation of DHH later in the yolk sac mesoderm and that DHH may act on the extraembryonic mesoderm of the yolk sac in an autocrine manner. In this way, epiblasts stripped of visceral endoderm at 6.5 dpc may produce blood islands at 7.5 dpc in the presence of IHH acting on DHH signaling. Once DHH signaling is initiated in this way, IHH may no longer be absolutely required. We have observed the effect of IHH knockout or DHH knockout alone or together. We note that the DHH knock-out does not prevent the formation of blood islands and conclude that IHH has a continued stimulating effect on blood development in the absence of DHH. We suggest that both IHH and DHH would need to be knocked out to result in a yolk sac phenotype lacking blood cells and vasculature. The apparent functional differences in the molecules themselves may not reside so much in their biochemical differences but rather may follow from differences in the site of expression or the timing of expression. A precedent for this is provided by the engrailed genes (Hanks, et al., *Science,* 269 (1995), 679–82). The propositions presented above represent the preferred explanations for the relationship of DHH and IHH but are not meant to exclude other explanations for the observed associations between these proteins.

The utility of the hedgehog proteins in stimulating hematopoiesis and vascular growth is further reinforced by our experiments on target molecules through which these proteins act. Using RT-PCR to analyze expression of patched and Gli, (Example 5, FIG. 6) we identified substantially exclusive expression of these proteins in the yolk sac mesoderm, a tissue whose sole function is to produce blood and vascular endothelial cells.

In support of our observations that hedgehog proteins are capable of stimulating hematopoiesis, we identified the enriched expression of Gli and patched in yolk sac mesoderm. Gli is a transcription factor involved in the transduction pathway on which hedgehog proteins act, while PTC (patched) is a membrane protein that binds hedgehog protein to initiate the signal transduction pathway that ultimately causes a biological response in the target cell. The association of these proteins with yolk sac mesoderm further supports the observation that hedgehog proteins stimulate hematopoiesis. Since ptc is the presumed gateway to a cell response, any agonist of hedgehog capable of binding patch is expected to induce the same biological effect as hedgehog—in this case, hematopoiesis and vascular growth.

Certain hedgehog proteins have been reported to be involved in the initiation of expression of the secondary signaling molecules-BMP-2 and BMP-4 (proteins belonging to the TGF-$\beta$ family) in the mesoderm and Fgf-4 in the ectoderm (WO 95/18856). We have identified for the first time, that hedgehog proteins might interact in a synergistic manner with secondary signaling molecules to stimulate hematopoiesis and vascular growth (Example 6). These signaling molecules include BMP-2, BMP-4, BMP-6 and BMP-7 and other members of the TGF-$\beta$ family including Wnts and FGF, which may be found to be associated with the visceral endoderm and/or the yolk sac mesoderm.

The activity of compounds that are functional equivalents to a gene product expressed in extra-embryonic tissue such as recombinant hedgehog protein, analogs, derivatives and disassociation products of hedgehog proteins, and agonists of hedgehog protein receptors such as PTC according to the invention, may stimulate hemotopoiesis and vascular growth by acting on cells or tissues from embryos of different ages including fetal cells, fetal peripheral blood and cord blood, as well as on adult hematopoietic stem cells and adult progenitor cells. The invention includes the use of functional peptides of hedgehog protein. The term "functional peptide" as a subclass of a hedgehog compound defined above, is meant to include peptide fragments of the hedgehog protein that are capable of inducing a biological activity that is the same or equivalent to the entire protein (WO 96/16668, incorporated here by reference).

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent with one of vertebrate hh sequences of the present invention.

Homologs of one of the subject hedgehog proteins can be generated by mutagenesis such as by discrete point mutation (s) or by truncation. For instance, mutation can give rise to homologs which retain substantially the same, or merely a subset, of the biological activity of the hh polypeptide from which it derived. Alternatively, antagonistic forms of the protein can be generated which are able to inhibit the function of the naturally occurring form of the protein, such as by competitively binding to the hh receptor.

Peptides referred to herein as having an activity of a vertebrate hh protein are defined as peptides that have an amino acid sequence corresponding to all or a portion of the amino acid sequences of a vertebrate hh protein which have at least one biological activity of a vertebrate hh protein.

The invention further includes hedgehog compounds described in WO 95/18856 and here incorporated by reference, including homologs of hedgehog proteins, recombinant hedgehog proteins, hedgehog encoding nucleic acids, antisense molecules, gene constructs for use in gene therapy including viral vectors known in the art, combinatorial mutants of hedgehog proteins as agonists or antagonists, and antibodies specific for hedgehog protein epitope. These and other compounds may be selected for modulating hematopoiesis and vascular growth according to the assays of the invention.

The Hedgehog family of vertebrate inter-cellular signaling molecules described in WO 95/18856 consists of at least four members. Three of these members, herein referred to as Desert hedgehog (Dhh), Sonic hedgehog (Shh) and Indian hedgehog (Ihh), exist in all vertebrates, including fish, birds, and mammals. A fourth member, herein referred to as Moonrat hedgehog (Mhh), appears specific to fish. According to the appended sequence listing, (see also Table 1) a chicken Shh polypeptide is encoded by SEQ ID No: 1; a mouse Dhh polypeptide is encoded by SEQ ID No: 2; a mouse Ihh polypeptide is encoded by SEQ ID No: 3; a mouse Shh polypeptide is encoded by SEQ ID No: 4 a zebrafish Shh polypeptide is encoded by SEQ ID No: 5; a human Shh polypeptide is encoded by SEQ ID No: 6; and a human Ihh polypeptide is encoded by SEQ ID No: 7.

TABLE 1

Guide to vertebrate hedgehog sequences

|  | Nucleotide | Amino Acid |
| --- | --- | --- |
| Chicken Shh | SEQ ID No. 27 | SEQ ID No. 34 |
| Mouse Dhh | SEQ ID No. 28 | SEQ ID No. 35 |
| Mouse Ihh | SEQ ID No. 29 | SEQ ID No. 36 |
| Nouse Shh | SEQ ID No. 30 | SEQ ID No. 37 |
| Zebrafish Shh | SEQ ID No. 31 | SEQ ID No. 38 |
| Human Shh | SEQ ID No. 32 | SEQ ID No. 39 |
| Human Ihh | SEQ ID No. 33 | SEQ ID No. 40 |

SEQ ID No. 41 is the predicted degenerate sequence of the N-terminal portion of vertebrate hedgehog proteins.

In certain embodiments, the polypeptide is identical with or homologous to a Sonic hedgehog (Shh) polypeptide, such as a mouse or human Shh represented by SEQ ID Nos: 39 or 37, an avian Shh represented by SEQ ID No: 34, or a fish Shh represented by SEQ ID No: 38. For instance, the Shh polypeptide preferably has an amino acid sequence at least 70% homologous to a polypeptide represented by any of SEQ ID Nos: 34, 37, 38 or 39, though polypeptides with higher sequence homologies of, for example, 80%, 90% or 95% are also contemplated. Exemplary Shh proteins are represented by SEQ ID No. 42. The Shh polypeptide can comprise a full length protein, such as represented in the sequence listings, or it can comprise a fragment of, for instance, at least 5, 10, 20, 50, 100 or 150 amino acids in length. Preferred hedgehog polypeptides include Shh sequences corresponding approximately to the natural proteolytic fragments of the hedgehog proteins, such as from about Cys-24 through Glu-188, or from about Asn-189 through Ala-475 of the human Shh protein, or analogous fragments thereto.

In other embodiments, the polypeptide is identical with or homologous to an Indian hedgehog (Ihh) polypeptide, such as a human Ihh represented by SEQ ID No: 40, or a mouse Ihh represented by SEQ ID No: 36. For instance, the Ihh polypeptide preferably has an amino acid sequence at least 70% homologous to a polypeptide represented by either of SEQ ID Nos: 36 or 40, though Ihh polypeptides with higher sequence homologies of, for example, 80%, 90% or 95% are also contemplated. The polypeptide can comprise the full length protein represented by in part by these sequences, or it can comprise a fragment of, for instance, at least 5, 10, 20, 50, 100 or 150 amino acids in length. Preferred Ihh polypeptides comprise an N-terminal fragment including Arg-1 through Glu-94, or a C-terminal fragment including His-95 through Ser-3312 of the human Ihh represented by SEQ ID No: 40, or analogous fragments thereto.

In still further embodiments, the polypeptide is identical with or homologous to a Desert hedgehog (Dhh) polypeptide, such as a mouse Dhh represented by SEQ ID No: 35. For instance, the Dhh polypeptide preferably has an amino acid sequence at least 70% homologous to a polypeptide represented by SEQ ID No: 35, though Dhh polypeptides with higher sequence homologies of, for example, 80%, 90% or 95% are also contemplated. The polypeptide can comprise the full length protein represented by this sequence, or it can comprise a fragment of, for instance, at least 5, 10, 20, 50, 100 or 150 amino acids in length. Preferred Dhh polypeptides comprise Dhh sequences corresponding to the N-terminal portion of the protein, e.g. Cys-23 through Asp-189 or Asn-190 through Gly-396 of SEQ ID No: 35, or analogous fragments thereto.

Hedgehog compounds described in WO 95/18856 include polypeptides encoded by a nucleic acid which hybridizes under high or low stringency conditions to a nucleic acid represented by one of SEQ ID Nos: 27–33. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Polypeptides encoded by nucleic acids having a sequence that differs from the nucleotide sequences shown in one of SEQ ID Nos: 27–33 due to degeneracy in the genetic code are also within the scope of the invention. Such nucleic acids encode functionally equivalent peptides (i.e., a peptide having a biological activity of a vertebrate hh polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a vertebrate hh polypeptide. However, it is expected that DNA sequence polymorphisms that do lead to changes in the amino acid sequences of the subject hh polypeptides will exist among vertebrates. One skilled in the art will appreciate that these variations in one or more nucleotides (up to about 3–5% of the nucleotides) of the nucleic acids encoding polypeptides having an activity of a vertebrate hh polypeptide may exist among individuals of a given species due to natural allelic variation.

Active portions of the vertebrate hedgehog proteins encoded by fragments of the nucleic acids are also suitable for use in the present invention the invention. As used herein, a hedgehog gene fragment refers to a nucleic acid having fewer nucleotides than the nucleotide sequence encoding the entire amino acid sequence of a vertebrate hh protein represented in SEQ ID Nos: 34–40, yet which (preferably) encodes a peptide which retains some biological activity of the full length protein, e.g., the fragment retains the ability to induce formation and differentiation of the head, limbs, lungs, central nervous system (CNS), or mesodermal patterning of developing vertebrate embryo. Nucleic acid fragments within the scope of the present invention include those capable of hybridizing under high or low stringency conditions with nucleic acids from other species for use in screening protocols to detect other hedgehog homologs, as well as those capable of hybridizing with nucleic acids from human specimens for use in detecting the presence of a nucleic acid encoding a hedgehog protein, including alternate isoforms, e.g., mRNA splicing variants. Nucleic acids within the scope of the invention may also contain linker sequences, modified restriction endonuclease sites and other sequences useful for molecular cloning, expression or purification of recombinant forms of the subject hh polypeptides.

According to the invention, these factors may be used to stimulate hematopoiesis and vascular growth in animals including mammals, including humans. Similarly antagonists to the compounds of the invention may be used to inhibit vascular growth and hematopoiesis. The therapeutic utility of these factors is discussed below.

Our novel blastocyst assay may be used to determine the effect of hedgehog proteins on yolk sac development. In addition, blastosacs could be assayed for gene expression not only using LacZ as a histochemical marker, but also by whole-mount in situ hybridization or by immunostaining.

Transgenic Mouse Models for Studying the Effect of Selected Compounds on Hematopoiesis and Vascular Growth:

Transgenic mouse models have utility in the study of developmental events. When a histological marker gene is introduced into the genome of mice, patterning associated with marked cells can be established.

The transgenic mice of the prior art have at least four major limitations: (i) the ability to follow transcription of the transgene relies on RNase protection or S1 nuclease assays of mRNA production, and tissue samples may be limiting at earlier developmental stages; (ii) the specificity of expression cannot be examined at the single cell level (short of performing in situ hybridizations using riboprobes, but these experiments are technically challenging and expensive); (iii) unbalanced expression of an exogenous β-globin gene in the absence of a counterbalancing α-globin gene is likely to lead to severe thalassemia (Hanscombe, et al., *Genes & Develop.* 3 (1989), 1572–81) and is thought to reduce the yield of transgenic progeny through early death in utero (Hanscombe et al., 1989; Pondel et al. *Nucleic Acids Res.* 20 (1992), 5655–60.). (iv) use of the entire globin gene with its upstream regulatory sequences, in transgenic mice and examination of mice after 8.5–9.5 dpc has resulted in analysis on blood development post initiation, Pondel, et al., (1992).

We have developed transgenic animals that provide models for blood development that overcame the limitations of the transgenic mice of the prior art. We have here adopted the use of selected mice models in which a marker gene is placed under the control of globin regulatory sequences to obtain explants suited to the assay as described above. We selected a marker, exemplified by β-galactosidase (LacZ) reporter gene, in place of the body of the ε-globin gene, so that functional exogenous hemoglobin protein would not be made and so that a sensitive enzymatic assay could be used to follow transgene expression. (Example 1) An additional advantage of using a reporter gene such as LacZ is that it allows for rapid, detailed histochemical studies in which the specificity of expression can be analyzed at the single cell level or quantitatively in tissue lysates. The ability to examine expression of single cells within a complex tissue is particularly useful for studies involving early embryogenesis.

Alternative reporter genes to that of LacZ include alkaline phosphatase and green fluorescent protein or its derivatives. Embryos formed according to Example 1 may express LacZ at a peak level as early as 7.5 dpc of development, continuing to as late as 16.5 dpc. The LacZ expression in the mouse model of the present invention may be identified in the intraembryonic para-aorta splanchnopleura and in the aorta-gonad-mesonephros (AGM) region; see below). As such, they are uniquely suited for studies on hematopoiesis at later developmental stages and have utility in a variety of in vitro and in vivo studies on embryonic hematopoiesis. Consequently, these animals have utility as a source of genetically marked erythroid cells for various kinds of explant or embryo cultures.

Using the transgenic methodology described in the invention, LacZ transgenic mice may be used as models for modulation of expression of hematopoiesis and vascular growth in either embryonic or adult animal by utilizing enhancers and/or promoters that direct the timing of expression during development or directing the tissue specificity of expression, such enhancer optionally being inducible. Examples include α-fetoprotein enhancer that directs gene expression to the yolk sac and developing gut, cardiac actin enhancer that directs expression to heart muscle, and sca-1 regulatory sequences to express protein in hematopoietic stem cells (Miles et al. *Development*, Vol. 124, (1997) pp. 537–547), or a retina-specific regulatory element of the interphotoreceptor retinoid-binding protein (Bobola et al. *J. Biol. Chem.* Vol 270, (1995) pp 1289–1294). Other transgenic mice may be formed in which a selected sequence from the hedgehog gene family may be placed under control of an enhancer and/or promoter of the sort described above. Furthermore, transgenic mice may be generated in which the hedgehog or hedgehog agonist or antagonist is expressed under the control of heterologous tissue specific promoters/enhancers such as described above. Other transgenic animals may be formed in which hedgehog regulatory sequences are used to drive expression of heterologous gene coding sequences in specific embryonic or adult tissues eg Ihh regulatory sequences for driving the expression of Shh or Dhh.

Transgenic mouse models according to the above may be formed by the methodology described in Example 1. "Knock-in" mice may be made using the method of Hanks et al. *Science* vol 269 (1995)pp 679–682, to target hedgehog genes into selected sites in the genome under the control of endogenous sequences in embryonic stem (ES) cells. These modified ES cells may then be micro-injected into blastocysts to form chimeric animals. (Joyner 1995). These animals are heterozygous for the targeted gene and will misexpress the introduced sequences. In this manner, control of the level of gene expression and of the sites at which expression occurs may be achieved. An example of such a transgenic mouse would be one in which Ihh sequences are "knocked into" the endogenous flk-1 locus to permit expression in HSC and endothelial cell precursors. The transgene ("knock-in" gene) can be modified as a fusion protein with for example LacZ or GFP, to permit convenient histochemical or immunological or molecular detection.

The use of transgenic animal technology can provide mouse model systems for applications including the following: identifying additional events in the normal processes of hematopoiesis and vascular growth in embryonic, fetal and adult mammals and events that give rise to blood diseases such as leukemias, and abnormal vascular growth and abnormal hematopoiesis. These events may be analyzed with regard to hedgehog compounds.

Therapeutic Applications:

There are a number of therapeutic applications for compounds of the invention. Such uses are associated with the modulation of hematopoiesis and vascular growth and include methods that result in stimulation as well as those that result in inhibition of proliferation and/or differentiation of stem cells. Examples of compounds of the invention have been discussed above.

In embodiments of the invention, the method of stimulating hematopoiesis and vascular growth may utilize:

(a) therapeutic compounds such as hedgehog proteins including derivatives, analogs, and degradation products of naturally occurring proteins; agonists or antagonists of protein receptors as well as functional equivalents of the above listed compounds. The therapeutic compounds may be isolated from cultures of extra-embryonic tissues, manufactured by recombinant technology or prepared by synthetic chemistry;

(b) coding sequences for the above-listed therapeutic compounds, incorporated into vectors suited for gene therapy techniques; and (c) mammalian cells that have been transformed with coding sequences of the above for cell transplantation.

Treatment of subjects with abnormal blood development can be achieved by administering, in an effective dose, for an effective time, a therapeutic agent that has been identified by one of the assays of the invention to the patient by any of the above methods. Alternatively, patients may be subjected to gene therapy by creating a plasmid or viral vector containing the coding sequence for the therapeutic agent using any of the techniques available in the art. For example, a protein, analogue, derivative, antagonist or receptor, of an identified protein (collectively called compounds) such as hedghog related compounds, may be introduced into a vector and the vector introduced into the appropriate target tissue where this tissue is located in an adult or in an embryo. The expression of the therapeutic agent may be regulated by a selected enhancer to ensure selective expression in the targeted tissue. For example, use of the cardiac actin enhancer to express the desired compound in the heart, the MCK enhancer to express the compound in skeletal muscle; sca-1 regulatory sequences to express hedgehog compound in hematopoietic stem cells or a retina-specific regulatory element of the interphotoreceptor retinoid-binding protein to express the compound in the retina.

Subjects with abnormal blood development can be treated by administering the therapeutic agent by means of cell transplantation using genetically manipulated cell lines as delivery systems of the secreted agent. For example, autologous cells such as autologous fibroblasts or heterologous cells contained within an immune protective barrier, may be manipulated by standard techniques to secrete the selected protein such as hedgehog, or analogues, derivatives, antagonists or receptors of protein.

In an embodiment of the invention, methods are provided for stimulating hematopoiesis in a subject to treat abnormalities associated with deficiencies in hematopoietic cell lineages. Examples of targets for such treatments include in vivo or in vitro exposure of undifferentiated mesodermally derived cells to a compound of the invention. Examples of target cells include bone marrow stem cells, progenitor cells, and cord blood cells. These cells may be isolated from a subject and stored in a cell bank for subsequent use, or the cells may be freshly isolated and maintained in vitro in a culture medium. Exposure of such cells to the compound results in enhanced proliferation and/or differentiation of the cells, the stimulated cells being implanted in the same or different subject from which the cells were derived, by means of transplantation technology. Alternatively, undifferentiated mesodermally derived cells may be accessed in the embryo or adult in vivo by any of a number of routes including: oral, intradermal subcutaneous, transmucosal, intramuscular or intravenous routes.

The method of the invention may be used to treat subjects (embryo or adult) suffering from blood abnormalities. These may arise from genetic lesions, side effects of therapeutic treatments such as radiation and chemotherapy for cancer or from disease caused by infectious agents such as human immune deficiency virus and may be treated using a method and compounds that stimulate hematopoiesis. The consequences of such abnormalities if untreated are various forms of anemia (associated with abnormally low levels of erythrocytes). Examples of anemias include: aplastic anemia (idiopathic, constitutional forms, or secondary forms); myelodysplastic anemia; anemia in patients with metastatic or necrotizing carcinoma; Hodgkin's disease; malignant lymphoma; anemia of chronic liver disease; anemia of chronic renal disease (renal failure); anemia of endocrine disorders; red cell aplasia; idiopathic or associated with other disorders, anemia due to chronic inflammatory disease; and thrombocytopenia of many etiologies. In addition, stimulation of hematopoiesis is beneficial in the treatment of leukopenias (for example, leukemia and AIDS).

According to an embodiment of the invention, a method is further provided for treating abnormal blood vessel formation (hypervascularization) resulting from genetic diseases, chronic degenerative disease, aging, trauma, or infectious agents. Examples include diabetic chronic ulcers, burns, frost bite, ischemic events following stroke and transplantation. The compounds of the invention may be used in the adult for induction of revascularization or formation of collateral vessels in ischemic myocardium or ischernic limbs, and in coronary artery bypasses and in promoting wound healing in general. For example, compounds of the invention may be used in treatment of duodenal ulcers by enhancing microvessel density and promoting more rapid healing. In addition, the method of the invention may be used to correct disorders of development in the embryo (as defined in above) caused by abnormalities in vascular growth.

According to an embodiment of the invention, methods are provided for inhibiting hematopoiesis in subjects suffering from excess production of erythrocytes for example polycythemia vera and erythroleukemia or other hematopoietic malignancies.

Similarly, methods are provided for inhibiting vascular growth in subjects suffering from excess vascularization or neovascularization as found in, for example, a variety of solid tumors such as breast cancer, hemangiomas in infancy, ocular neovascularization associated with diabetes, bleeding disorders of the female reproductive tract, and certain forms of arthritis.

All references cited above are incorporated by reference.

EXAMPLES

Example 1

Formation of Transgenic Mouse Models to Detect Formation of Primitive Erythroid Cells and Hematopoiesis Single erythroid cells formed during early embryogenesis can be identified by monitoring ε-globin expression. We developed novel ε-globin/LacZ vectors for transgene expression from which we obtained detailed histochemical data as well as data on the specificity of expression at the single cell level concerning hematopoiesis and vascular growth. Because the ε-globin/LacZ transgene is expressed only in primitive erythroid cells in mouse embryos (yolk sac and fetal liver), these mice serve as an ideal target for pharmacologic manipulation or examination of the effects of over-expressing or knocking out other genes that could affect embryonic hematopoiesis (which is primarily erythroid). For example, transgenic mice over-expressing a gene of interest may be crossed with one of the transgenic lines described above (homozygosed so that all progeny carry the LacZ reporter) and the effect on embryonic hematopoiesis measured by LacZ staining. Quantitative analysis of expression in tissue lysates were performed using the methods described by Wassarman, et al., *Guide to Techniques in Mouse Development* (San Diego: Academic Press, Inc., 1993); Herbomel, et al., Cell 39 (1984), 653–62). Alternatively, mice carrying targeted mutations (null mutations or other more subtle mutations) may be crossed with our transgenic mice and the effects of the mutations on embryonic hematopoiesis assessed. This in vivo assay is therefore a powerful tool for evaluating the effects of gene products on embryonic hematopoiesis.

We designed the transgene in association with a reporter gene to provide a sensitive enzymic assay for determining expression. Consequently we inserted β-galactosidase (LacZ) reporter gene into a vector downstream of a number of regulatory elements associated with the transcription of the human embryonic β-like hemoglobin (ε-globin) gene (FIG. 1). Examples of transgene constructs used to follow blood cell development are provided below. These constructs are illustrative of the method of the assay which need not be restricted solely to these constructs but may utilize other transgenes and other reporter genes in other vector constructs.

Description of Transgenes:

Several different transgenic constructs were generated containing a "micro-LCR" (a truncated version of regulatory sequences located far upstream of the β-globin gene locus, ref. Forrester et al., 1989) plus: the minimal ε-globin promoter alone (construct 1); the upstream regulatory region to −849 (construct 2); the upstream regulatory region to −2025 (construct 3); the minimal promoter driven by the combination ε-PRE II+V (construct 4) (Trepicchio, et al., *Mol. Cell. Biol.*, 13 (1993), 7457–7468). The prokaryotic β-galactosidase (LacZ) gene was inserted, along with a short oligonucleotide (SDK) containing a Kozak consensus sequence (Ravid et al.), between the minimal promoter and part of the second intron of the ε-globin gene, deleting E-globin sequences between +20 and +473. For each construct, 8–10 founders were obtained (14–21% transgenicity).

Generation of Transgene Constructs:

Construct 1: −179 lacZεµLCR (MB70):

This was the "basic cassette" and was created using a series of cloning steps.

MHB135 was first generated by three-way ligation between a ClaI/EcoRI fragment containing the human ε-globin gene from −849 to +1746, a 2.5 kb EcoRI/HindIII fragment containing a modified µLCR (Trepicchio, William L., et al., *Molecular and Cellular Biology*, Vol. 13, No. 12, pp. 7457–7468, (1993)), and a ClaI/HindIII-digested derivative of SP73 (Promega) in which the XhoI site had been destroyed by XhoI digestion, reaction with Klenow DNA polymerase, and then blunt ligation. A KpnI linker was then inserted at the EcoRV site of MHB135 to create MHB135K. A BamHI/XhoI fragment from pUCεx (Baron, et al., *Cell*, 46 (1986), 591–602.) containing the minimal ε-globin gene promoter from −179 to +20 was subcloned into BamHI/XhoI-digested SP73 (Promega), then excised by digestion with KpnI and XhoI and ligated into the backbone fragment of KpnI/XhoI-digested MHB135K to yield MB42.

MB42 was modified by insertion of a NotI linker at the HindIII site using standard methods (Sambrook, et al., *Molecular Cloning: A Laboratory Manual* (Cold Spring Harbor: Cold Spring Harbor Laboratory Press, 1989); this step introduced a unique NotI site at the end of the µLCR, yielding MB60.

MB59 was next generated as follows. The ~3.1 kb XbaI/PstI LacZ fragment from pSDKlacZpA (REF) was subcloned into SP73 to give SP73lacZ. The 3' portion of the human ε-globin gene from +474 to +1746 was excised as a BamHI/EcoRI fragment from pUCεx and blunt end-ligated into the blunted BamHI site of SP73lacZ to yield MB59. The KpnI site of MB59 was next destroyed by treatment with T4 DNA polymerase and relegation, yielding MB 69. Finally, the XhoI/EcoRI backbone of MB60 was ligated to a fragment containing LacZ and the ε-globin 3' sequences obtained by partial EcoRI and then XhoI digestion of MB69. This final product, MB70 was the basic construct, −179lacZεµLCR.

Construct 2: −849lacZεµLCR (MB73):

The ε-globin upstream region from −849 to +20 was isolated as a BglII/XhoI fragment from MHB135 and subcloned into the backbone of BglII/XhoI-digested MB70 to yield −849lacZεµLCR, denoted MB73.

Construct 3: −2kblacZεµLCR (MB 92):

A fragment of 2 kb containing the ε-globin upstream region from −2025 to +20 was excised from MB16-3 by digestion with KpnI and XhoI and was ligated into the backbone fragment of Kpn/XhoI-digested MB70-3 (−181lacZεµLCR, see above) to generate −2kblacZεµLCR (MB92).

MB16-3 was generated as follows. The 2 kb ε-globin upstream region was isolated from pUCεx (Baron and Maniatis, 1986) by digesting with EcoRI, blunting with Klenow DNA polymerase, and then digesting with XhoI. It was then ligated into KpnI/XhoI-digested MHB135K (see above).

Construct 4: ε-PRE(II+V)µLCR (MB72).

This vector was generated by ligating the BglII/BamHI fragment from construct 6 of FIG. 4 from ref. (Trepicchio et al., 1993) into the BamHI site of the basic construct, MB70.

Generation of Transgenic Mice:

For microinjection into embryos, plasmid DNAs were digested with KpnI/NotI restriction enzymes (FIG. 1) and the eukaryotic portions purified using standard methods (Hogan et al., 1994). The embryos were microinjected at the single cell stage with the DNA samples and then implanted into foster mothers, using standard methods (Hogan et al., 1994). An outbred mouse strain (CD-1) was used for generation of transgenic mice and has served as a source of embryo donors, stud males, pseudopregnant females, vasectomized males, and mature females for breeding. Tail biopsies were genotyped by Southern blotting (using a number of different probes, again by standard methods) or PCR (see below). Southern blot analysis was also used to confirm that no rearrangements, duplications or deletions accompanied genomic integration of the transgene. Founders were bred to obtain transgenic males (heterozygous transgenic CD-1 males) which were mated with normal CD-1 females to produce embryos or adult animals for LacZ expression analysis (see FIG. 2). Pregnant females were sacrificed at the times indicated in the figure (Noon of the day of vaginal plug observation was considered day 0.5 postcoitum (dpc)). Embryos were dissected, fixed and stained with XGal. For analysis of transgene expression in staged mouse embryos, enzymatic β-gal activity was followed by staining of whole mount embryos using a standard method (Wassarman and DePamphilis, 1993).

PCR Conditions for Genotyping Transgenic Mice:

Genomic DNA was prepared from toe clips of 10 day old pups or from tail biopsies of 3 week old pups. Toe clips were added to 20 µl of DNA extraction buffer (50 mM Tris-HCl, pH 8, 20 mM NaCl, 1 mM EDTA, 1% SDS) containing protease K (1 mg/mil) and incubated for 1 hr. at 55° C. with vortexing after the first 30 min. The samples were then diluted with 200 µl water, boiled for 10 min and microcentrifuged for 20 min. Genomic DNA was prepared from tail biopsies by a standard method (Hogan et al., 1994). PCR was carried out using 0.4 µl of genomic DNA (toe or tail) in a 50 µl reaction containing 1× Buffer G (PCR Optimizer kit, Invitrogen) and I.U. Ampli-Taq polymerase (Perkin-Elmer). Amplification was carried out for 32 cycles of denaturation at 94° C. (1 minute), annealing at 55° C. (1 minute), and extension at 72° C. (1 minute) followed by a final 6 min extension at 72° C. and resulted in a product of 408 bp. A portion (10–15 µl) of the reaction was analyzed on a 2% agarose gel in 1× Tris-borate-EDTA (Sambrook et al., 1989). The sequences of the amplification primers were:

5' Hε: 5'-ATG GAT CCA GCA CAC ATT A-3' (corresponds to −179 to −165 of Hε-globin gene) SEQ ID NO:1

3' LacZ: 5' -TCG CCA TTC AGG CTG CG-3' (corresponds to +154 to +170 of LacZ) (SEQ ID NO:2

Figure 2A:
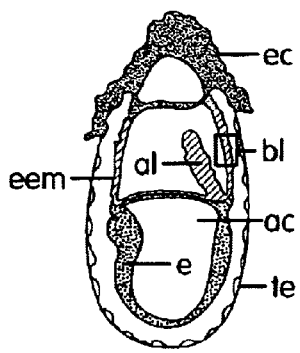
FIGS. 2A through 2F show LacZ expression, correlated with the appearance of a blue stain, in primitive erythroblasts. (A) is a diagramatic representation of a 7.5 dpc embryo; (B) is a transgenic embryo stained with XGal and viewed by bright field microscopy, (C) is the same embryo viewed by dark field microscopy; (D–E) are embryos at 8.5 dpc stained with XGal; (F) is a wild type 12.5 dpc embryo. (1) wild type; (2) transgenic; (3) ectoplacental cone; (4) blood islands; (5) amniotic cavity; (6) trophectoderm; (7) allantois; (8) extraembryonic mesoderm; (9) embryo proper (epiblast).
Figure 2B:
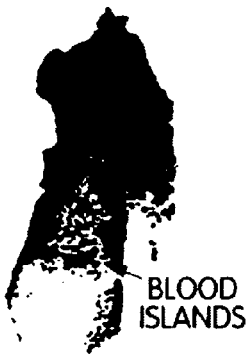
Figure 2C:
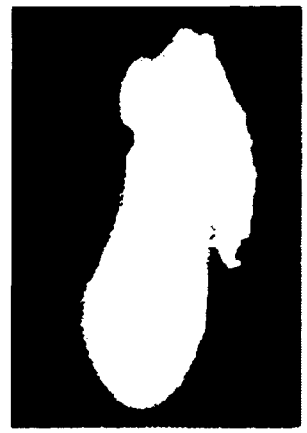
Figure 2D:
Figure 2E:
Figure 2F:

Results:

LacZ expression was detectable as early as 7.5 days post coitum (dpc) (i.e. about the time when blood islands are first seen in the yolk sac), in the expected "ring" pattern at the level of the exocoelom (FIG. 2A). By 8.5 dpc, staining of primitive erythroblasts within the vascular channels of the yolk sac was observed (FIG. 2B). Within the embryo proper, a small number of LacZ-staining primitive erythroblasts were observed (FIG. 2B(c)). By day 12.5, the time when mouse ε-globin gene expression peaks, LacZ-staining primitive erythroid cells were seen within yolk sac blood vessels (FIG. 2C). We have stained embryonic blood directly, to verify that these cells express LacZ.

Mice carrying MB 70, MB72 or MB73 expressed LacZ in primitive erythroid cells of the yolk sac and also in fetal liver at 16.5 dpc. Mice transgenic for MB 70 and MB 73 did not express LacZ in adult tissues. In contrast, in the absence of negative regulatory elements upstream of the promoter, MB72 transgenic mice also expressed LacZ in adult erythroid cells. MB 72 can therefore be used to study pharmacologic induction of anemias or polycythemia in adult animals. These mice may also be crossed with other transgenic or knockout mice to examine the effects on adult erythropoiesis of over-expressing or knocking out other genes. Examples of diseases which may be studied using these mice (after mating with other mice carrying appropriate mutations) include sickle cell anemia and the thalassemias (e.g.,Skow, L. C., et al., *Cell*, Vol. 34, pp. 1043–1052, (1983); Ciavatta, D. J., et al., *Proc. Natl. Acad. Sci. USA*, Vol. 92, pp. 9259–9263, (1995)).

With respect to yolk sac expression, primitive erythroid cells were LacZ-positive in MB 92 mice, similar to that detected for mice carrying any of the other three constructs.

Example 2

Demonstration that the Primitive Embryonic Mesoderm by Itself Cannot give rise to Hematopoiesis and Vascular Growth; Embryo Explant Cultures are used to Identify Agents that Stimulate Hematopoiesis and Vascular Growth in these Cultures Mice transgenic for a LacZ reporter linked to one of several human embryonic β-globin upstream regulatory sequences (FIG. 1) have been bred to homozygosity. These animals serve as a source of marked embryos in which the transgene is expressed only in primitive erythroid cells (FIG. 2).

(A) The Visceral Endoderm is Required for Primitive Hematopoiesis

The Embryo Explant Culture: Embryos from the transgenic mice of Example 1 were isolated around the onset of gastrulation at 6.25–6.5 dpc prior to the formation of hematopoietic mesoderm and were maintained individually in the chambers of an 8-well slide (Costar) or the wells of a 24-well plate (Costar) or in individual wells of Terasaki plates (Nunc) or in the wells of a 4 well plate for 48–72 hr. The embryos were then fixed and stained with XGal using a standard protocol (Wasserman, P. M. and Melvin L. DePamphilis, eds., *Guide to Techniques in Mouse Development*, Vol. 225, pp. 461–463. 1993) to monitor the generation of primitive erythroblasts. Whole embryos were cultured either in serum-containing medium or in chemically-defined medium (CDM) for LacZ-positive blood islands. CDM was similar to that used by (Johansson and Wiles, 1995) except that penicillin (1,000 U/ml), streptomycin (1,000 µg/ml), and Hepes pH 7.4 (20 mM) were added.

Separation of Visceral Endoderm from Epiblast: Pre-streak to early-streak embryos were enzymatically separated (Farrington, S. M., et al., *Mechanisms of Development*, Vol. 62, pp. 197–211, (1997)) into ectodermal (epiblast) and visceral endoderm components using trypsin/pancreatin (15 sec to 2 min) using a standard technique (Hogan et al., 1994). Tissue cross-contamination during this procedure was found to be negligible. (Farrington et al. 1997). Epiblasts or whole embryos were cultured individually. FIG. 2a depicts the epiblast which is a descendant of the inner cell mass of the blastocyst, from which ES cells are derived.

The visceral endoderm is required for primitive hematopoiesis in the mesoderm.

(a) Whereas LacZ-positive blood islands were easily detected in whole embryo cultures, little or no LacZ staining was observed in the epiblast cultures, either in chemically defined medium (CDM) or in Dulbecco's Modified Eagle's Medium (GIBCO-BRL) containing 30% heat-inactivated (56° C., 30 min) fetal bovine calf serum (HyClone). These results demonstrate that the mesoderm cannot on its own give rise to embryonic hematopoiesis but requires contact with or signals released from visceral endoderm. In contrast, epiblasts taken from later (6.75 to 7.5 dpc) embryos do form blood islands after 48 hours in culture, presumably because mesodermal cells present at this stage will already have received signals from the visceral endoderm.

(b) Recombination experiments: Epiblasts were recombined with visceral endoderm in collagen gels (rat tail collagen type I, Collaborative Biomedical Products). Collagen was prepared according to the instructions of the manufacturer. A 10 µl drop of collagen was allowed to solidify on the plastic surface; the tissues were then juxtaposed in a small depression created using watchmaker's forceps and then covered with 1 µl of collagen to hold them in place. Alternatively, tissues were gently expelled into a 5 µl drop of collagen and juxtaposed to allow physical contact; the collagen was then permitted to solidify. After 10 min, explant culture medium (DME supplemented with 30% FBS (heat-inactivated @ 56° C., 30 min), 2 mM glutamine, 10 mM Hepes pH 7.4, 68 µM α-methyl thioglycerol, penicillin (1,000 U/ml) and streptomycin (1,000 μg/ml) was added to the well (0.5 ml for 24 well dishes, less for smaller wells). Embryo fragments were manipulated using a drawn-out Pasteur pipet. All cultures were maintained at 37° C. and 5% $CO_2$. Medium was changed after one day. RNA was harvested after 3 days using the small scale method of (Chomezynski, P., et al., *Anal. Biochem*, Vol 162, pp. 156–159, (1987)) and analyzed for embryonic globin gene expression by RT-PCR (Farrington et al., 1997). These experiments demonstrated activation of globin gene expression when epiblasts were recombined with visceral endoderm and therefore established a requirement for visceral endoderm in induction of hematopoiesis during gastrulation (FIGS. 7, 8-1).

(c) Activation of primitive erythropoiesis by a diffusible factor in visceral endoderm cells: END-2 (Mummery et al., *Dev. Biol.*, 109 (1985), 402–410)—a visceral endoderm derived cell line, was grown to confluence in DME containing 15% fetal bovine serum (FBS) Cells were trypsinized, resuspended in 5 mls DME containing 30% FBS (DME-30) and gamma irradiated (6000 rad) using $^{137}Cs$ source. Cells were pipetted to break up the clumps and were then added to an additional 15 mlDME-30 in a 10 cm dish. The cells were allowed to condition the medium for 3 days at 37° C. (5%) $CO_2$. The medium was harvested, residual cells removed by centrifugation at 10 min at 1500 rpm and the supernatant was then sterilized using a 0.2 mm filter. The resulting conditioned medium (CM) was stored in aliquots at −80° C.

Epiblasts were incubated with (+) or without (−) CM. Most of the epiblasts cultured without CM failed to activate a marker of primitive erythropoiesis (the ε-globin gene), while most of the epiblasts cultured in the presence of CM did activate the gene. These results suggest that cell—cell contact is not essential for the stimulation of hematopoiesis by visceral endoderm, but that the effect is mediated by one or more diffusible factors. The asterisk in FIG. 10 indicates an artifactual amplification product.

The results show that for whole untreated embryos, 6/6 produced globin. In contrast, of 8 untreated epiblasts, only 1 showed any detectable expression. When conditioned medium was added, 8/10 epiblast cultures expressed globin.

Figure 5:
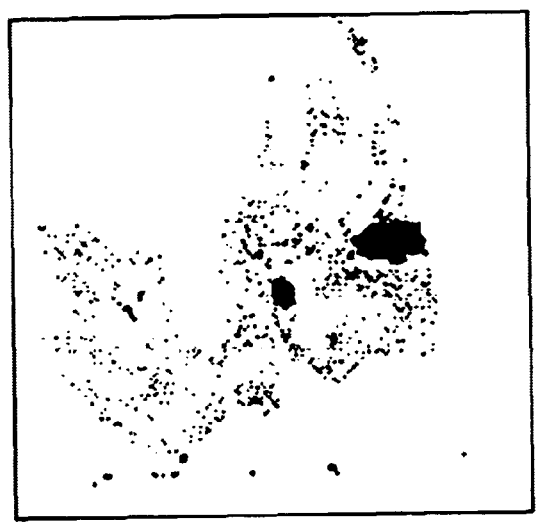
FIG. 5 shows that primitive erythropoiesis initiates late in gastrulation. On the left is a whole-mount in situ analysis of late-streak (~7.5 dpc) embryo and on the right is an early streak (~6.5 dpc) embryo. The purple stain is a chromogenic substrate. The $\epsilon$-globin RNA probe reveals hemopoietic cells in the embryo on the left as shown in the rostral (anterior) view, and none in the embryo on the right demonstrating absence of blood formation in the 6.5 dpc embryo.

Determination of the time at Which Hematopoiesis First Occurs During Mouse Development In situ Hybridization and Histology:

Whole-mount in situ hybridization was carried out as in Wilkinson and Nieto, 1993, using BM Purple (Boehringer Mannheim) as the substrate for alkaline phosphatase detection. The probe used is mouse ε-globin probe. The digoxigenin-labeled riboprobe was prepared by T7 polymerase transcription from an EcoR1-linearized DNA template termed SP73 mεRB, using a standard method (Wilkinson and Green, *Postimplantation Mouse Embryos: A Practical Approach*. Ed. A. Copp. Oxford: IRL Press, 1990). SP73 mεRB was generated by ligation of the EcoRI-BamHI fragment of the mouse ε-globin gene (Baron and Maniatis, 1986) from +187 to +439. This fragment contains a small region of the first intron and most of the second exon of this gene. The results of in situ hybridization on whole embryos to determine time at which hematopoiesis could be detected in wild type mice is shown in FIG. 5.

Multiplex RT-PCR protocol was used to measure induction of hematopoiesis because it is a more sensitive and quantitative assay for induction of hematopoiesis than XGal staining. It is also more versatile than XGal staining because it allows analysis of the expression of a variety of genes in a tissue. The starting material for this technique is RNA. Oligonucleotide primers were prepared. Examples of primers are provided in Table 1. Total RNA was prepared by guanidinium-acid-phenol extraction (Chomczynski, et al. (1987)) from the tissues of single embryos (6.25 to 6.5 dpc samples).

Total RNA was reverse transcribed with AMV reverse transcriptase (Life Sciences, Inc.) by standard methods, using oligo(dT) primer (Sambrook et al., 1989). Multiplex PCR was performed in a 15 μl reaction containing 5 pmol of β-actin primers (as an internal standard), 10–45 pmol of test gene primers and a trace amount of $[\alpha-^{32}P]$-dCTP to enable detection of amplification products by autoradiography following polyacrylamide gel electrophoresis. The primers used for PCR are described in Table 1. Amounts of input cDNA were normalized for β-actin expression. The cycle number and amounts of primer and template cDNA which yielded non-saturating amplification were determined empirically in each case.

Embryonic β-like globin (ε) gene expression was not detected in 6.5 dpc epiblasts or whole embryos isolated at 6.25 to 6.5 dpc. After 72 hr in culture, the ε-globin gene was activated in whole embryos but in isolated epiblasts little or no ε-globin transcription could be detected (FIGS. 7, 8). This demonstrated that embryonic hematopoiesis was not mesoderm-autonomous and that induction of embryonic globin gene expression occurred in the presence of visceral endoderm. This effect was consistent with a requirement for visceral endoderm for induction of embryonic globin gene expression. (The observed effect could be readily distinguished from the predicted effect of random events resulting from variations in embryo development in a litter in which isolated epiblasts at a more advanced stage of development at the time the embryo was harvested may provide low levels of globin gene expression).

(B) Blood Formation in the Anterior Portion of an Epiblast Obtained From a Late-stage Gastrulating Embryo Individual late stage gastrulating embryos (around 6.75 dpc) were harvested and the surrounding visceral endoderm was removed. At this time, the epiblast has already received visceral endoderm signals and has developed the capacity to form blood. However, this capacity appears to be localized at this time to the posterior region of the epiblast. We have shown here that the anterior region retains its dependence on the extraembryonic visceral endoderm. Visceral endoderm was enzymatically removed as described by Farrington et al. (1997) and the extraembryonic ectoderm was dissected away. The epiblast (embryonic ectoderm) was transected into anterior and posterior sections and incubated separately for 3 days. The posterior section was identified on the basis of morphological landmarks such as the primitive streak (posterior epiblast), as described by Downs et al. *Development*, vol. 118 (1993) 1255–1266 (FIG. 15). The results are shown in FIG. 5 and 16-1, 16-2, 16-3 and 16-4 and discussed below.

(i) During late stage gastrulation, the posterior but not anterior portion of the embryo is capable of forming blood in the absence of visceral endoderm Using RT-PCR as described above, little or no ε-globin expression was observed in the anterior portion of the embryo nor could blood development be observed histologically. In contrast, the posterior section formed blood even in the absence of the visceral endoderm, at levels comparable to that of an intact embryo (shown as control). Controls included (i) a PCR reaction carried out in the absence of cDNA template; (−c-DNA), (ii) RNA incubations carried out using a reverse transcription cocktail without reverse transcriptase (ant (−RT), post (−RT), Farrington et al, 1997). In this experiment, actin was amplified for 18 cycles and globin was amplified for 23 cycles.

(ii) Signals from visceral endoderm can restore ability of anterior portion of late gastrulation stage embryos to form blood.

(a) Four anterior and four posterior epiblast portions of late primitive streak stage embryos were cultured individually in the absence of visceral endoderm. As observed in the experiment of FIG. 2A, the posterior but not anterior portions of these late gastrulation stage embryos were able to form blood. In contrast, when anterior epiblast portions were cultured in collagen drops with visceral endoderm, blood formation was reconstituted in 2 of 4 samples (denoted "recombs" in figure). In this experiment, actin was amplified for 21 cycles and globin was amplified for 26 cycles.

(b) We determined that blood formation by mesoderm requires signals from visceral endoderm as follows: transgenic (Tg) embryonic ectoderms (epiblasts) were stripped of their visceral endoderm (VE) and recombined with non-transgenic VE in droplets of collagen. In these experiments, the only possible source of hematopoietic cells would be the transgenic epiblast but not the non-Tg VE. Tissues were cultured for 3–4 days and then stained with XGAL to identify areas of lacZ expression. These experiments demonstrated that blood formation was reconstituted in the presence of VE tissue. Furthermore, the localization of blood cells to the area immediately around the VE tissue suggested either that direct cell—cell contact is required or that short-range signaling by diffusible molecules is involved (FIG. 8-1).

Figures 3, 16:
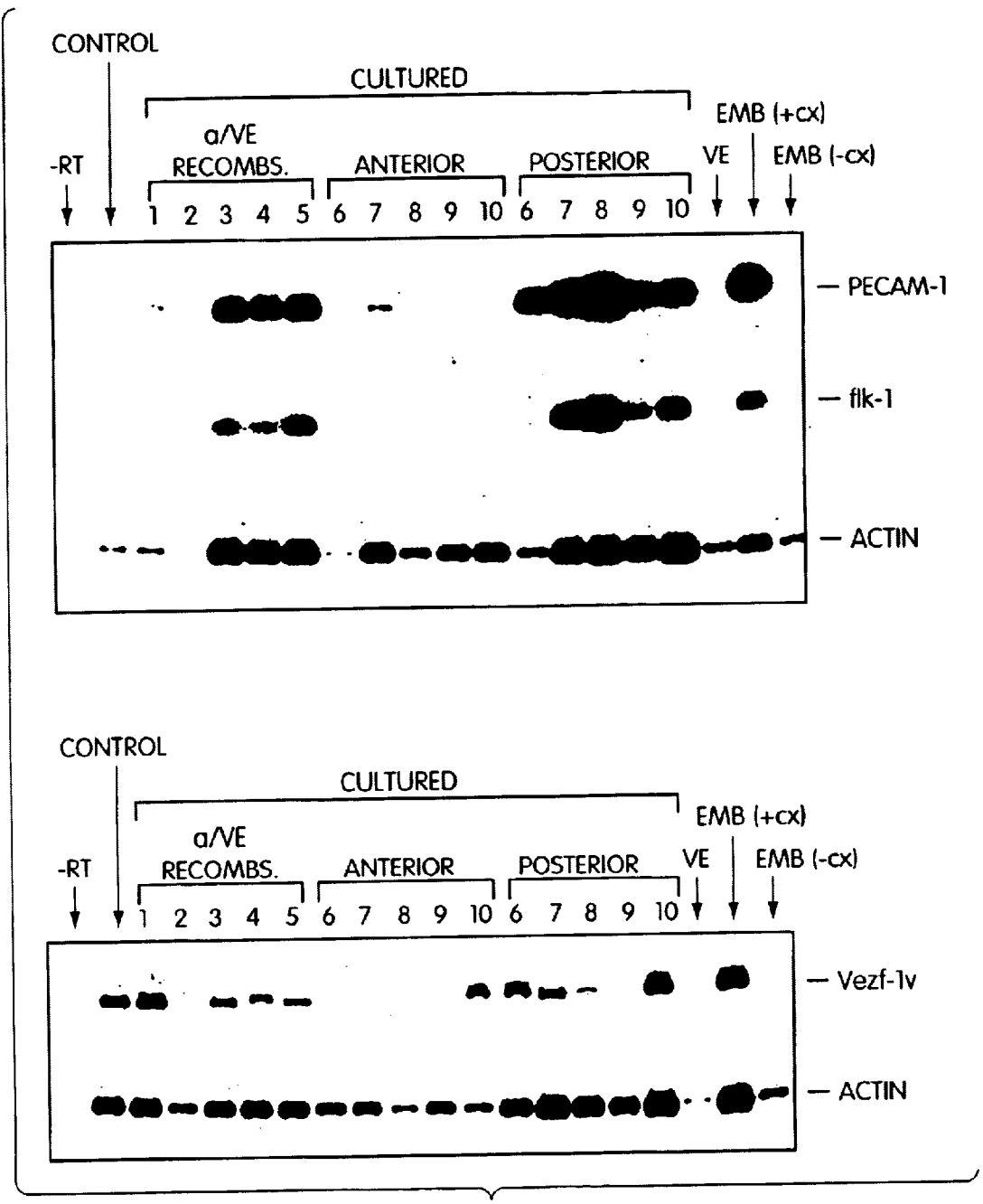

(c) We determined that the visceral endoderm can reprogram the anterior embryonic ectoderm of the epiblast to express both hematopoietic and vascular endothelial markers as follows: The anterior epiblast was recombined with visceral endoderm, to obtain activation of both hematopoietic markers (ε-globin, GATA-1, CD-34) shown in FIG. 16-2 and endothelial (PECAM-1, flk-1, and Vezf-1,) markers shown in FIG. 16-3. These markers were strongly expressed in cultured posterior epiblasts isolated at mid- to late gastrulation (FIG. 16-2, posterior lanes 6–10, and FIG. 16-3, posterior lanes 6–10) and in cultured whole embryos (emb+cx). Little or no expression of these markers was detected in visceral endoderm alone (FIG. 16-2, anterior lanes 6–10; FIG. 16-4, anterior, lanes 6–10) or in uncultured whole embryos (FIG. 16-2, emb (−cx); FIG. 16-3, emb (−cx)) from the same stage of development. These experiments showed that both hematopoietic and vascular tissue were induced by visceral endoderm signals and that the signals were instructive. As a specificity control, cardiac myosin which was expected to be expressed in cardiac tissue (and therefore only at a later developmental stage, around 7–8 dpc) (Lyons et al. 1990) was not detected in anterior or posterior epiblasts or in recombinants during the first 3 days in culture (FIG. 16-2, lanes 3–17) but was detected in a 10.5 dpc embryonic control (FIG. 16-2, 16-3). Vezf-1 (5') and (3') primers yielded a product of approximately 700 bp. Vezf-1 is a zinc finger protein homologous to a human protein termed db-1 and is expressed in the developing vasculature. It was shown to occur predominantly in the posterior epiblast and recombinant epiblasts but not in the anterior epiblasts (FIG. 16-3) PCR primers used to identify expression of markers

```
Primer sequences:
GATA-1 (5')    5'-CAGCACTAGGCCTACTACAG-3'  PCR product is 237bp; 32 cycles   (SEQ ID NO:3)

GATA-1 (3')    5'-TCAAGGTGTCCAAGAACGTG-3'                                    (SEQ ID NO:14)

Bra(5')        5'-TGCTGCCTGTGAGTCATAAC-3'  PCR product is 741bp; 34 cycles   (SEQ ID NO:5)

Bra(3')        5'-CTACTCTAAGGCAACAAGCC-3'                                    (SEQ ID NO:6)

Otx-2 (5')     5'-AGGAGCTGAGTCGCCACCTC-3'  PCR product is 312bp; 34 cycles   (SEQ ID NO:7)

Otx-2 (3')     5'-GTAGCCGACGGAGGGATGCA-3'                                    (SEQ ID NO:8)

CD34 (5')      5'-GTTACCTCTGGGATCCCTTC-3'  PCR product is 612bp; 32 cycles   (SEQ ID NO:9)

CD34 (3')      5'-GAGGTGACCAATGCAATAAG-3'                                    (SEQ ID NO:10)

PECAM-1 (5')   5'-TGCGATGGTGTATAACGTCA-3'  PCR product is 384bp; 32 cycles   (SEQ ID NO:11)

PECAM-1 (3')   5'-GCTTGGCAGCGAAACACTAA-3'                                    (SEQ ID NO:12)

Flk-1 (5')     5'-CCATACCGCCTCTGTGACTT-3'  PCR product is 507bp; 32 cycles   (SEQ ID NO:13)

Flk-1 (3')     5'-ACACGATGCCATGCTGGTCA-3'                                    (SEQ ID NO:14)

c-myosin(5')   5'-CTCGCAGAACAGCAGCCTAA-3'  PCR product is 679bp; 32 cycles   (SEQ ID NO:15)

c-myosin(3')   5"-AGGGTCTGCTGGAGAGGTTA-3'                                    (SEQ ID NO:16)
```

(C) Blastocysts Isolated at About 3.25–3.5 DPC Provide a Model System for Screening Compounds That can Stimulate Hematopoiesis and Vascular Growth of Undifferentiated Mesodermal Cells Blastocyst cultures were prepared and used to analyze the effects of compounds on the stimulation of undifferentiated mesodermal derived cells to undergo hematopoiesis and vasculogenesis. The blastocyst culture system described here is suited for following the development of embryonic structures in vitro, such as the yolk sac, that normally form post implantation in vivo. The effects of exogenously added growth factors or signaling molecules on development are analyzed here under defined conditions. Blastocysts may be obtained from wild type mice, transgenic mice or knock-out mice. Embryonic hematopoiesis in knockout mice was studied using null mutant blastocysts, obtained by crossing heterozygous animals. These null mutant blastocysts are preferred over null mutant embryonic stem (ES) cells used in vitro differentiation assays (Keller, *Current Opin. Cell Biol.*, 7 (1995) 862–69) because of their greater ease of isolation.

The blastocyst assay relies on the recovery of embryos from mice at a time prior to implantation of the embryo into the uterus of the mother at about 4.5 dpc. Here, blastocysts were obtained from (a) ε-globin/LacZ transgenic mice prepared according to Example 1 and analyzed by Lac Z staining; and (b) non-transgenic mice or knockout mice where individual blastocysts were analyzed at the molecular level for expression of multiple genes by RT-PCR.

Blastocysts were harvested at 3.25 to 3.5 dpc as described by Robertson, *Teratocarcinomas and Embryonic Stem Cells: A Practical Approach*. Oxford: IRL Press, 1993. We have successfully cultured blastocysts from several different mouse strains. In this example, CD-1 mice were used. The culture method was based on the method of Chen and Hsu (Chen, et al., *Exp. Hemat*, 7 (1979) 231–44.). However, superovulated females were not used. After harvesting, the blastocysts were washed free of contaminating maternal blood cells by two to three sequential transfers in drop cultures under mineral oil (Robertson, pp 471–478, ed IRL Press 1987) and transferred into untreated 35 mm plastic tissue culture dishes or into the wells of a 24 well dish. The blastocysts adhered to the plastic, reorganized and grew. Blastocysts were cultured individually (in wells of 24 well dishes) or in groups (35 mm plates or 24 well dishes) of up to 20, in CMRL-10 medium for the first 48 hr and then in CMRL-20 for up to 10 days at 37° C. and 5% $CO_2$. CMRL-10 was CMRL1066 medium (GIBCO-BRL) containing 10% heat-inactivated fetal bovine serum, penicillin (2,000 U/ml), streptomycin (2,000 μg/ml), 2 mM glutamine, 1 mM pyruvate, 0.1 mM nonessential amino acids (GIBCO-BRL), and $10^{-4}M$ β-mercaptoethanol. Sac-like structures could first be seen around 7 days in culture; by 9–10 days they had enlarged to the point where they were easily visible with the naked eye (0.5–2 mm in diameter). These sac-like structures (here termed "blastosacs") closely resembled early murine yolk sacs.

Transgenic blastosacs were stained in situ for LacZ expression using standard methods (Wassarman and DePamphilis, 1993). For analysis by RT-PCR, individual blastosacs were transferred into eppendorf tubes using a P200 pipetman and were microfuged for 10 min at 4° C. Medium was aspirated and RNA was isolated from tissue pellets (Chomczynski et al. 1987). A portion (5 to 8 μl out of 25 μl) of the RNA was used for synthesis of cDNA (Farrington et al., 1997 incorporated by reference). 0.5 to 2 μl of RNA were amplified by PCR in 50 μl as described (Farrington et al., 1997). In FIG. 4, samples underwent 35 cycles of amplification and 10 μl of the reaction mixture was then analyzed by electrophoresis through a 2% agarose gel containing ethidium bromide.

Actin and mouse GATA-1 PCR primers have been described previously (Baron et al., *Molecular and Cellular Biology*, vol 14, (1994) pp. 3108–3114). All other primers were used at an annealing temperature of 55° C. Primer sizes were: mouse ε-globin, 487 bp; mouse NF-E2, 257 bp; mouse EKLF, 129 bp; PTH/PTHrP receptor, 279 bp; PTHrP, 421 bp. Primer sequences were:

Mε forward: 5'-GGA AAA AAC CCT CAT CAA TG-3' (SEQ ID NO: 17)

ME reverse: 5'-ATT CAT GTG CAG AGA GGA GGC ATA-3'(SEQ ID NO:18)

mNF-E2 forward: 5'-cga CTA GTT CGG GAC ATC CG-3' (lower case letters indicate SpeI site) (SEQ ID NO:19)

mNF-E2 reverse: 5'-atg gta ccG TAC ATA TTC CTC TGG TG-3' (lower case, KpnI site) (SEQ ID NO:20)

EKLF forward: 5'-cga cta GTG GCG GTC TGA GGA GAC-3' (lower case, SpeI site) (SEQ ID NO:21)

EKLF reverse: 5'-atg gta ccA CGC ACA GGT CAC GT-3' (lower case, KpnI site) (SEQ ID NO:22)

Figure 3A:
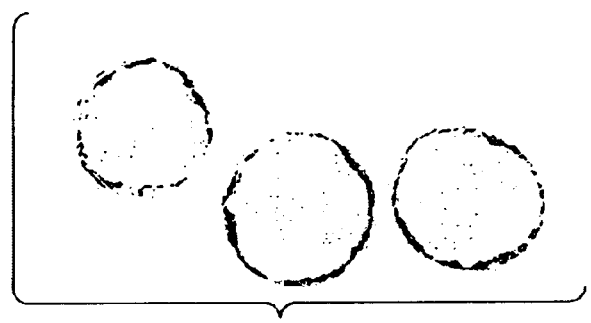
FIGS. 3A through 3D show the formation of yolk sac-like structures by cultured blastocysts: (A) transgenic blastocysts prior to culture; (B) sac-like structure (non transgenic) stained with benzidine to reveal hemoglobin containing cells; (C) sac from cultured transgenic blastocysts stained with XGal to reveal hemoglobin containing cells after 9 days of cultivation; and (D) normal 8.5 dpc transgenic embryo and yolk sac stained with XGal.
Figure 3B:
Figure 3C:
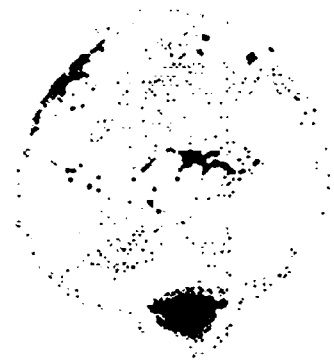
Figure 3D:

Hemoglobinized tissue was identified in these "blastosacs" following staining with benzidine (FIG. 3b). Benzidine staining corresponds to the presence of hemoglobin in erythroid cells. This was confirmed by analyzing embryos from transgenic mice. In these mice, LacZ expression was observed only in primitive erythroblasts but not in other embryonic cell types. Transgenic blastocysts were cultured for 9 days and then stained with X-Gal. As can be seen from FIG. 3C, erythroid cells produced in the developing blastosacs are easily revealed by their blue color after staining. Both wild type blastosacs and those derived from transgenic marker lines appear to contain vascular channels and resemble early embryonic yolk sacs (FIG. 3D) rather than later yolk sacs with well developed vasculature (compare with FIG. 2). The culture method described above provided blastosacs with an efficiency of between 40–80%.

RT-PCR was used to identify the temporal pattern of expression of mesodermal and endodermal markers in developing blastosacs and the effects of different growth factors and extracellular matrix components on the formation of different cell types. As shown in FIG. 4A, embryonic globin is produced only when yolk sac-like structures form, but not if the blastocysts do not progress in their development beyond an amorphous mound of trophectoderm cells.

Null mutant embryos were analyzed to determine the effects on hematopoiesis and vascular growth of mutations introduced into the mouse gerinline by gene targeting. Blastocyst cultures were harvested at 3.5 dpc from heterozygous Bmp-4 knockout mice (Winnier, G., et al., *Genes & Development*, Vol. 9, pp. 2105–2116, (1995)) that were crossed to give rise to homozygous null mutant offspring. The blastocysts were incubated in culture for varying periods of time (for example 9 days), after which time, individual blastosacs were removed from the culture plate for RT-PCR analysis, leaving behind the trophectodermal tissue. This tissue was used for genotyping so as to establish that the transgenic mice from which the blastocysts are derived, were homozygous. Whole-mount in situ hybridization and immunohistochemistry was also used to identify presumptive mutants for mutations resulting in a severe deficiency in erythroid cells or endothelium.

Null mutant "embryoid bodies" Embryoid bodies are structures derived from ES cells that form blood islands under appropriate culture conditions (Keller (1995)). We have developed an assay system using embryoid bodies to show that null mutant embryoid bodies such as Bmp-4, form little or no blood, and that this defect can be rescued by addition of exogenous, recombinant protein (BMP-4). The ES cells used in this experiment were derived from the TL-1 subline. However, the assay conditions described below are effective for a number of other ES cell sublines. They are also effective whether the cells have been selected for feeder independence or are maintained on feeder cells (Joyner (1195) Gene Targeting: A Practical Approach (New York: IRL Press). with mutations in selected genes were rescued by addition of a compound that is functionally equivalent to the gene product expressed by the non-mutated gene.

ES cells carrying a null mutation in both alleles of the Bmp-4 gene were formed using standard techniques (Joyner (1995) Gene Targeting: A Practical Approach. (New York: IRL Press), Keller, Current Opin. Cell Biol. 7, (1995) 862–869; Orkin Current Opin. Cell Biol. 7 (1995) 870–877, Mortensen, Molec. Cell Biol. 12 (1995) 2391–2395). These cells were plated at about $2.5 \times 10^5$ cells on a 6 cm bacterial dish containing 5 ml of IMDM/15% serum (either plasma derived serum or a 1:1 mixture of PDS and fetal bovine serum). The addition of exogenous growth factors such as erythropoietin or IL-3 was not found to be necessary here, despite a large literature that claims that different cocktails of growth factors are essential (e.g. Keller 1995,). After 24 hr, ES cells had formed aggregates and these were gently resuspended in the same medium and plated in 0.8% methylcellulose in IMDM containing 10% serum with or without BMP-4 (recombinant human, from Genetics Institute; 2 ng/ml). FIG. 17 (A) and (C) show wild type (parental) TL-I cells at low (A) and high (C) magnification. 87% of embryoid bodies from wild type ES cells became hemoglobinized after 10 days (see table at top of figure). In contrast, only 4% of the embryoid bodies from null mutant ES cells (B) became hemoglobinized. When BMP-4 was added to the cultures (D), the number of embryoid bodies to increased to about 59%. These results were confirmed using semi-quantitative RT-PCR assay for embryonic B-globin described above. These results show that inhibition of hematopoiesis can occur as a result of a mutation in the Bmp-4 gene and this deficiency can be reversed by the addition of exogenous BMP-4 protein.

Example 3

Compounds That are Functionally Equivalent to a Gene Product Expressed in an Embryo's Extraembryonic Tissue (Exemplified by Hedgehog Protein) Stimulate Hematopoiesis and Vascular Growth of Undifferentiated Mesodermal Cells (Exemplified by Epiblast Mesoderm)

Figure 9:
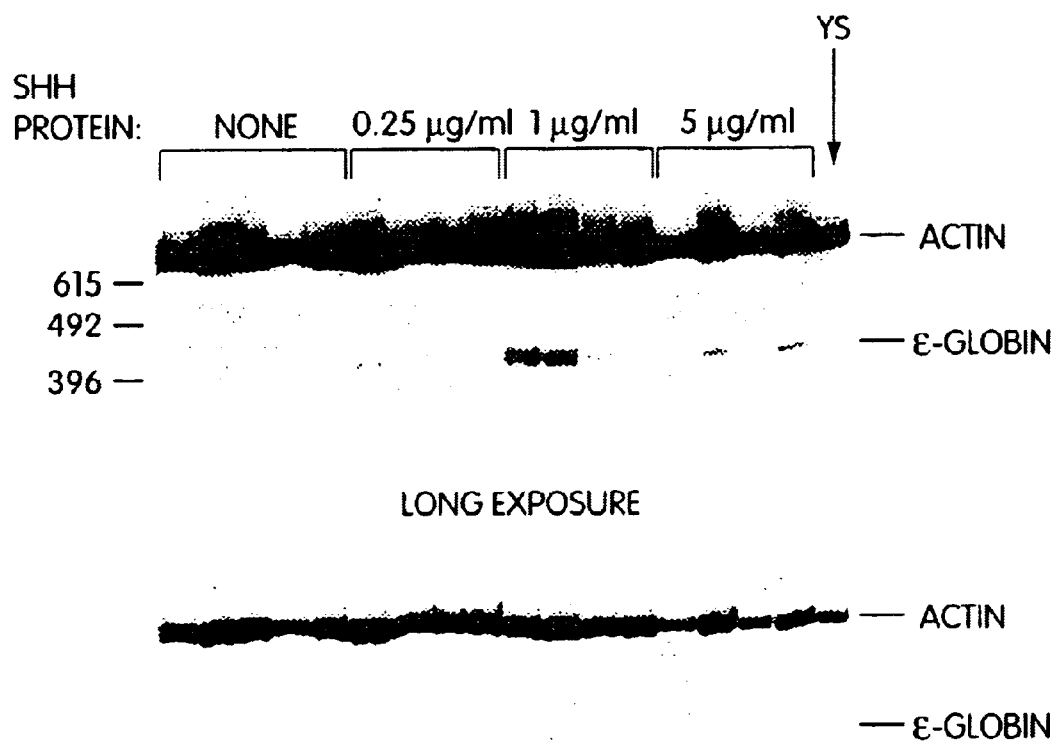
FIG. 9 shows that recombinant hedgehog protein can substitute for visceral endoderm to stimulate primitive hematopoiesis in cultured epiblasts. Isolated epiblasts were cultured in the absence (lanes labeled "none") or presence of three different concentrations of recombinant hedgehog protein (0.25, 1 and 5 $\mu$g/ml). Primitive hematopoiesis was assessed by RT-PCR analysis for $\epsilon$-globin expression. Actin served as an internal control. YS, yolk sac control.

(a) A hedgehog protein, typified by Sonic hedgehog, was demonstrated to stimulate hematopoiesis in the epiblast mesoderm using the method of Example 2(A) (FIG. 9). Bacterially expressed amino-terminal SHH protein (Bumcrot et al., 1995) in 20 mM Tris-HCl pH 7.6, 250 mM NaCl, 5% glycerol, and 1 mM DTT was diluted to 1 $\mu g/\mu l$ in 10 mg/ml bovine serum albumin (Stem Cells Technology). SHH protein was added at various concentrations (0.25 $\mu g/ml$ to 5 $\mu g/ml$;) to explant culture medium. Medium was changed after one day and RNA (Chomczynski and Sacchi, 1987) was isolated for RT-PCR analysis. FIG. 9 shows that SHH protein can substitute for visceral endoderm in a dose-dependent manner.

(b) Compounds that are functionally equivalent to a gene product expressed in an embryo's extraembryonic tissue (exemplified by hedgehog protein) stimulate hematopoiesis and vascular growth of undifferentiated mesodermal cells (exemplified by adult bone marrow cells).

To determine whether recombinant hedgehog proteins influence the development or differentiation of adult hematopoietic stem or progenitor cells, we carried out in vitro clonal assays. Mononuclear cells isolated from murine bone marrow were plated in methyl cellulose as follows:

Bone Marrow Hematopoietic Progenitor Assays:

Bone marrow was flushed from femur and tibias of from 2 to 3 female ICR mice, aged 5–6 weeks, by a standard method (Lord, in *Haemopoiesis: A Practical Approach*, pp 1–53, ed. Testa and Molineux, 1993 pub. Oxford University Press) and transferred to 5 ml of alpha medium (GIBCO-BRL) containing 2% fetal calf serum (hyClone). Mononuclear cells from pooled samples were isolated by centrifugation on a cushion of Ficoll (Accurate Chemical Co.) (Testa and Molineux, 1993) and cell numbers determined using a Coulter Counter. Cells were resuspended in Iscove's Modified Dulbecco's Medium (IMDM) at $3\times10^5$/ml and plated in a mixture of methyl cellulose (Fisher Scientific, 1.2%) in IMDM containing fetal calf serum (10%), deionized bovine serum albumin (cell culture grade BSA, 1%), 2-mercaptoethanol (1×10M) and the indicated growth factors and recombinant hedgehog proteins. Recombinant human erythropoietin (Epo) was obtained from Amgen and used at 40 U/ml. Recombinant interleukin-3 (IL-3) and granulocyte/macrophage-colony stimulating factor (GM-CSF) were used at 50 U/ml each. Portions (0.3 ml) of the methyl cellulose-mononuclear cell mixture were plated into 3 wells of each of two 4 well dishes (Nunc) for each growth condition tested. The fourth well of each dish contained $dH_2O$ to maintain humidity. Cultures were incubated in 5% $CO_2$ at 37° C. for approximately 2 weeks and colony numbers were scored on the days indicted. Colonies were scored as CFU-E, BFU-E, myeloid or mixed. Where included in the cultures, recombinant hedgehog proteins were added at concentrations between 1 and 5 $\mu g/ml$. Buffer alone (5 mM sodium phosphate pH 5.5 150 mM NaCl, 0.5 mM DTT) was added to some cultures as a negative control. For each culture condition, data were compile from counts of the 3 wells from each of two plates (6 wells total) ±standard deviations.

The mononuclear cells isolated from bone marrow were plated in methylcellulose containing hematopoietic growth factors alone (erythropoietin only; or GM-CSF+IL-3; or the combination Epo+GM-CSF+IL-3) or supplemented with one of histidine-tagged amino-terminal peptide of SHH (SHH-HIS), amino-terminal peptide of SHH (SHH-N), or histidine-tagged amino-terminal peptide of IHH. Cultures containing growth factors alone or growth factors plus buffer were used as negative controls.

In three independent experiments, colony numbers of all types (erythroid: CFU-E, BFU-E; myeloid: CFU-GM) were increased by −1.5 to more than 4-fold, in a dose-dependent manner (recombinant hedgehog protein added at 1, 2.5, 5 $\mu g/ml$, X ug). The observation that hedgehog proteins are apparently not selective for erythroid versus myeloid lineage is consistent with the hypothesis that they stimulate stem or early progenitor cell development. All three recombinant hedgehog proteins stimulated colony formation. From these data we conclude that both SHH and IHH enhance proliferation, differentiation and/or survival of hematopoietic stem/progenitor cells in vitro, even in the presence of one or more hematopoietic growth factors.

TABLE 1

Stimulation of bone marrow progenitor cells by recombinant HH proteins[1]

| Addition | Concentration ($\mu g/ml$) | CFU-E (day 2) | fold increase[2] | BFU-E (day 7) | fold increase | CFU-GM (day 11) | fold increase[2] |
|---|---|---|---|---|---|---|---|
| none | | 94.6 ± 8.2 | | 18.7 ± 3.9 | | 20.9 ± 0.9 | |
| buffer | | 84.7 ± 2.4 | | 14.7 ± 5.0 | | 27.1 ± 0.5 | |
| IHH-HIS | 1.0 | 134 ± 29.2 | 1.49 | 19.4 ± 3.7 | 1.16 | 27.1 ± 6.0 | 1.1 |
| | 2.5 | 150 ± 31.5 | 1.67 | 15.8 ± 2.6 | 0.95 | 29.3 ± 6.5 | 1.2 |
| | 5.0 | 156 ± 17.0 | 1.74 | 15.0 ± 3.6 | 0.90 | 42.5 ± 2.3 | 1.8 |
| SHH-N | 1.0 | 138 ± 30.0 | 1.54 | 14.3 ± 4.6 | 0.86 | 31.9 ± 5.4 | 1.3 |
| | 2.5 | 143 ± 31.5 | 1.59 | 20.2 ± 0.5 | 1.23 | 34.5 ± 9.9 | 1.4 |
| | 5.0 | 154 ± 25.2 | 1.72 | 21.3 ± 1.0 | 1.28 | 31.9 ± 4.1 | 1.3 |
| SHH-HIS | 1.0 | 197 ± 19.2 | 2.20 | 24.6 ± 1.0 | 1.47 | 30.8 ± 4.1 | 1.3 |
| | 2.5 | 153 ± 24.7 | 1.71 | 16.9 ± 1.9 | 1.01 | 32.6 ± 6.1 | 1.4 |
| | 5.0 | 146 ± 13.9 | 1.63 | 29.7 ± 3.2 | 1.78 | 43.4 ± 8.9 | 2.0 |

[1]All cultures contained EPO (2 U/ml), IL-3 (50 U/ml) and GM-C5F (2 ng/ml) plus the indicated addition (none, buffer or HH protein).
[2]Fold increase calculated based on average of the two control values (no addition or buffer only).

TABLE 2

Stimulation of bone marrow progenitor cells by recombinant HH proteins[1]

| Addition | concentration (µg/ml) | CFU-E (day 4) | fold increase[2] | BFU-E (day 8) | fold increase[2] | CFU-GM (day 8) | fold increase[2] |
|---|---|---|---|---|---|---|---|
| none |  | 31 |  | 14 |  | 20 |  |
| buffer pH 8.0[3] |  | 44 |  | 16 |  | 21 |  |
| buffer pH 5.5[3] |  | 34 |  | 29 |  | 27 |  |
| IHH-HIS | 5 | 63 | 1.75 | 25 | 1.25 | 25 | 1.09 |
|  | 10 | 88 | 2.44 | 29 | 1.45 | 45 | 1.96 |
|  | 25 | 130 | 3.61 | 31 | 1.55 | 43 | 1.87 |
| SHH-N | 5 | 71 | 1.97 | 47 | 2.35 | 28 | 1.22 |
|  | 10 | 76 | 2.11 | 42 | 2.10 | 27 | 1.17 |
|  | 25 | 136 | 3.78 | 46 | 2.30 | 28 | 1.22 |
| SHH-HIS | 5 | 112 | 3.11 | 27 | 1.35 | 38 | 1.65 |
|  | 10 | 101 | 2.81 | 24 | 1.20 | 41 | 1.78 |
|  | 25 | 111 | 3.08 | 29 | 1.45 | 45 | 1.96 |

[1]Erythroid colonies (CFU-E and BFU-E) were counted for cultures containing Epo (2 U/ml) plus the indicated addition (none, buffer or HH protein). Myeloid colonies (CFU-GM) were counted for cultures containing IL-3 (50 U/ml) and GM-CSF (2 ng/ml) plus the indicated addition.
[2]Fold increase was calculated based on average of the three control values (no addition or buffer only).
[3]HIS-tagged proteins were stored in buffer pH 8.0; untagged SHH was stored in buffer pH 5.5.

Other Approaches to Measuring the Effect of Compounds That are Functionally Equivalent to a Gene Product Expressed in an Embryo's Extraembryonic Tissue on Undifferentiated Mesodermal Cells:

An in vivo CFU-S spleen colony assay for multipotential and marrow repopulating cells was performed by injecting a source of hematopoietic stem/progenitor cells into mice. Macroscopic colonies formed in the spleen after 8–10 days reflected the presence of stem/progenitor cells (Testa and Molineux, 1993). As is the case for the in vitro progenitor assay described above, the maturity of the colony was reflected in the time taken for the colony to develop: early appearing colonies represented more mature progenitors while later-appearing colonies represented more primitive progenitors.

In a separate experiment, stem/progenitor cell populations from murine and human hematopoietic tissue are enriched by flow cytometry (florescence-activated cell sorting, FACS) or magnetic immunoselection (Testa and Molineux, 1993) and their development enhanced in the presence of hedgehog protein. These resulting populations are examined using in vivo assays include the CFU-S assay (spleen colony-forming unit) and long-term bone marrow cultures. A typical bone marrow culture includes a competitive repopulation assays and serial bone marrow transplantation studies (Morrison, et al., 1995a; Morrison et al., 1995b).

Example 4
Inhibition of Primitive Erythropoiesis in Cultured Whole Embryos Using a SHH Blocking Antibody.

Figure 11:
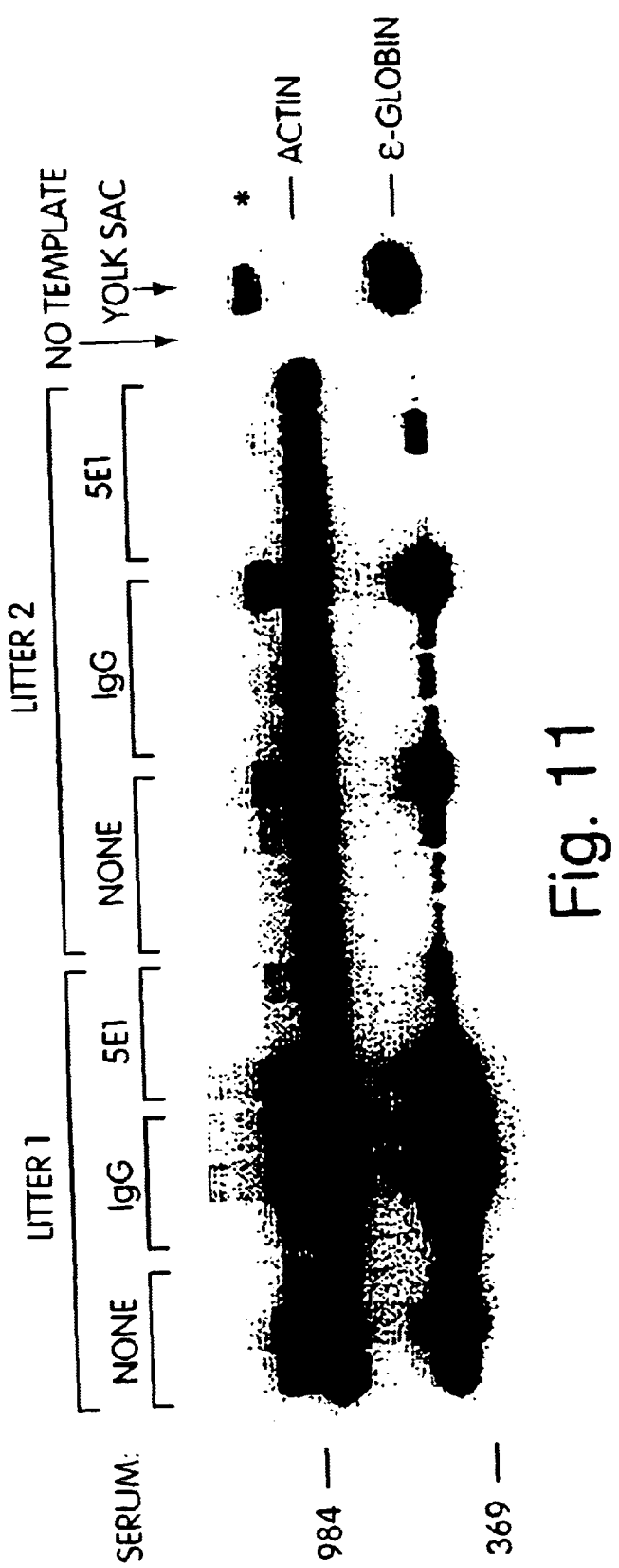
FIG. 11 shows the inhibition of primitive erythropoiesis in cultured whole embryos using a SHH blocking antibody by means of RT-PCR analysis.
Figure 12:
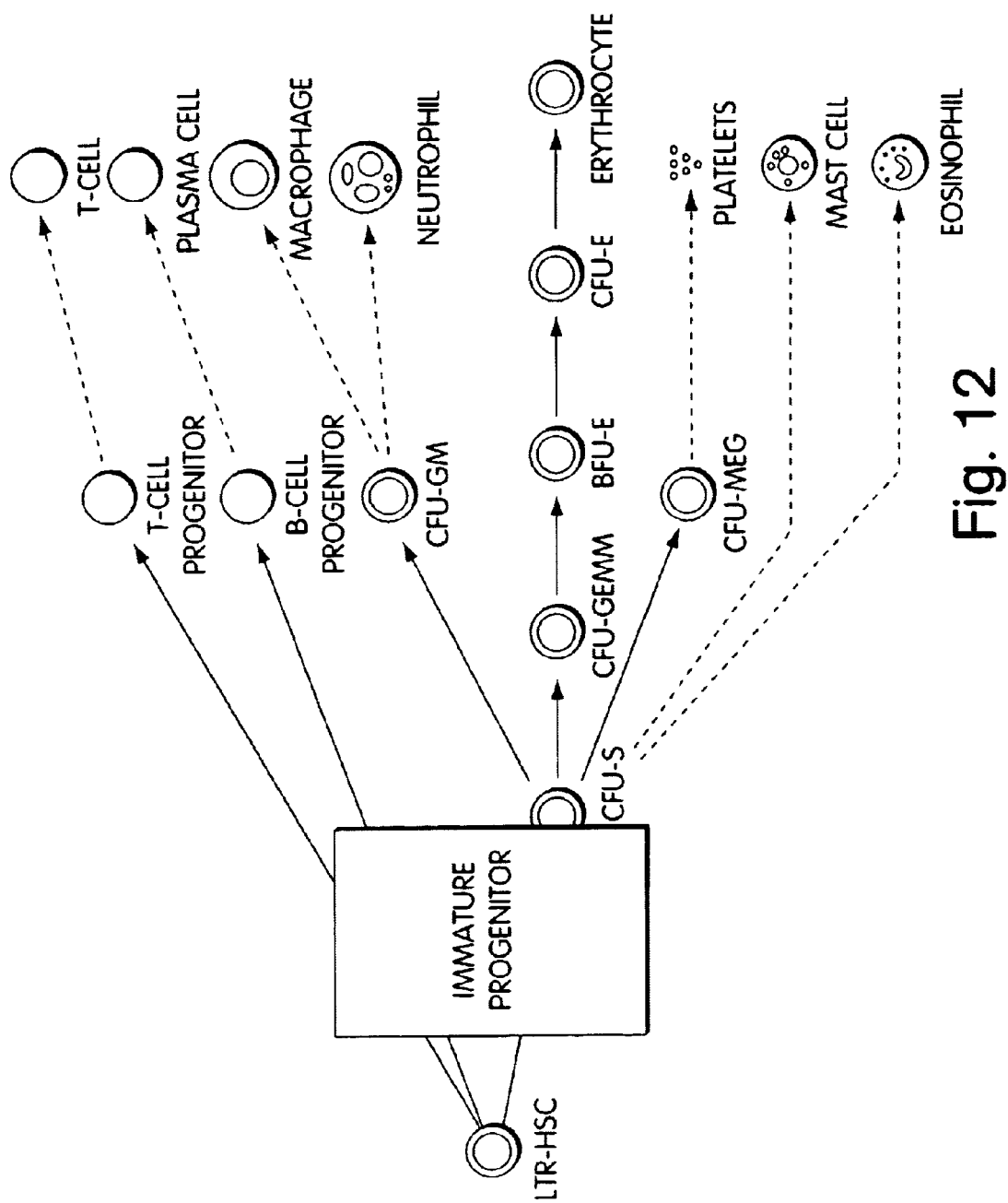
FIG. 12 shows a schematic representation of the adult hematopoietic hierarchy.

Whole embryos from two litters of mice were isolated at about 6.5 dpc and cultured individually in the absence of exogenous IgG (none) or in the presence of purified IgG (46 µg/ml) (Ericson et al., Cell 87 (1996), 661–73). Expression of embryonic ε-globin was assayed by the semi-quantitative RT-PCR method. The results are shown in FIG. 11. The asterisk indicates an artifactual amplified product. As predicted from Experiment 3, ε-globin expression was substantially reduced in the presence of the SHH blocking antibody.

Example 5
Cell Receptors Patched and Gli are Targets for Stimulation of Hematopoiesis and Vascular Growth.

Using the methods of Example 2(b), we showed that gene expression of patched and Gli was substantially exclusive in the yolk sac mesoderm. (FIG. 6) The enriched expression of Gli and patched in yolk sac mesoderm points to mesoderm as target of hedgehog signalling.: Yolk sacs from 10.5 and 12.5 dpc embryos were separated into endoderm (e) and mesoderm (m) fractions and RNA was prepared as described by Farrington et al (1997). RT-PCR analyses were carried out as described in Example 3 above using the following primers:

```
Gli-1 5': 5'-CAG GGA AGA GAG CAG ACT GA-3' (+465 to +484 of sequence)   (SEQ ID NO:25)

Gli-1 3': 5'-AGC TGA TGC AGC TGA TCC AG-3' (+697 to +716 of sequence)   (SEQ ID NO:24)

ptc 5':   5'-CTG CTG CTA TCC ATC AGC GT-3' (+3040 to +3059 of sequence) (SEQ ID NO:25)

ptc 3':   5'-AAG AAG GAT AAG AGG ACA GG-3' (+3491 to +3472 of sequence) (SEQ ID NO:26)
```

An annealing temperature of 55° C. and 23 cycles for both Gli and ptc and 16 cycles for actin was used (actin served as an internal control). The amplified products were 252 bp (Gli) and 453 bp (ptc). Both expression of Gli and ptc were found to be substantially exclusive to the mesodermal fraction of the yolk sac.

Example 6
Synergistic Effect of Hedgehog Protein with TGF-β Proteins on Hematopoiesis (and Vascular Growth)

Using the methods of Example 3(A) above, we have shown using RT-PCR, that both Indian Hedgehog and BMP-6 are expressed in early visceral endoderm. Whole embryo (6.5 dpc), epiblasts, epiblasts plus hedgehog protein, epiblasts plus BMP-6 protein and epiblasts plus hedgehog protein and BMP-6; are examined after 72 hrs incubation to determine the extent of activation of ε-globin expression. The experiment is repeated for BMP-2, BMP-4 and BMP-7. We expect to observe an enhanced effect when both hedgehog and BMP-4 are present compared with either alone.

We claim:

1. A method of stimulating a population of undifferentiated mammalian mesodermally derived cells to undergo hematopoiesis, comprising contacting the cells with an amount of a hedgehog compound effective to stimulate the cells to undergo hematopoiesis, wherein the hedgehog compound comprises a polypeptide sequence at least 80% identical to a sequence selected from SEQ ID NO: 34, SEQ ID NO: 35, SEQ ID NO: 36, SEQ ID NO: 37, SEQ ID NO: 38, SEQ ID NO: 39, SEQ ID NO: 40, or a fragment of said polypeptide sequence which polypeptide sequence or fragment of said polypeptide sequence binds to patched and induces cells to undergo hematopoiesis.

2. A method according to claim 1, wherein the hedgehog compound is an Indian hedgehog, Desert hedgehog, or Sonic hedgehog protein or a fragment thereof which binds to patched and induces cells to undergo hematopoiesis.

3. A method according to claim 1, wherein the hedgehog compound is an Indian hedgehog protein or a fragment thereof which binds to patched and induces cells to undergo hematopoiesis.

4. A method according to claim 1, further comprising maintaining the cell population in vitro in a culture medium, and wherein contacting the cells with a hedgehog compound includes contacting the cells with a culture medium comprising the hedgehog compound.

5. A method according to claim 1, wherein the undifferentiated mesodermally derived cells are hematopoietic stem cells.

6. A method according to claim 5, wherein the hematopoietic stem cells are selected from cord blood cells, fetal liver cells, and peripheral blood cells.

7. A method according to claim 5, wherein the hematopoietic stem cells are obtained from adult bone marrow cells.

8. A method according to claim 1, wherein the cells are progenitor cells obtained from an adult human.

9. A method according to claim 1, wherein the cells comprise embryonic tissue.

10. A method according to claim 1, wherein the cells comprise an embryonic explant culture.

11. A method according to claim 10, wherein the embryonic explant culture is a blastocyst.

12. A method according to claim 1, wherein the cells are hematopoietic stem cells within the bone marrow of an animal.

13. A method according to claim 12, wherein contacting the stem cells with the hedgehog compound includes administering an effective dose of the compound to the animal by any of oral, intradermal, subcutaneous, transmucosal, intramuscular, or intravenous routes.

14. A method according to claim 1, wherein the cells are hematopoietic stem cells present in the animal in at least one of bone marrow, cord blood cells, fetal liver cells and peripheral blood cells.

15. A method according to claim 1, further comprising contacting the cells with a TGF-β compound.

16. A method according to claim 15, wherein the TGF-β polypeptide is a bone morphogenic protein.

17. A method according to claim 16, wherein the bone morphogenic protein is BMP-2, BMP-4, BMP-6, or BMP-7.

18. A method according to claim 15, wherein the TGF-β polypeptide enhances the stimulation of hematopoiesis of the cells by more than the amount of stimulation of hematopoiesis resulting from administration of an identical amount of the TGF-β polypeptide in the absence of the hedgehog compound.

19. A method of stimulating hematopoiesis in an animal, comprising administering to the animal an effective amount of a hedgehog compound comprising a polypeptide sequence at least 80% identical to a sequence selected from SEQ ID NO: 34, SEQ ID NO: 35, SEQ ID NO: 36, SEQ ID NO: 37, SEQ ID NO: 38 SEQ ID NO: 39, SEQ ID NO: 40, or a fragment of said polypeptide sequence which polypeptide sequence or fragment binds to patched and induces cells to undergo hematopoiesis.

20. A method according to claim 19, wherein the hedgehog compound is an Indian hedgehog, Desert hedgehog, or Sonic hedgehog protein or a fragment thereof which binds to patched and induces cells to undergo hematopoiesis.

21. A method according to claim 19, further comprising contacting the cells with a TGF-β polypeptide.

22. A method according to claim 21, wherein the TGF-β compound is a bone morphogenic protein.

23. A method according to claim 22, wherein the bone morphogenic protein is selected from BMP-2, BMP-4, BMP-6, and BMP-7.

24. A method according to claim 19, wherein an effective dose of the hedgehog compound is administered to the animal by any of oral, intradermal, subcutaneous, transmucosal, intramuscular, or intravenous routes.

25. A method of stimulating a population of undifferentiated mammalian mesodermally derived cells to undergo hematopoiesis, comprising contacting the cells with an effective amount of a hedgehog compound comprising a polypeptide sequence of SEQ ID NO: 41, SEQ ID NO: 42, or a fragment of said polypeptide sequence which polypeptide sequence or fragment thereof binds to patched and induces cells to undergo hematopoiesis.

26. A method according to claim 25, wherein the undifferentiated mesodermally-derived cells are a population of hematopoietic stem cells.

27. A method according to claim 26, wherein the hematopoietic stem cells are selected from cord blood cells, fetal liver cells, and peripheral blood cells.

28. A method according to claim 26, wherein the cells are progenitor cells of human origin.

29. A method according to claim 26, wherein the cells are hematopoietic stem cells within the bone marrow of the animal.

30. A method according to claim 26, wherein the cells are hematopoietic stem cells present in the animal in at least one of bone marrow, cord blood cells, fetal liver cells and peripheral blood cells.

31. A method of stimulating hematopoiesis in an animal, comprising administering to the animal an effective amount of a hedgehog compound comprising a polypeptide sequence of SEQ ID NO: 41, SEQ ID NO: 42, or a fragment of said polypeptide sequence which polypeptide sequence or fragment thereof binds to patched and induces cells to undergo hematopoiesis.

32. A method of stimulating a population of undifferentiated mammalian mesodermally derived cells to undergo hematopoiesis, comprising contacting the cells with an amount of a hedgehog compound effective to stimulate the cells to undergo hematopoiesis, wherein the hedgehog compound comprises a polypeptide sequence encoded by a nucleic acid which hybridizes under stringent conditions, including a wash step of 0.2×SSC at 65° C., to a nucleic acid sequence designated in one of SEQ ID Nos. 27–33, which polypeptide sequence binds to patched and induces cells to undergo hematopoiesis.

33. A method according to claim 32, wherein the hedgehog compound is an Indian hedgehog, Desert hedgehog, or Sonic hedgehog protein or a fragment thereof which binds to patched and induces cells to undergo hematopoiesis.

34. A method according to claim 32, wherein the hedgehog compound is an Indian hedgehog protein or a fragment thereof which binds to patched.

35. A method according to claim 32 further comprising contacting the cells with a TGF-β compound.

36. A method according to claim 35, wherein the TGF-β compound is a bone morphogenic protein.

37. A method according to claim 36, wherein the bone morphogenic protein is BMP-2, BMP-4,BMP-6, or BMP-7.

38. A method according to claim 35, wherein the TGF-β polypeptide enhances the stimulation of hematopoiesis of the cells by more than the amount of stimulation of hematopoiesis resulting from administration of an identical amount of the TGF-β polypeptide in the absence of the hedgehog compound.

39. A method according to claim 32, further comprising maintaining the cell population in vitro in a culture medium, and wherein contacting the cells with a hedgehog compound includes contacting the cells with a culture medium comprising the hedgehog compound.

40. A method according to claim 32, wherein the undifferentiated mesodermally cells are hematopoietic stem cells.

41. A method according to claim 40, wherein the hematopoietic stem cells are selected from cord blood cells, fetal liver cells, and peripheral blood cells.

42. A method according to claim 40, wherein the hematopoietic stem cells are obtained from adult bone marrow cells.

43. A method according to claim 32, wherein the cells are progenitor cells obtained from an adult human.

44. A method according to claim 32, wherein the cells comprise embryonic tissue.

45. A method according to claim 32, wherein the cells comprise an embryonic explant culture.

46. A method according to claim 45, wherein the embryonic explant culture is a blastocyst.

47. A method according to claim 32, wherein the cells are hematopoietic stem cells within the bone marrow of an animal.

48. A method according to claim 32, wherein the cells are hematopoietic stem cells present in the animal in at least one of bone marrow, cord blood cells, fetal liver cells and peripheral blood cells.

49. A method according to claim 48, wherein contacting the stem cells with the hedgehog compound includes administering an effective dose of the compound to the animal by any of oral, intradermal, subcutaneous, transmucosal, intramuscular, or intravenous routes.

50. A method of stimulating a population of undifferentiated mammalian mesodermally derived cells to undergo hematopoiesis, comprising contacting the cells with means for activating hedgehog signaling in an amount effective to stimulate the cells to undergo hematopoiesis.

51. A method according to claim 50, wherein the means for activating hedgehog signaling comprises Indian hedgehog, Desert hedgehog, or Sonic hedgehog protein or a fragment thereof which binds to patched and induces cells to undergo hematopoiesis.

52. A method according to claim 50, wherein the means for activating hedgehog signaling comprises Indian hedgehog protein or a fragment thereof which binds to patched.

53. A method according to claim 50, further comprising contacting the cells with a TGF-β polypeptide.

54. A method according to claim 53, wherein the TGF-β polypeptide is a bone morphogenic protein.

55. A method according to claim 54, wherein the bone morphogenic protein is BMP-2, BMP-4, BMP-6, or BMP-7.

56. A method according to claim 53, wherein the TGF-β polypeptide enhances the stimulation of hematopoiesis of the cells by more than the amount of stimulation of hematopoiesis resulting from administration of an identical amount of the TGF-β polypeptide in the absence of the means for activating hedgehog signaling.

57. A method according to claim 50, further comprising maintaining the cell population in vitro in a culture medium, and wherein contacting the cells with a means for activating hedgehog signaling includes contacting the cells with a culture medium comprising the means for activating hedgehog signaling.

58. A method according to claim 50, wherein the undifferentiated mesodermally derived cells are hematopoietic stem cells.

59. A method according to claim 58, wherein the hematopoietic stem cells are selected from cord blood cells, fetal liver cells, and peripheral blood cells.

60. A method according to claim 58, wherein the hematopoietic stem cells are obtained from adult bone marrow cells.

61. A method according to claim 50, wherein the cells are progenitor cells obtained from an adult human.

62. A method according to claim 50, wherein the cells comprise embryonic tissue.

63. A method according to claim 50, wherein the cells comprise an embryonic explant culture.

64. A method according to claim 63, wherein the embryonic explant culture is a blastocyst.

65. A method according to claim 50, wherein the cells are hematopoietic stem cells within the bone marrow of an animal.

66. A method according to claim 65, wherein contacting the stem cells includes administering an effective amount to the animal by any of oral, intradermal, subcutaneous, transmucosal, intramuscular, or intravenous routes.

67. A method according to claim 50, wherein the cells are hematopoietic stem cells present in the animal in at least one of bone marrow, cord blood cells, fetal liver cells and peripheral blood cells.

68. A method of stimulating hematopoiesis in an animal, comprising administering to the animal means for activating hedgehog signaling in an amount effective to induce cells to undergo hematopoiesis.

69. A method according to claim 68, wherein the means for activating hedgehog signaling comprises Indian hedgehog, Desert hedgehog, or Sonic hedgehog protein or a fragment thereof which binds to patched and induces cells to undergo hematopoiesis.

70. A method according to claim 68, further comprising contacting the cells with a TGF-β polypeptide.

71. A method according to claim 70, wherein the TGF-β polypeptide is a bone morphogenic protein.

72. A method according to claim 71, wherein the bone morphogenic protein is selected from BMP-2, BMP-4, BMP-6, and BMP-7.

73. A method according to claim 68, wherein an effective dose is administered to the animal by any of oral, intradermal, subcutaneous, transmucosal, intramuscular, or intravenous routes.

74. A method of stimulating a population of undifferentiated mammalian mesodermally derived cells to undergo hematopoiesis, comprising contacting the cells with means for binding patched and thereby activating hedgehog signaling in an amount effective to induce cells to undergo hematopoiesis.

75. A method according to claim 74, wherein the undifferentiated mesodermally derived cells are a population of hematopoietic stem cells.

76. A method according to claim 75, wherein the hematopoietic stem cells are selected from cord blood cells, fetal liver cells, and peripheral blood cells.

77. A method according to claim 75, wherein the cells are progenitor cells of human origin.

78. A method according to claim 75, wherein the cells are hematopoietic stem cells within the bone marrow of the animal.

79. A method according to claim 75, wherein the cells are hematopoietic stem cells present in the animal in at least one of bone marrow, cord blood cells, fetal liver cells and peripheral blood cells.

80. A method of stimulating hematopoiesis in an animal, comprising administering to the animal means for binding patched and thereby activating hedgehog signaling in an amount effective to induce cells to undergo hematopoiesis.

* * * * *

UNITED STATES PATENT AND TRADEMARK OFFICE
CERTIFICATE OF CORRECTION

PATENT NO. : 6,713,065 B2
DATED : March 30, 2004
INVENTOR(S) : Margaret H. Baron et al.

It is certified that error appears in the above-identified patent and that said Letters Patent is hereby corrected as shown below:

Column 85,
Line 37, after "TGF-ß" insert -- polypeptide -- and delete "compound";
Line 54, after "or fragment" insert -- of said polypeptide sequence --;

Column 86,
Line 9, after "or fragment" insert -- of said polypeptide sequence -- and delete "thereof";
Lines 48 and 50, after "TGF-ß" insert -- polypeptide -- and delete "compound"; and
Line 64, after "mesodermally" insert -- derived --.

Signed and Sealed this

Twenty-fifth Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,713,065 B2
APPLICATION NO. : 09/021660
DATED : March 30, 2004
INVENTOR(S) : Baron et al.

It is certified that error appears in the above-identified patent and that said Letters Patent is hereby corrected as shown below:

In the Specification

Column 1, Line number 12, delete the paragraph beginning with "This invention" and ending with "the invention" and replace it with the following paragraph:
GOVERNMENT SUPPORT
This invention was made with government support under GM042413 awarded by the National Institutes of Health. The government has certain rights in the invention.

Signed and Sealed this
Thirty-first Day of December, 2024

Derrick Brent
*Acting Director of the United States Patent and Trademark Office*